(12) United States Patent
Monson

(10) Patent No.: US 8,394,583 B2
(45) Date of Patent: Mar. 12, 2013

(54) VH4 CODON SIGNATURE FOR MULTIPLE SCLEROSIS

(75) Inventor: Nancy Monson, Ovilla, TX (US)

(73) Assignee: The Board of Regents of the University of Texas System, Austin, TX (US)

( * ) Notice: Subject to any disclaimer, the term of this patent is extended or adjusted under 35 U.S.C. 154(b) by 405 days.

(21) Appl. No.: 12/509,093

(22) Filed: Jul. 24, 2009

(65) Prior Publication Data

US 2010/0022440 A1 Jan. 28, 2010

Related U.S. Application Data

(60) Provisional application No. 61/083,429, filed on Jul. 24, 2008.

(51) Int. Cl.
- C12Q 1/06 (2006.01)
- C12Q 1/68 (2006.01)
- G01N 33/50 (2006.01)

(52) U.S. Cl. ....... 435/6.1; 424/9.1; 536/23.1; 536/23.53

(58) Field of Classification Search .................. None
See application file for complete search history.

(56) References Cited

PUBLICATIONS

Weng et al., Eur J Immunology, 22:1075-1082, 1992.*
Dorner et al., The Journal of Immunology 158: 2779-2789, 1997.*
International Search Report and Written Opinion, issued in Application No. PCT/US2009/051647, date of mailing: Dec. 3, 2009.
Bennett et al., "VH4 gene segements dominate the intrathecal humoral response in multiple sclerosis," *Annals of Nuerology*, 62(Suppl. 11): S3, 2007.
Cameron et al., "Potential of a unique antibody gene signature to predict conversion to clinically definite multiple sclerosis," *Journal of Neuroimmunology*, 213:123-130, 2009.
Colombo et al., "Maintenance of B lymphocyte-related clones in the cerebrospinal fluid of multiple sclerosis patients," *Eur. J. Immunol.*, 33:3433-3438, 2003.
Kraj et al., "Evidence for the overexpression of the VH4-34 (VH4.21) Ig gene segment in the normal adult human peripheral blood B cell repertoire," *Journal of Immunology*, 154:6406-6420, 1995.
Baranzini et al., B cell repertoire diversity and clonal expansion in multiple sclerosis brain lesions, *J. Immunol.*, 163:5133-5144, 1999.
Bennet et al., "CSF IgG heavy-chain bias in patients at the time of a clinically isolated syndrome," *J Neuroimmunol.*, 199:126-132, 2008.
Bhat et al., "B cell lymphorproliferative disorders and VH4-34 gene encoded antobodies," *Human Antibodies*, 13:63-68, 2004.
Brezinschek et al., "Analysis of the heavy chain repertoire of human peripheral B cells using single-cell polymerase chain reaction," *J. Immunol.*, 155:190-202, 1995.
Brezinschek et al., "Pairing of variable heavy and variable kappa chains in individual naive and memory B cells," *J. Immunol.*, 160:4762-4767, 1998.
Buluwela and Rabbitts, "A VH gene is located within 95 Kb of the human immunoglobulin heavy chain constant region genes," *Eur. J. Immunol.*, 18:1843-1845, 1988.

Cepok et al., "Short-lived plasma blasts are the main B cell effector subset during the course of multiple sclerosis," *Brain*, 128:1667-1676, 2005.
Chothia and Lesk, "Canonical structures for the hypervariable regions of immunoglobulins," *J. Mol. Biol.*, 196:901-917, 1987.
Chothia et al., "Structural repertoire of the human VH segments," *J. Mol. Biol.*, 799-817, 1992.
Colombo et al., "Accumulation of clonally related B lymphocytes in the cerebrospinal fluid of multiple sclerosis patients," *J. Immunol.*, 164:2782-2789, 2000.
Damle et at, "Ig V gene mutation status and CD38 expression as novel prognostic indicators in chronic lymphocytic leukemia," *Blood*, 94:1840-1847, 1999.
del Pilar Martin and Monson, "Potential role of humoral immunity in the pathogenesis of multiple sclerosis (MS) and experimental autoimmune encephalomyelitis (EAE)," *Front Biosci.*, 12:2735-2749, 2007.
Domiati-Saad and Lipsky, "Staphylococcal enterotoxin A induces survival of VH3-expressing human B cells by binding to the VH region with low affinity," *J. Immunol.*, 161:1257-1266, 1998.
Dorner et al., "Analysis of the frequency and pattern of somatic mutations within nonproductively rearranged human variable heavy chain genes," *J. Immunol.*, 158:2779-2789, 1997.
Dörner et al., "Comparable impact of mutational and selective influences in shaping the expressed repertoire of peripheral IgM+/CD5− and IgM+/CD5+ B cells," *Eur. J. Immunol.*, 28:657-668, 1998.
Dörner et al., "Ig lambda and heavy chain gene usage in early untreated systemic lupus erythematosus suggests intensive B cell stimulation," *J. Immunol.*, 163:1027-1036, 1999.
Freedman et al., "Recommended standard of cerebrospinal fluid analysis in the diagnosis of multiple sclerosis: a consensus statement," *Arch. Neurol.*, 62:865-870, 2005.
Frohman and Martin, "Chapter 28: Detection of Homologous Recombinants," In: *PCR Protocols: A Guide to Methods and Applications*, Academic Press N. Y., pp. 228-236, 1990.
Hamblin et al., "Unmutated Ig V(H) genes are associated with a more aggressive form of chronic lymphocytic leukemia," *Blood*, 94:1848-1854, 1999.
Hansen et al., "Comparison of immunoglobulin heavy chain rearrangements between peripheral and glandular B cells in a patient with primary Sjogren's syndrome," *Scand. J. Immunol.*, 57:470-479, 2003.
Hansen et al., "Use of immunoglobulin variable-region genes by normal subjects and patients with systemic lupus erythematosus," *Int. Arch. Allergy Immunol.*, 123:36-45, 2000.
Harp et al., "Cerebrospinal fluid B cells from multiple sclerosis patients are subject to normal germinal center selection," *J. Neuroimmunol.*, 183:189-199, 2007.
Hayashi et al., "Biased usage of synovial immunoglobulin heavy chain variable region 4 by the anti-glucose-6-phosphate isomerase antibody in patients with rheumatoid arthritis," *Int. J. Mol. Med.*, 20:247-253, 2007.

(Continued)

*Primary Examiner* — Daniel E Kolker
*Assistant Examiner* — Stacey N MacFarlane
(74) *Attorney, Agent, or Firm* — Parker Highlander PLLC

(57) ABSTRACT

The present invention provides for the diagnosis and prediction of multiple sclerosis (MS) in subject utilizing a unique a codon signature in VH4 expressing B cells that has now been associated with MS and not with any other autoimmune disease.

29 Claims, 14 Drawing Sheets

PUBLICATIONS

Huang et al., "VH usage and somatic hypermutation in peripheral blood B cells of patients with rheumatoid arthritis (RA)," *Clin. Exp. Immunol.*, 112:516-527, 1998.

Humphries et al., "A new human immunoglobulin VH family preferentially rearranged in immature B-cell tumours," *Nature*, 331:446-449, 1988.

Kodaira et al., "Organization and evolution of variable region genes of the human immunoglobulin heavy chain," *J. Mol. Biol.*, 190:529-541, 1986.

Koelsch et al., "Mature B cells class switched to IgD are autoreactive in healthy individuals," *J. Clin. Invest.*, 117:1558-65, 2007.

Korteweg et al., "MRI criteria for dissemination in space in patients with clinically isolated syndromes: a multicentre follow-up study," *Lancet. Neurol.*, 5:221-227, 2006.

Lambracht-Washington et al., "Antigen specificity of clonally expanded and receptor edited cerebrospinal fluid B cells from patients with relapsing remitting MS," *J. Neuroimmunol.*, 186:164-76, 2007.

Lee et al., "A novel family of variable region genes of the human immunoglobulin heavy chain," *J. Mol. Biol.*, 195:761-768, 1987.

Meffre et al., "Circulating human B cells that express surrogate light chains and edited receptors," *Nat. Immunol.*, 1:207-213, 2000.

Mockridge et al., "Common patterns of B cell perturbation and expanded V4-34 immunoglobulin gene usage in autoimmunity and infection," *Autoimmunity*, 37:9-15, 2004.

Monson et al., "Receptor revision and atypical mutational characteristics in clonally expanded B cells from the cerebrospinal fluid of recently diagnosed multiple sclerosis patients," *J. Neuroimmunol.*, 158:170-181, 2005.

Oppezzo et al., "Somatic mutations can lead to a loss of superantigenic and polyreactive binding," *Eur. J. Immunol.*, 34:1423-1432, 2004.

Owens at al., "Restricted use of VH4 germline segments in an acute multiple sclerosis brain," *Ann. Neurol.*, 43:236-243, 1998.

Owens et al., "Single-cell repertoire analysis demonstrates that clonal expansion is a prominent feature of the B cell response in multiple sclerosis cerebrospinal fluid," *J. Immunol.*, 171:2725-2733, 2003.

Owens et al., "The immunoglobulin G heavy chain repertoire in multiple sclerosis plaques is distinct from the heavy chain repertoire in peripheral blood lymphocytes," *Clin. Immunol.*, 98:258-263, 2001.

Owens at al., "VH4 gene segments dominate the intrathecal humoral immune response in multiple sclerosis," *J. Immunol.*, 179:6343-6351, 2007.

Paolino et al., "A prospective study on the predictive value of CSF oligoclonal bands and MRI in acute isolated neurological syndromes for subsequent progression to multiple sclerosis," *J. Neurol. Neurosurg. Psychiatry*, 60:572-575, 1996.

Pascual and Capra, "VH4-21, a human VH gene segment overrepresented in the autoimmune repertoire," *Arthritis Rheum.*, 35:11-18, 1992.

Pugh-Bernard et al., "Regulation of inherently autoreactive VH4-34 B cells in the maintenance of human B cell tolerance," *J. Clin. Invest.*, 108:1061-1070, 2001.

Qin et al., "Clonal expansion and somatic hypermutation of V(H) genes of B cells from cerebrospinal fluid in multiple sclerosis," *J. Clin. Invest.*, 102:1045-1050, 1998.

Qin et al., "Intrathecal B-cell clonal expansion, an early sign of humoral immunity, in the cerebrospinal fluid of patients with clinically isolated syndrome suggestive of multiple sclerosis," *Lab. Invest.*, 83:1081-8, 2003.

Riemer and Jensen-Jarolim, "Mimotype vaccines: epitope mimics induce anti-cancer antibodies," *Immunol. Lett.*, 113:1-5, 2007.

Ritchie et al., "Comparative analysis of the CD19+ and CD138+ cell antibody repertoires in the cerebrospinal fluid of patients with multiple sclerosis," *J. Immunol.*, 173:640-656, 2004.

Rogozin and Diaz, "Cutting edge: DGYW/WRCH is a better predictor of mutability at G:C bases in Ig hypermutation than the widely accepted RRGY/WRCY motif and probably reflects a two-step activation-induced cytidine deaminase-triggered process," *J. Immunol.*, 172:3382-3384, 2004.

Shen et al., "Human heavy-chain variable region gene family nonrandomly rearranged in familial chronic lymphocytic leukemia," *Proc. Natl. Acad. Sci. USA*, 84:8563-8567, 1987.

Soderstrom et al., "Optic neuritis: prognosis for multiple sclerosis from MRI, CSF, and HLA findings," *Neurology*, 50:708-714, 1998.

Souza et al., "Influence of EBV on the peripheral blood memory B cell compartment," *J. Immunol.*, 179:3153-3160, 2007.

Tian et al., "Evidence for preferential Ig gene usage and differential TdT and exonuclease activities in human naïve and memory B cells," *Mol. Immunol.*, 44:2173-2183, 2007.

Voswinkel et al., "Evidence for a selected humoral immune response encoded by VH4 family genes in the synovial membrane of a patient with RA," *Ann. NY Acad Sci.*, 815:312-315, 1997.

Wardemann et al., "Predominant autoantibody production by early human B cell precursors," *Science*, 301:1374-1377, 2003.

Winges et al., "Analysis of multiple sclerosis cerebrospinal fluid reveals a continuum of clonally related antibody-secreting cells that are predominantly plasma blasts," *J. Neuroimmunol.*, 192:226-234, 2007.

Zheng et al., "Human immunoglobulin selection associated with class switch and possible tolerogenic origins for C delta class-switched B cells," *J. Clin. Invest.*, 113:1188-1201, 2004.

Brown et al., "Statistical methods for analyzing immunosignatures," *BMC Bioinformatics*, 12:349, 15 pp., 2011.

Onskog et al., "Classification of microarrays; synergistic effects between normalization, gene selection and machine learning," *BMC Bioinformatics*, 12:390, 19 pp., 2011.

Yang, "Biological applications of support vector machines," *Briefings in Bioinformatics*, 5(4):328-338, 2004.

Owens et al., "Antibodies produced by clonally expanded plasma cells in multiple sclerosis cerebrospinal fluid," *Ann Neurol.*, 65(6):639-649, (2009).

Whiting et al., "Accuracy of magnetic resonance imaging for the diagnosis of multiple sclerosis: systematic review." *BMJ*, 332:875, 2006.

\* cited by examiner

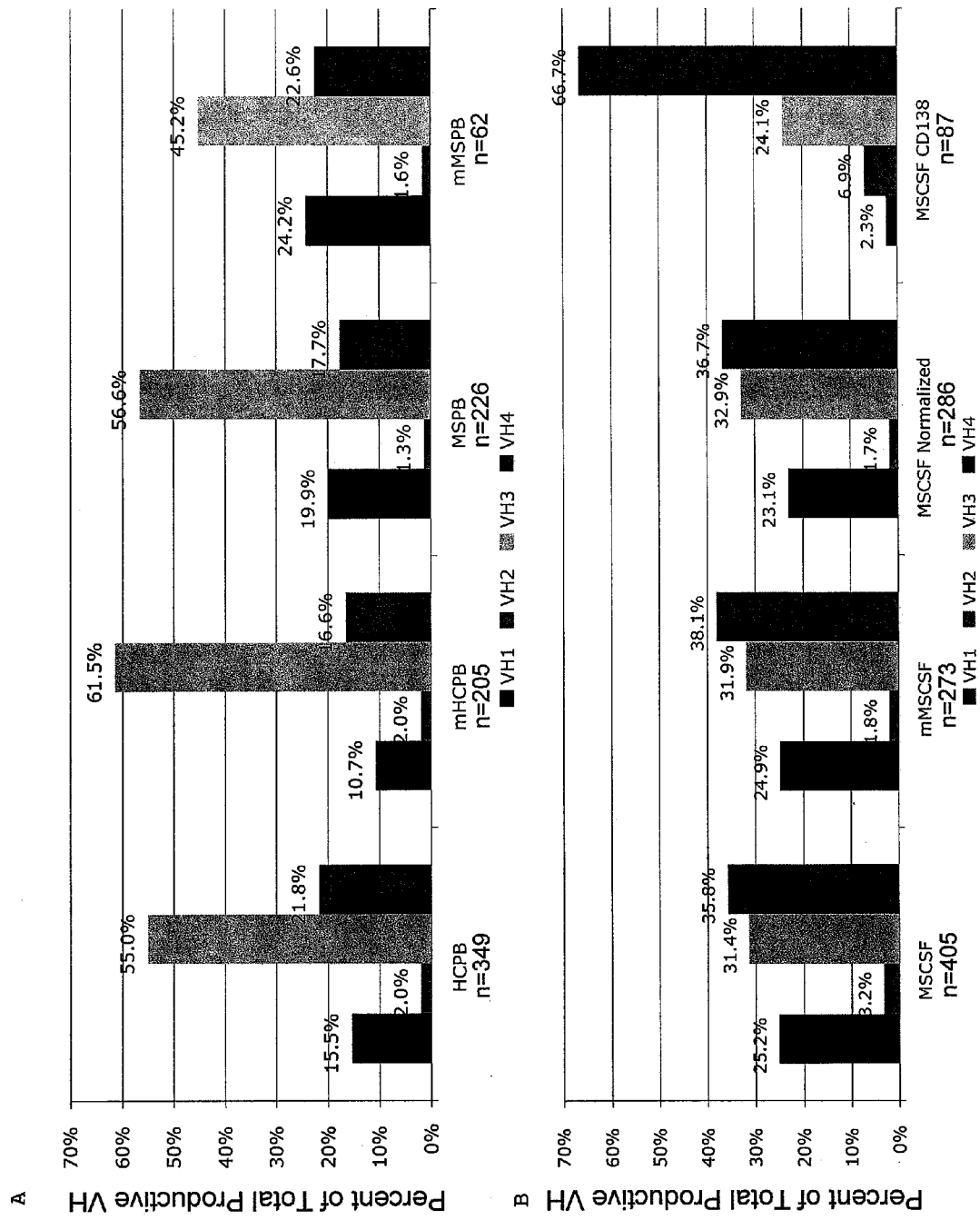
FIG. 1A-B

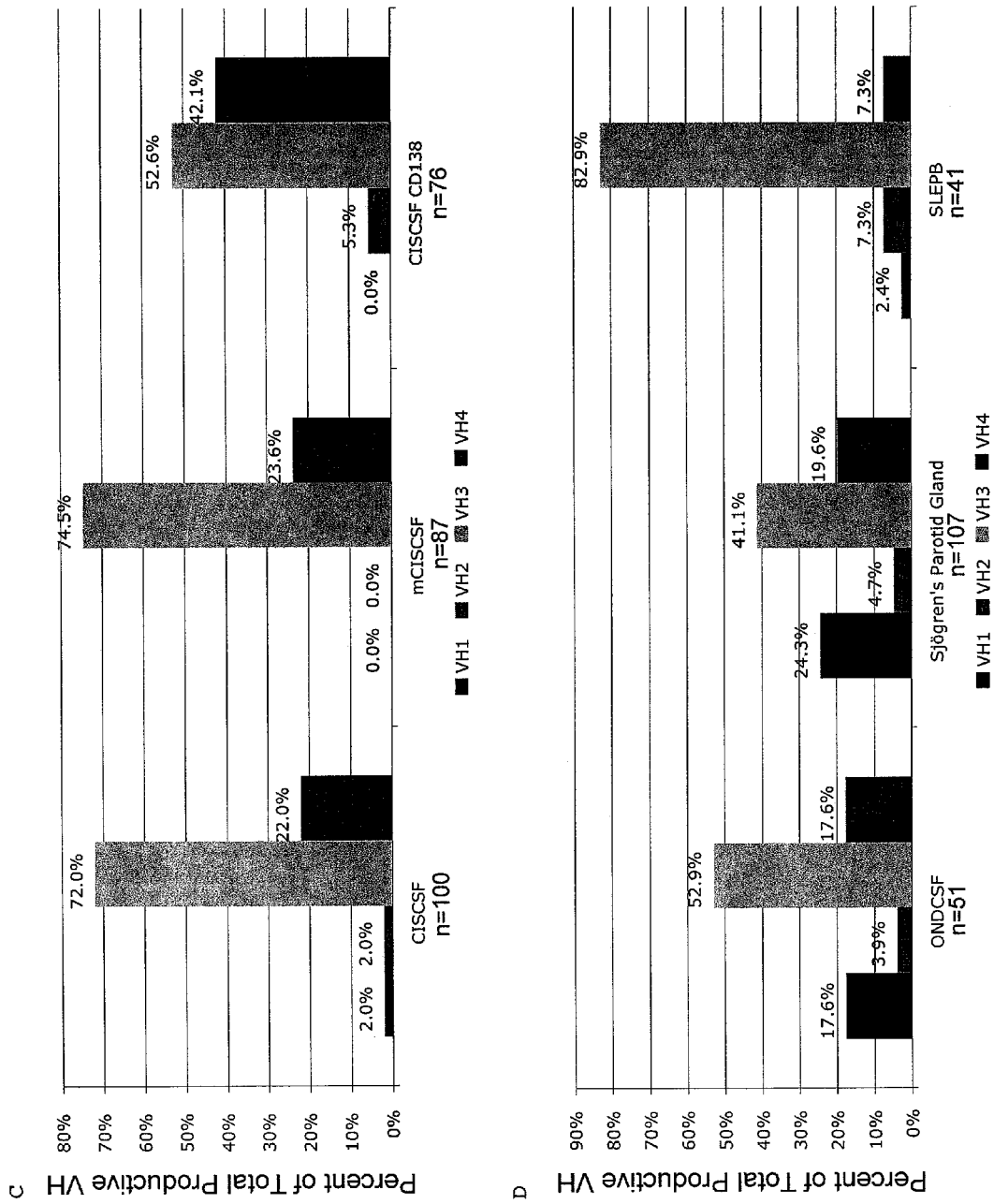
FIG. 1C-D

FIG. 3A-B

| | 1 2 3 | 4 5 6 7 | 8 9 10 | 11 12 13 | 14 15 16 17 |
|---|---|---|---|---|---|
| CON | CAGGTGCAGC | TGCAGGAGTC | GGGCCCAGGA | CTGGTGAAGC | CTTCGGAGAC |
| IGHV4-30-2*01 | CAGCTGCAGC | TGCAGGAGTC | CGGCTCAGGA | CTGGTGAAGC | CTTCACAGAC |
| IGHV4-30-4*01 | CAGGTGCAGC | TGCAGGAGTC | GGGCCCAGGA | CTGGTGAAGC | CTTCACAGAC |
| IGHV4-31*01 | CAGGTGCAGC | TGCAGGAGTC | GGGCCCAGGA | CTGGTGAAGC | CTTCACAGAC |
| IGHV4-34*01 | CAGGTGCAGC | TACAGCAGTG | GGGCGCAGGA | CTGTTGAAGC | CTTCGGAGAC |
| IGHV4-39*01 | CAGCTGCAGC | TGCAGGAGTC | GGGCCCAGGA | CTGGTGAAGC | CTTCGGAGAC |
| IGHV4-4*01 | CAGGTGCAGC | TGCAGGAGTC | GGGCCCAGGA | CTGGTGAAGC | CTCCGGGGAC |
| IGHV4-59*01 | CAGGTGCAGC | TGCAGGAGTC | GGGCCCAGGA | CTGGTGAAGC | CTTCGGAGAC |
| IGHV4-61*01 | CAGGTGCAGC | TGCAGGAGTC | GGGCCCAGGA | CTGGTGAAGC | CTTCGGAGAC |
| IGHV4-b*01 | CAGGTGCAGC | TGCAGGAGTC | GGGCCCAGGA | CTGGTGAAGC | CTTCGGAGAC |

| | 18 19 20 | 21 22 23 | 24 25 26 27 | 28 29 30 | 31 31a 31b |
|---|---|---|---|---|---|
| CON | CCTGTCCCTC | ACCTGCACTG | TCTCTGGTGG | CTCCATCAGC | AGTGGTGGTT |
| IGHV4-30-2*01 | CCTGTCCCTC | ACCTGCGCTG | TCTCTGGTGG | CTCCATCAGC | AGTGGTGGTT |
| IGHV4-30-4*01 | CCTGTCCCTC | ACCTGCACTG | TCTCTGGTGG | CTCCATCAGC | AGTGGTGATT |
| IGHV4-31*01 | CCTGTCCCTC | ACCTGCACTG | TCTCTGGTGG | CTCCATCAGC | AGTGGTGGTT |
| IGHV4-34*01 | CCTGTCCCTC | ACCTGCGCTG | TCTATGGTGG | GTCCTTCAGT | GGT-----T |
| IGHV4-39*01 | CCTGTCCCTC | ACCTGCGCTG | TCTCTGGTGG | CTCCATCAGC | AGTAGTAGTT |
| IGHV4-4*01 | CCTGTCCCTC | ACCTGCGCTG | TCTCTGGTGG | CTCCATCAGC | AGTAGT---A |
| IGHV4-59*01 | CCTGTCCCTC | ACCTGCACTG | TCTCTGGTGG | CTCCATCAGT | AGT-----T |
| IGHV4-61*01 | CCTGTCCCTC | ACCTGCACTG | TCTCTGGTGG | CTCCGTCAGC | AGTGGTAGTT |
| IGHV4-b*01 | CCTGTCCCTC | ACCTGCGCTG | TCTCTGGTTA | CTCCATCAGC | AGTGGT---T |

| | 32 33 34 35 | 36 37 38 | 39 40 41 | 42 43 44 45 | 46 47 48 |
|---|---|---|---|---|---|
| CON | ACTACTGGAG | CTGGATCCGC | CAGCCCCCAG | GGAAGGGGCT | GGAGTGGATT |
| IGHV4-30-2*01 | ACTCCTGGAG | CTGGATCCGG | CAGCCACCAG | GGAAGGGCCT | GGAGTGGATT |
| IGHV4-30-4*01 | ACTACTGGAG | TTGGATCCGC | CAGCCCCCAG | GGAAGGGCCT | GGAGTGGATT |
| IGHV4-31*01 | ACTACTGGAG | CTGGATCCGC | CAGCACCCAG | GGAAGGGCCT | GGAGTGGATT |
| IGHV4-34*01 | ACTACTGGGG | CTGGATCCGC | CAGCCCCCAG | GGAAGGGGCT | GGAGTGGATT |
| IGHV4-39*01 | ACTACTGGGG | CTGGATCCGG | CAGCCCCCAG | GGAAGGGGCT | GGAGTGGATT |
| IGHV4-4*01 | ACTGGTGGAG | TTGGATCCGC | CAGCCCCCAG | GGAAGGGACT | GGAGTGGATT |
| IGHV4-59*01 | ACTACTGGAG | CTGGATCCGG | CAGCCCCCAG | GGAAGGGACT | GGAGTGGATT |
| IGHV4-61*01 | ACTACTGGAG | CTGGATCCGG | CAGCCCCCAG | GGAAGGGGCT | GGAGTGGATT |
| IGHV4-b*01 | ACTACTGGGG | CTGGATCCGG | CAGCCCCCAG | GGAAGGGGCT | GGAGTGGATT |

FIG. 7

| | 49 50 51 | 52 53 54 55 | 56 57 58 | 59 60 61 | 62 63 64 65 |
|---|---|---|---|---|---|
| CON | GGGTAYATCT | ATTACAGTGG | GAGCACCWAC | TACAACCCGT | CCCTCAAGAG |
| IGHV4-30-2*01 | GGGTACACTCT | ATCATAGTGG | GAGCACCTAC | TACAACCCGT | CCCTCAAGAG |
| IGHV4-30-4*01 | GGGTACATCT | ATTACAGTGG | GAGCACCTAC | TACAACCCGT | CCCTCAAGAG |
| IGHV4-31*01 | GGGTACATCT | ATTACAGTGG | GAGCACCTAC | TACAACCCGT | CCCTCAAGAG |
| IGHV4-34*01 | GGGGAAATCA | ATCATAGTGG | AAGCACCAAC | TACAACCCGT | CCCTCAAGAG |
| IGHV4-39*01 | GGGAGTATCT | ATTATAGTGG | GAGCACCTAC | TACAACCCGT | CCCTCAAGAG |
| IGHV4-4*01 | GGGGAAATCT | ATCATAGTGG | GAGCACCAAC | TACAACCCGT | CCCTCAAGAG |
| IGHV4-59*01 | GGGTATATCT | ATTACAGTGG | GAGCACCAAC | TACAACCCCT | CCCTCAAGAG |
| IGHV4-61*01 | GGGTATATCT | ATTACAGTGG | GAGCACCAAC | TACAACCCCT | CCCTCAAGAG |
| IGHV4-b*01 | GGGAGTATCT | ATCATAGTGG | GAGCACCTAC | TACAACCCGT | CCCTCAAGAG |

| | 66 67 68 | 69 70 71 | 72 73 74 75 | 76 77 78 | 79 80 81 |
|---|---|---|---|---|---|
| CON | TCGAGTCACC | ATATCAGTAG | ACACGTCCAA | GAACCAGTTC | TCCCTGAAGC |
| IGHV4-30-2*01 | TCGAGTCACC | ATATCAGTAG | ACAGGTCCAA | GAACCAGTTC | TCCCTGAAGC |
| IGHV4-30-4*01 | TCGAGTTACC | ATATCAGTAG | ACACGTCCAA | GAACCAGTTC | TCCCTGAAGC |
| IGHV4-31*01 | TCTAGTTACC | ATATCAGTAG | ACACGTCTAA | GAACCAGTTC | TCCCTGAAGC |
| IGHV4-34*01 | TCGAGTCACC | ATATCAGTAG | ACACGTCCAA | GAACCAGTTC | TCCCTGAAGC |
| IGHV4-39*01 | TCGAGTCACC | ATATCAGTAG | ACAAGTCCAA | GAACCAGTTC | TCCCTGAAGC |
| IGHV4-4*01 | TCGAGTCACC | ATATCCGTAG | ACACGTCCAA | GAACCAGTTC | TCCCTGAAGC |
| IGHV4-59*01 | TCGAGTCACC | ATATCAGTAG | ACACGTCCAA | GAACCAGTTC | TCCCTGAAGC |
| IGHV4-61*01 | TCGAGTCACC | ATATCAGTAG | ACACGTCCAA | GAACCAGTTC | TCCCTGAAGC |
| IGHV4-b*01 | TCGAGTCACC | ATATCAGTAG | ACACGTCCAA | GAACCAGTTC | TCCCTGAAGC |

| | 82 82a 82b 82c | 83 84 85 | 86 87 88 | 89 90 91 92 | 93 94 |
|---|---|---|---|---|---|
| CON | TGAGCTCTGT | GACCGCCGCG | GACACGGCCG | TGTATTACTG | TGCGAGAGA |
| IGHV4-30-2*01 | TGAGCTCTGT | GACCGCCGCG | GACACGGCCG | TGTATTACTG | TGCCAGAGA |
| IGHV4-30-4*01 | TGAGCTCTGT | GACTGCCGCA | GACACGGCCG | TGTATTACTG | TGCCAGAGA |
| IGHV4-31*01 | TGAGCTCTGT | GACTGCCGCG | GACACGGCCG | TGTATTACTG | TGCCAGAGA |
| IGHV4-34*01 | TGAGCTCTGT | GACCGCCGCG | GACACGGCTG | TGTATTACTG | TGCGAGAGG |
| IGHV4-39*01 | TGAGCTCTGT | GACCGCCGCA | GACACGGCTG | TGTATTACTG | TGCGAGACA |
| IGHV4-4*01 | TGAGCTCTGT | GACCGCCGCG | GACACGGCCG | TGTATTGCTG | TGCGAGAGA |
| IGHV4-59*01 | TGAGCTCTGT | GACCGCTGCG | GACACGGCCG | TGTATTACTG | TGCGAGAGA |
| IGHV4-61*01 | TGAGCTCTGT | GACCGCTGCG | GACACGGCCG | TGTATTACTG | TGCGAGAGA |
| IGHV4-b*01 | TGAGCTCTGT | GACCGCCGCA | GACACGGCCG | TGTATTACTG | TGCGAGA |

FIG. 7 CONT.

| Codon | | 24 | 25 | 26 | 27 | 28 | 29 | 30 | 31 | 31A | 31B | 32 | 33 | 34 | 35 | 36 | 37 |
|---|---|---|---|---|---|---|---|---|---|---|---|---|---|---|---|---|---|
| IgH4-30.4 | Germline DNA | GTC | TCT | GGT | GGC | TCC | ATC | AGC | AGT | GGT | GAT | TAC | TAC | TGG | AGT | TGG | ATC |
| | M125-391 DNA | GTC | TCT | GGT | GGC | TCC | ATC | AGC | AGT | GGT | GAT | TAC | CAC | TGG | AGT | TGG | ATC |
| | Germline Protein | V | S | G | G | S | I | S | S | G | D | Y | Y | W | S | W | I |
| | M125-391 Changes | | | | | | | | | | | | H | | | | |

| Codon | | 38 | 39 | 40 | 41 | 42 | 43 | 44 | 45 | 46 | 47 | 48 | 49 | 50 | 51 | 52 | 53 |
|---|---|---|---|---|---|---|---|---|---|---|---|---|---|---|---|---|---|
| IgH4-30.4 | Germline DNA | CGC | CAG | CCC | CCA | GGG | AAG | GGA | CTG | GAG | TGG | ATT | GGG | TAC | ATC | TAT | TAC |
| | M125-391 DNA | CGC | CAG | CCC | CCA | GGG | AAG | GGA | CTG | GAG | TGG | ATT | GGG | AAC | ATC | AAT | TAT |
| | Germline Protein | R | Q | P | P | G | K | G | L | E | W | I | G | Y | I | Y | Y |
| | M125-391 Changes | | | | | | | | | | | | | N | | N | |

| Codon | | 54 | 55 | 56 | 57 | 58 | 59 | 60 | 61 | 62 | 63 | 64 | 65 | 66 | 67 | 68 | 69 |
|---|---|---|---|---|---|---|---|---|---|---|---|---|---|---|---|---|---|
| IgH4-30.4 | Germline DNA | AGT | GGG | AGC | ACC | TAC | TAC | AAC | CCG | TCC | CTC | AAG | AGT | CGA | GTT | ACC | ATA |
| | M125-391 DNA | AAT | GGG | GGC | GCG | TAC | CAC | AAT | CCG | TCC | CTC | ACG | AAT | CGA | GTT | ATC | ATG |
| | Germline Protein | S | G | S | T | Y | Y | N | P | S | L | K | S | R | V | T | I |
| | M125-391 Changes | N | | G | A | | H | | | | | T | N | | | | M |

| Codon | | 70 | 71 | 72 | 73 | 74 | 75 | 76 | 77 | 78 | 79 | 80 | 81 | 82 | 82A | 82B | 82C |
|---|---|---|---|---|---|---|---|---|---|---|---|---|---|---|---|---|---|
| IgH4-30.4 | Germline DNA | TCA | GTA | GAC | ACG | TCC | AAG | AAC | CAG | TTC | TCC | CTG | AAG | CTG | AGC | TCT | GTG |
| | M125-391 DNA | TCA | GTA | GAC | ACG | TCC | AAG | AAT | CAC | TTC | TCC | CTG | AAA | CTG | ACC | TCT | GTG |
| | Germline Protein | S | V | D | T | S | K | N | Q | F | S | L | K | L | S | S | V |
| | M125-391 Changes | | | | | | | | H | | | | | | T | | |

| Codon | | 83 | 84 | 85 | 86 | 87 | 88 | 89 | 90 | 91 | 92 | 93 | 94 |
|---|---|---|---|---|---|---|---|---|---|---|---|---|---|
| IgH4-30.4 | Germline DNA | ACT | GCC | GCA | GAC | ACG | GCC | GTG | TAT | TAC | TGT | GCC | AGA |
| | M125-391 DNA | ACT | GCC | GCA | GAC | ACG | GCC | GTG | TAT | TAC | TGT | GCC | AGA |
| | Germline Protein | T | A | A | D | T | A | V | Y | Y | C | A | R |
| | M125-391 Changes | | | | | | | | | | | | |

FIG. 8

VH4 CODON SIGNATURE FOR MULTIPLE SCLEROSIS

This application claims benefit of priority to U.S. Provisional Application Ser. No. 61/083,429, filed Jul. 24, 2008, the entire contents of which are hereby incorporated by reference.

This invention was made with government support under grant no. NS 40993 awarded by the National Institutes of Health. The government has certain rights in the invention.

BACKGROUND OF THE INVENTION

1. Field of the Invention

The present invention relates to fields of pathology, immunology and molecular biology. More particularly, the present invention relates to a VH4 peptide signature in VH-expressing B cells that predicts and diagnoses multiple sclerosis.

2. Description of Related Art

B cells have historically been implicated in the pathogenesis of Multiple Sclerosis (MS) since elevated CNS immunoglobulins and oligoclonal bands were first described in MS patients in the 1940s (Kabat et al. 1950; Kabat et al., 1948). Additional evidence of B cell involvement in MS pathogenesis includes the presence of B cells in MS lesions (Raine et al., 1999), and presence of B cells trafficking into the CNS during lesion development (Esiri, 1977) that intensifies with disease duration (Ozawa et al., 1994). Furthermore, the ratio of B cells to monocytes is stable over the disease course, but those patients with a prevalence of B cells tend to have a more expeditious disease progression than those with monocyte predominance (Cepok et al., 2001). Antibodies in conjunction with complement have also been identified in MS lesions co-localized with disintegrating myelin, suggesting a potential causative role played by these immune elements in lesion development (Genain et al., 1999; Storch and Lassmann, 1997).

The inventor and others have shown that clonal expansion of B cells occurs in both cerebrospinal fluid (CSF) (Colombo et al., 2000; Monson et al., 2005; Owens et al., 2003; Qin et al., 1998; Ritchie et al., 2004) and lesion sites (Baranzini et al., 1999; Owens et al., 1998) of MS patients. Clones at different stages of affinity maturation can be found in the CSF, suggesting that expansion is local (Monson et al., 2005). This finding is further substantiated by evidence that both ectopic germinal centers (Magliozzi et al., 2004; Serafini et al., 2004; Uccelli et al., 2005) and centroblasts, specialized B cells only found in germinal centers (Corcione et al., 2004), can be detectable in the CNS of MS patients. Characterization of clonally expanded B cells from the CSF of MS patients (MSCSF) demonstrated that the antibodies these B cells express are often self-reactive towards antigens found in the brain (Qin et al., 1998; Lambracht-Washington et al., 2007).

Data from others have established that the VH4-expressing B cell population in particular harbors autoreactive B cells in both healthy controls (Koelsch et al., 2007) and patients with systemic lupus erythematosus (SLE) (Pugh-Bernard et al., 2001). For example, B cells utilizing the VH4-34 gene (formerly known as VH4-21) are often autoreactive towards sugars on blood cells and either undergo negative selection in the adult repertoire (Koelsch et al., 2007; Pascual and Capra, 1992), or class switch to the rare IgD isotype rather than IgG, presumably to dampen the response of these autoreactive cells in healthy individuals (Koelsch et al., 2007).

Autoreactive B cells from the CSF and brain lesions (i.e., CNS) of MS patients are not suppressed, but instead undergo extensive clonal expansion (Colombo et al., 2000; Monson et al., 2005; Owens et al., 2003; Qin et al., 1998; Ritchie et al., 2004; Owens et al., 1998; Lambracht-Washington et al., 2007; Harp et al., 2007; Owens et al., 2007). This observation may indicate that regulatory mechanisms in the CNS of these patients may be more flexible than they are in the periphery. However, the inventor's previous analysis of antibody repertoires from MS patient derived CSF B cells indicated that regulation of this population, as it relates to germinal center selection, is preserved (Harp et al., 2007). The exception to this finding is that some, but not all, individual clonal populations appear to be dysregulated, as evidenced by lack of mutational targeting (Monson et al., 2005). A number of independent laboratories have documented that VH4-expressing B cells are overrepresented in the CSF (Colombo et al., 2000; Monson et al., 2005; Owens et al., 2003; Qin et al., 1998; Ritchie et al., 2004) and brain lesions (Baranzini et al., 1999; Owens et al., 1998) of MS patients. This finding was inconspicuous, however, since clonally expanding and autoreactive B cells from the CSF of MS patients could be found utilizing variable genes from any of the heavy (and light) chain families (Buluwela and Rabbitts, 1988; Humphries et al., 1988; Kodaira et al. 1986; Lee et al., 1987; Shen et al., 1987).

SUMMARY OF THE INVENTION

Thus, in accordance with the present invention, there is provided a method for identifying a human subject having or at risk of developing multiple sclerosis (MS) comprising assessing the VH4 structure of a VH4-expressing B-cell from said subject, wherein the presence of a codon signature associated with MS identifies said subject as having or at risk of developing MS. The codon signature may comprise a mutation at codon 31B, 56 and/or 81, or mutations at each of 31B, 56 and 81. The codon signature may further comprise mutations at one or more of codons 32, 40, 52, 57, 60 and 89, such as mutations at each of codons 31B, 32, 40, 56, 57, 60, 81 and 89. The codon signature may comprise a mutation at codons 31B, 40, 56, 57, 81 and/or 89, such as a mutation at each of codons 31B, 40, 56, 57, 81 and 89.

The method may further comprise assessing one or more traditional MS risk factors. Assessing may comprise sequencing, and may comprises PCR. The B-cell is obtained from cerebrospinal fluid (CSF), and the method may further comprise assessing J chain usage, J chain length, and/or CDR3 length. The B-cell may be obtained from peripheral blood, and the method may further comprise assessing J chain usage, J chain length, and/or CDR3 length. The method may also further comprise making a treatment decision based on the presence of said codon signature.

In another embodiment, there is provided a method of screening for an agent useful in treating multiple sclerosis (MS) comprising (a) providing an antibody produced by a VH4-expressing B-cell, said antibody comprising mutations at three or more codons selected from the group consisting of 31B, 32, 40, 56, 57, 60, 81 and 89; (b) contacting said antibody with a candidate ligand; and (c) assessing binding of said candidate ligand to said antibody, wherein binding of said candidate ligand to said antibody identifies said candidate ligand as useful in treating MS.

In yet another embodiment, there is provided a method of treating a subject having or at risk of developing MS comprising administering to said subject a ligand that binds to an antibody VH-4 antibody comprising mutations at three or more codons selected from the group consisting of 31B, 32, 40, 56, 57, 60, 81 and 89. The ligand may a peptide or a peptoid, and may be linked to a toxin or B-cell antagonist.

It is contemplated that any method or composition described herein can be implemented with respect to any other method or composition described herein.

The use of the word "a" or "an" when used in conjunction with the term "comprising" in the claims and/or the specification may mean "one," but it is also consistent with the meaning of "one or more," "at least one," and "one or more than one."

These, and other, embodiments of the invention will be better appreciated and understood when considered in conjunction with the following description and the accompanying drawings. It should be understood, however, that the following description, while indicating various embodiments of the invention and numerous specific details thereof, is given by way of illustration and not of limitation. Many substitutions, modifications, additions and/or rearrangements may be made within the scope of the invention without departing from the spirit thereof, and the invention includes all such substitutions, modifications, additions and/or rearrangements.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIGS. 1A-D. Frequency of VH family usage in productive B cell rearrangements. CD19+ B cells isolated from PB and CSF of (FIG. 1A) healthy control peripheral blood (HCPB) (n=2) and multiple sclerosis patient peripheral blood (MSPB) (n=3), (FIG. 1B) multiple sclerosis cerebrospinal fluid (MSCSF), memory cells of MSCSF (mMSCSF), MSCSF normalized for clonal representation, and MSCSF CD138+ plasma cells (all n=13), (FIG. 1C) clinically isolated syndrome cerebrospinal fluid (CISCSF) (n=3), memory cells of CISCSF (mCISCSF) (n=3), and MSCSF CD138 cells (n=1), and (FIG. 1D) other neurological disease cerebrospinal fluid (ONDCSF) (n=2), cells from the inflamed region of the parotid gland of a Sjögren's syndrome patient (n=1), systemic lupus erythematosus peripheral blood (SLEPB) (n=1). Data statistics can be found in Tables 9-12. The "n" number designated in each panel is the number of productive VH sequences used in each group; the "n" number in the legend is the number of patients in each group.

(FIG. 3A) The average amino acid length of the CDR3 region. (FIG. 3B) Percentage of productive VH4 sequences in each range of CDR3 amino acid lengths. The number of patients included in each group can be found in the FIGS. 1A-D legend; the number of VH4 productive sequences used for analysis in each group is shown in the figure. Data statistics can be found in Table 15 for FIG. 3A and Table 16 for FIG. 3B.

FIG. 7. Comparison of sequence for VH4 genes, including a consensus. Individual genes are listed at the left hand side; "C" stand for consensus.

FIG. 8. Example of VH4 comparison. A VH4-30.4 sequence is listed as the germline configuration (allele 01) and compared to a patient CD19+ B cell sequence. The germline protein conversion and the changes made by replacement mutations in the patient sequence are noted. Signature codons are boxed, with the dashed boxes demarcating cold spots, and the solid boxes demarcating hot spots. CDRs as defined by Kabat (Kabat et al., 1983) are shaded.

DESCRIPTION OF ILLUSTRATIVE EMBODIMENTS

Figure 2:
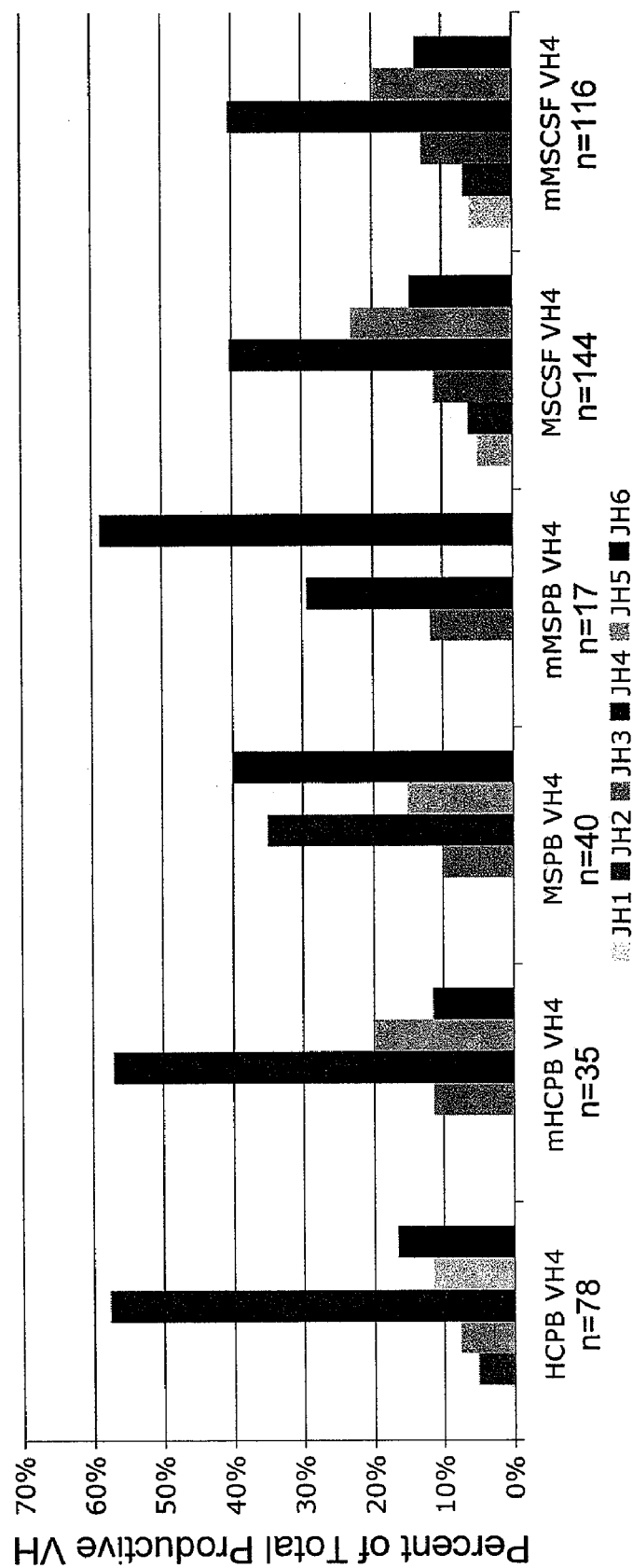
FIG. 2. Frequency of J segment usage in productive VH4 B cell rearrangements. CD19+ B cells expressing a productive VH4 rearrangement were isolated from HCPB, MSPB, and MSCSF and analyzed for J segment usage. The number of patients included in each group can be found in the FIGS. 1A-D legend; the number of productive VH4 sequences in each group is shown in the figure. Data statistics can be found in Table 13. The overall repertoire J segment usages can be found in FIG. 6, with statistics in Supplemental Table 8.

Since 1998, a number of independent laboratories have documented that VH4-expressing B cells are overrepresented in the CSF (Colombo et al., 2000; Monson et al., 2005; Owens et al., 2003; Qin et al., 1998; Ritchie et al., 2004) and brain lesions (Baranzini et al., 1999; Owens et al., 1998) of MS patients. This finding was initially inconspicuous since clonally expanding and autoreactive B cells from the CSF of MS patients could be found utilizing variable genes from any of the heavy (and light) chain families (Buluwela and Rabbitts, 1988; Humphries et al., 1988; Kodaira et al. 1986; Lee et al., 1987; Shen et al., 1987). However, emerging evidence that the VH4-expressing B cell population harbors autoreactive B cells (Koelsch et al., 2007), combined with the established observation that VH4-expressing B cells are overrepresented in CNS-derived B cell populations from MS patients (Colombo et al., 2000; Owens et al., 2003; Qin et al., 1998; Ritchie et al., 2004; Baranzini et al., 1999; Owens et al., 1998; Harp et al., 2007; Owens et al., 2007), prompted us to question the role of VH4-expressing B cells in the CSF of MS patients.

To address this issue, the inventor compared repertoire characteristics from their database of 405 CSF-derived B cells from 13 MS patients to that of healthy controls as well as to several other B cell mediated autoimmune diseases or other CNS-related disorders. The inventor predicted that VH4-expressing B cells from the CSF of MS patients could be enriched for features associated with autoreactivity since (i) VH4 expressing B cells from patients with autoimmune diseases (including SLE and RA) are enriched for autoreactivity (Pugh-Bernard et al., 2001; Zheng et al., 2004; Mockridge et al., 2004; Voswinkel et al., 1997; Hayashi et al., 2007; Huang et al., 1998), and (ii) some autoreactive, clonally-expanded CSF-derived B cells from MS patients use VH4 in their antibody rearrangements (Lambracht-Washington et al., 2007). Features that we were particularly interested in were those known to be associated with autoreactivity including bias towards VH4-34 usage (Zheng et al., 2004) and features associated with receptor editing including bias in JH6 usage and long CDR3 lengths (Zheng et al., 2004; Meffre et al., 2000). Diminished mutational frequency has been associated with receptor editing (Meffre et al., 2000), and diminished mutation targeting has been associated with clonally expanded CSF derived B cell populations in MS patients (Monson et al., 2005) and thus were also included in the analyses.

In order to perform this VH4-specific analysis, the inventor constructed an extensive CSF B cell database containing 405 CSF-derived B cells from 13 MS patients. Overrepresentation of VH4-expressing CD19+ B cells in the CSF of MS patients was unique since VH4 overrepresentation was not observed in B cell repertoires from the peripheral blood of (i) healthy control donors, (ii) patients with other autoimmune diseases with B cell involvement, including systemic lupus erythematosis (SLE) or Sjögren's syndrome, or (iii) MS patients from the same cohort. In fact, in depth analysis of those VH4-expressing B cells from the peripheral blood of MS patients within this cohort indicated that this group of B cells was likely recognized for their autoreactive potential (as evidenced by high JH6 usage and long CDR3 length), and were denied further selection (as evidenced by low mutational frequencies). The inventor also did not observe over-representation of VH4-expressing B cells in the CSF of patients with other neurological diseases, indicating that over-representation of VH4 expressing B cells in the CSF of MS patients is not due to bias in the ability of VH4 expressing B cells to enter the CNS. Taken together, these data suggest that VH4 expressing B cells are selected into the CSF B cell repertoire of MS patients in particular, and is further validated by the high mutational frequencies and punctuated mutational targeting observed in this population.

Of the three CIS patients included in this comparison study, even those that convert to CDMS within the next year (CIS429 and CIS03-01) did not have the overrepresentation of VH4 family usage in their CSF-derived CD19+ B cell population. In contrast, evidence of VH4 overrepresentation is observed in the CD138+ plasma cells from CIS03-01. Since the plasma cells and plasma blasts are most likely arising from the CD19+ B cell population (matching clones can be found in both compartments) (Martin Mdel and Monson, 2007), it is reasonable to hypothesize that VH4 expressing B cells which recognize their antigen in the CNS do not linger in the memory pool long, but are signaled to differentiate rapidly into plasma blasts and plasma cells. This hypothesis is also further substantiated by the lack of receptor editing in the VH4 expressing CSF-derived B cells from these patients (as assessed by normal JH6 usage and CDR3 length), as well as documentation that plasmablasts and plasma cells are highly enriched in the CSF of these patients (Cepok et al., 2005; Winges et al., 2007). Dysregulation of these VH4 cells at the initiation of disease processes may be a central component of ongoing pathogenesis.

The inventor expected the increase in VH4 family usage would correspond to an increase in particular VH4 genes used most frequently in MS lesions and in the clones found in MSCSF such as 4-34, 4-39 and 4-59 (Monson et al., 2005; Owens et al., 1998). However, usage frequency of individual VH4 genes within the VH4-expressing CSF B cell subdatabase was no different than in PB of any cohort the inventor analyzed with the exception of VH4-34, which was utilized more frequently in SLE and Sjögren's than in MSCSF. It is possible that B cells from the MS patients examined were responding to a variety of VH4-binding antigens, so that the combination of these made an increase in a single gene indeterminable. Another possibility is an antigen may bind to the VH4 genes and cause a superantigen response in only the B cells expressing VH4, similarly to what is seen with staphylococcal enterotoxin A with VH3-expressing B cells (Domiati-Saad and Lipsky, 1998). However, superantigen binding capacity is diminished with high mutation accumulation (Oppezzo et al., 2004), and so a classical superantigen response is unlikely. In contrast, EBV infected memory B cells tend to have high mutational frequencies and prevalent mutational targeting (Souza et al., 2007) similar to what we described in the MSCSF database presented here, but no mechanism of EBV infection susceptibility or immune response to the virus has been reported that favors VH4-expressing B cells over other heavy chain family expression. Nevertheless, the elevated mutational frequency observed in VH4-expressing B cells from the CSF of MS patients extends the inventor's previous hypothesis that CSF-derived B cells responding to antigen in the CNS are heavily driven within the CNS itself to suggest that much of this heightened activity is occurring within the VH4-expressing CSF-derived B cell populations. Whether these B cells are responding to self-antigens or valid foreign targets remains controversial. However, mutational analysis indicates that the VH4-expressing CSF-derived B cells from MS patients had gone through a typical germinal center, since mutational targeting to CDR and to DGYW/WRCH motifs is intact, unlike what has been observed in the individual clonal populations from MS patients in the cohort (Monson et al., 2005). In addition, targeting was actually increased in the MSCSFVH4 subdatabase, most likely because the number of rounds of somatic hypermutation the B cells had undergone in response to antigen was extensive (evidenced by the high mutation frequency). Defining the antigen specificity of highly mutated, VH4-expressing CSF-derived B cells from MS patients will be paramount to resolving the mechanism of this unique selection of VH4 expressing B cells in the CSF of MS patients.

Hyperintense mutation accumulation in the MSCSF database enabled the inventor to identify a unique 5 codon signature of VH4 replacement mutations—codons 31B, 40, 57, 60 and 69—that was not observed in the control databases. Of these 5 codons, 31B was particularly interesting because it accumulated replacement mutations at a rate 7-fold higher than expected, suggesting that this codon plays a pivotal role in antigen-antibody interactions. It is possible that myelin basic protein (MBP) may be excluded from this list of possible antigens interacting with this unique antibody signature since one of the clonally expanded CSF-derived B cells strongly reactive to MBP (Lambracht-Washington et al., 2007) utilized a VH4-59 gene, which does not contain codon 31B. Also, since other databases in this analyses rarely (if ever) accumulated mutations in this position (0.17% in HCPB), it is likely that the antigen targets of VH4 expressing CSF-derived B cells from MS patients are not seen to a great extent in peripheral blood from healthy donors.

Figure 5A:
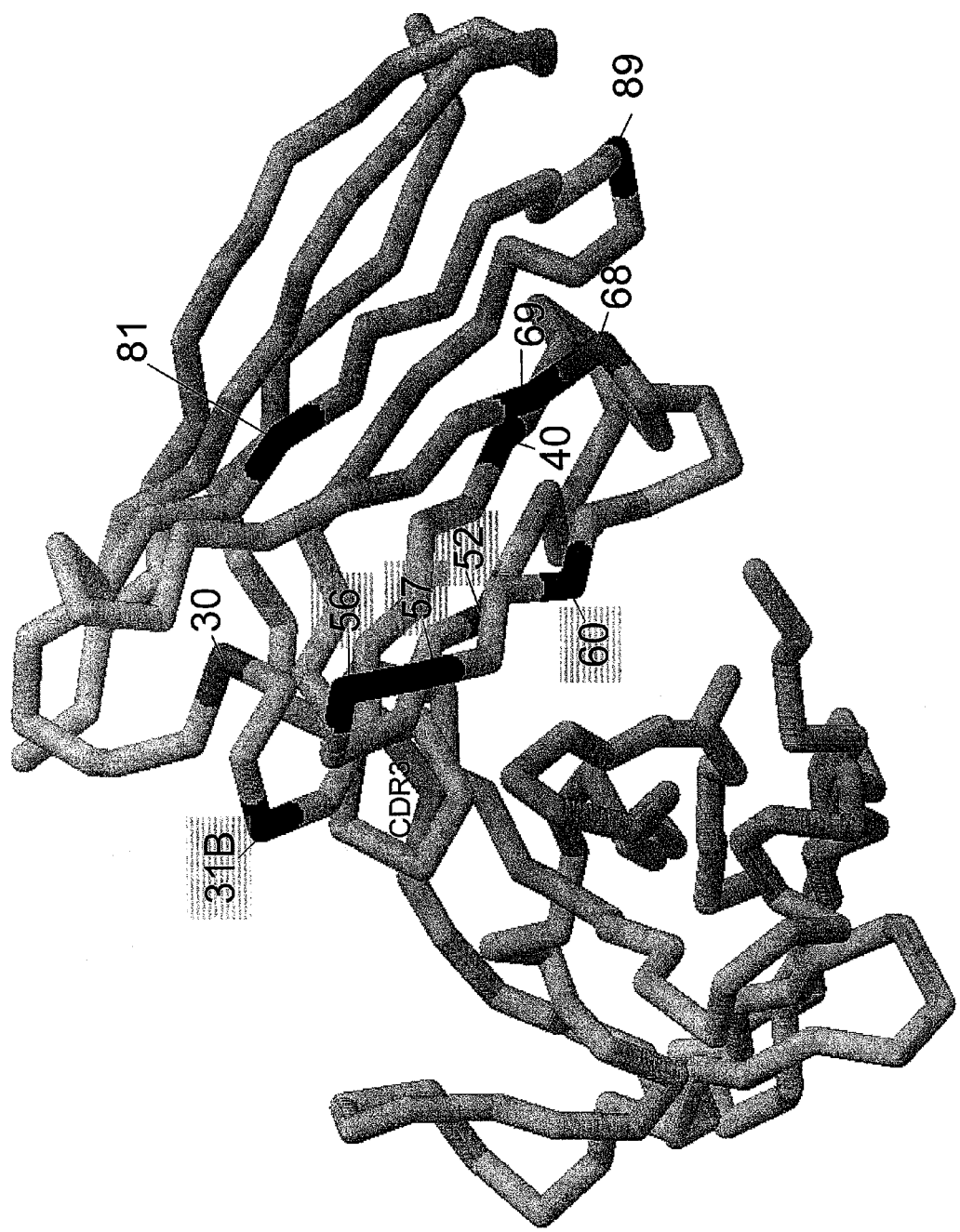
FIGS. 5A-B. Model of VH4 structure. VH4-30.4 antibody structure was adapted from (Guddat et al., 1993) as described in the Materials & Methods. The light chain variable domain is included for reference and is encoded in gray, while the heavy chain backbone is in yellow. The VH4 signature has been demarcated, with "hot" spots in blue (residues 31B, 40, 56, 57, 60, 69, 81, and 89; corresponds to FIG. 7), and "cold" spots in green (residues 30, 52, and 68; corresponds to FIG. 7). Those hot or cold spots contained within a CDR have been highlighted. The CDR3 is that of the original structure, and not from any VH4 discussed here.
Figure 5B:
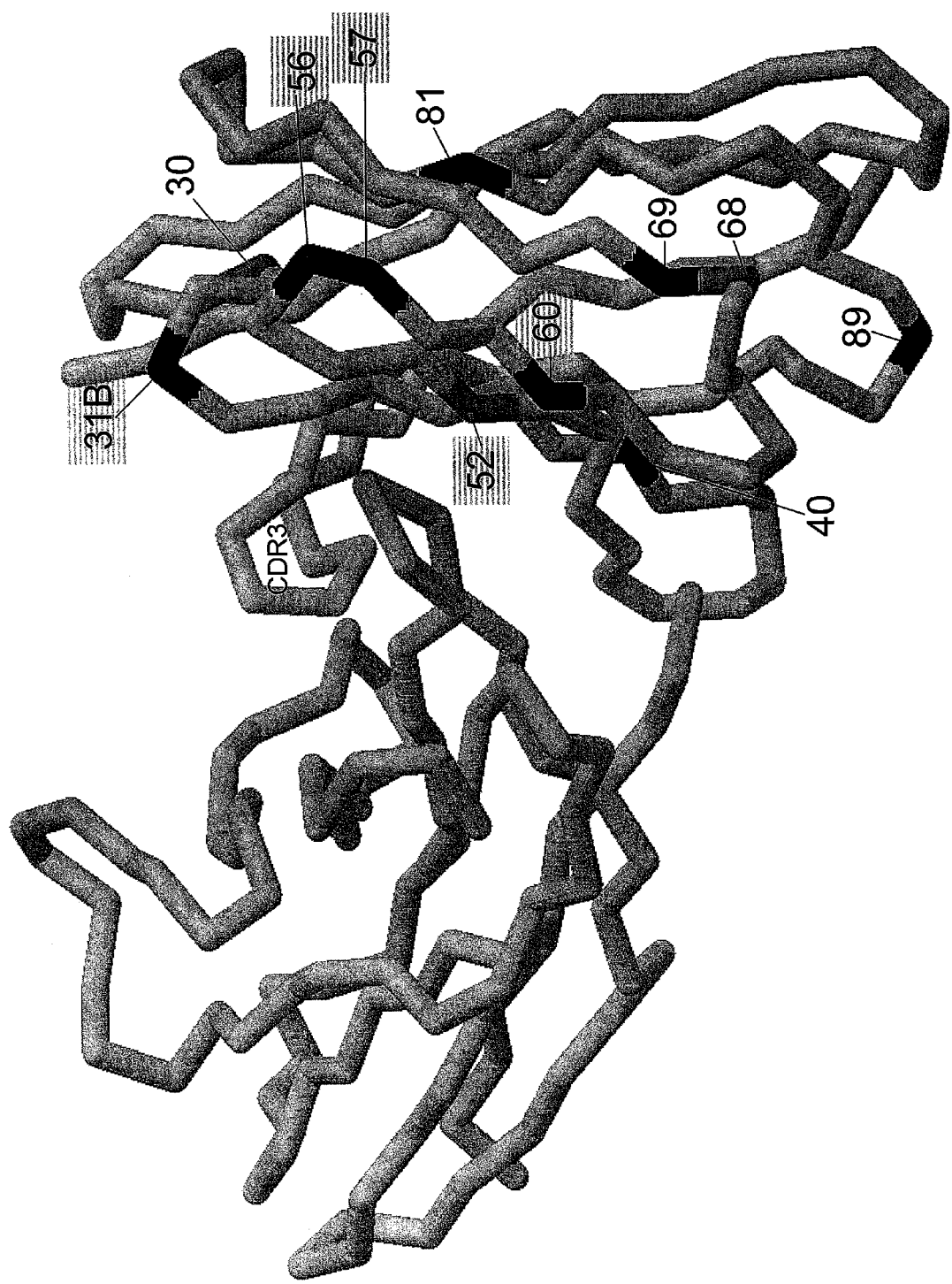

Codon composition can also influence the protein structure of antibody variable regions (Chothia et al., 1992). VH4-34 and 4-59 have a similar structure, as they have neither codons 31A or 31B; VH4-04, 4-B, and 4-28 have only codon 31A; and the 4-30 sub-genes, 4-39, 4-61, and 4-31 have both codons 31A and 31B. FIG. 7. In addition, several crucial codons are needed to maintain structure; none of the VH4 signature codons are key residues that would change the structure of the antibody (Chothia et al., 1992; Chothia and Lesk, 1987). This infers that genes of similar structure have similar antigen-binding sites, though the exact placement may differ due to the size, hydrophilicity, and polarity of surrounding residues. By the method designated by Clothia et al. (1992), CDR1 is comprised of residues 26 through 32 because these are outside the framework β-sheets and form a loop involved in the antigen binding pocket, and CDR2 is only residues 50 through 58; this translates into codon 30, 31B, 52, 56, and 57 are all in direct contact with the antigen (FIG. 5), while 60 is between the antigen binding pocket and another surface loop not directly involved with antigen binding (Chothia et al., 1992). Therefore, codons 30 and 52 are likely "cold," to maintain efficient antibody interaction with the antigen, while variation in codons 31B (in the few genes it is in), 56, and 57 provide more effective binding to their antigen with different size, hydrophilicity, or polarity properties. It is less clear why residues 40, 69, 81, and 89 are "hot" or residue 68 is "cold," and how replacement mutations at these positions affect VH4 antigen binding (FIG. 5). Investigating the impact of replacement mutations at these positions will provide important clues regarding the interaction of these VH4 utilizing antibodies with self-antigens in the CNS.

It is also likely that different combinations of residue replacements affect binding to discreet antigens. For example, perhaps the combination of replacements at codons A, B and C mediate high affinity binding to antigen X, while replacements at codons BDE mediate high affinity binding to antigen Y. This would explain the differences in replacement mutation positions in different VH4 genes; codon positions ABC are needed for 4-31 to bind antigen X, while codon positions BDE are needed for 4-39 to bind antigen Y. In support of this, the inventor found that different VH4 genes do selectively use the MS signature mutations at varying levels; for example, VH4-30 has more mutations in codons 56 and 81, while VH4-39 tends to accumulate mutations more rapidly in codons 31B, 50, 56, and 81 (Table 6).

In summary, VH4 family usage is substantially increased in both CD19+ B cells and CD138+ plasma cells isolated from the central nervous system of MS patients, (FIG. 1 and (Owens et al., 2007)), but as shown here, not in healthy controls, patients with other CNS-related diseases, or patients with other B cell related autoimmune diseases. The VH4 overexpression seen in the MS patients is due to changes in use of many of the genes in the VH4 family (rather than VH4-34 alone), and mutational analysis suggests that antigen-driven selection in the context of classical germinal centers is preserved. Thus, the VH4 expressing B cells from the CSF of MS patients are not dysregulated at this level of selection. More importantly, a unique 11 codon footprint of mutational characteristics can be found in the MSCSF VH4 subdatabase that is not observed in healthy control peripheral blood or CSF-derived B cells from patients with other neurological diseases. This signature, which accumulates replacement mutations up to 7-fold more frequently than in healthy control PB-derived B cells, is most likely a combination of sub-signatures that mediate effective binding to antigens present in the CNS. The inventor now proposes the use of this signature to predict or diagnose MS in subjects.

I. VH4

The normal immune system has the ability to generate millions of antibodies with different antigen binding abilities. The diversity is brought about by the complexities of constructing immunoglobulin molecules. These molecules consist of paired polypeptide chains (heavy and light) each containing a constant and a variable region. The structures of the variable regions of the heavy and light chains are specified by immunoglobulin V genes. The heavy chain variable region is derived from three gene segments known as VH, D and JH. In humans there are about 100 different VH segments, over 20 D segments and six JH segments. The light chain genes have only two segments, the VL and JL segments. Antibody diversity is the result of random combinations of VH/D/JH segments with VUJL components superimposed on which are several mechanisms including junctional diversity and somatic mutation.

The germline VH genes can be separated into at least six families (VH1 through VH6) based on DNA nucleotide sequence identity of the first 95 to 101 amino acids. Members of the same family typically have ≧80% sequence identity, whereas members of different families have less than 70% identity. These families range in size from one VH6 gene to an estimated greater than 45 VH3 genes. In addition, many pseudogenes exist. Recent studies have nearly completed a physical map of the VH locus on chromosome 14q32.13.15. It has now been estimated that the human VH repertoire is represented by approximately 50 functional VH segments with about an equal number of pseudogenes. These studies estimate the size of the VH locus to be approximately 1100 kb, which is less than half the previous estimates of 2.5 to 3 megabases as determined by pulse field gel electrophoresis. The VH4 family of genes contains 9 different members: 4-04, 4-28, 4-30, 4-31, 4-34, 4-39, 4-59, 4-61, 4-B4 (see FIG. 7).

The present invention relates to identification of a "signature" in the VH4 sequences of certain B cells. The sequence signature initially comprises residues 31B, 56 and/or 81, but also can include one or more of residues 30, 40, 52, 57, 60, 68, 69 and 89 (FIG. 7). By examining the sequence at these positions, and identifying mutations at one or more of the positions, it can be determined that a subject is at risk of developing MS and, in the presence of additional factors, has MS.

II. Nucleic Acids and Detection Methods Therefor

Another aspect of the present invention concerns isolated DNA segments and their use in detecting the presence of mutations in certain codons of the VH4 segments from a subject. Many methods described herein will involve the use of amplification primers, oligonucleotide probes, and other nucleic acid elements involved in the analysis of genomic DNA, cDNA or mRNA transcripts, such as SEQ ID NO:2, which is the germline or normal sequence of VH4 family genes.

The term "nucleic acid" is well known in the art. A "nucleic acid" as used herein will generally refer to a molecule (i.e., a strand) of DNA or RNA comprising a nucleobase. A nucleobase includes, for example, a naturally-occurring purine or pyrimidine base found in DNA (e.g., an adenine "A," a guanine "G," a thymine "T" or a cytosine "C") or RNA (e.g., an A, a G, an uracil "U" or a C). The term "nucleic acid" encompass the terms "oligonucleotide" and "polynucleotide," each as a subgenus of the term "nucleic acid." The term "oligonucleotide" refers to a molecule of between about 3 and about 100 nucleobases in length. The term "polynucleotide" refers to at least one molecule of greater than about 100 nucleobases in length. A "gene" refers to coding sequence of a gene product, as well as introns and the promoter of the gene product.

These definitions generally refer to a single-stranded molecule, but in specific embodiments will also encompass an additional strand that is partially, substantially or fully complementary to the single-stranded molecule. Thus, a nucleic acid may encompass a double-stranded molecule that comprises complementary strands or "complements" of a particular sequence comprising a molecule. In particular aspects, a nucleic acid encodes a protein or polypeptide, or a portion thereof.

A. Preparation of Nucleic Acids

A nucleic acid may be made by any technique known to one of ordinary skill in the art, such as for example, chemical synthesis, enzymatic production or biological production. Non-limiting examples of a synthetic nucleic acid (e.g., a synthetic oligonucleotide), include a nucleic acid made by in vitro chemical synthesis using phosphotriester, phosphite or phosphoramidite chemistry and solid phase techniques such as described in EP 266,032, incorporated herein by reference, or via deoxynucleoside H-phosphonate intermediates as described by Froehler et al., 1986 and U.S. Pat. No. 5,705, 629, each incorporated herein by reference. In the methods of the present invention, one or more oligonucleotide may be used. Various different mechanisms of oligonucleotide synthesis have been disclosed in for example, U.S. Pat. Nos. 4,659,774, 4,816,571, 5,141,813, 5,264,566, 4,959,463, 5,428,148, 5,554,744, 5,574,146, 5,602,244, each of which is incorporated herein by reference.

A non-limiting example of an enzymatically produced nucleic acid include one produced by enzymes in amplification reactions such as PCR™ (see for example, U.S. Pat. No. 4,683,202 and U.S. Pat. No. 4,682,195, each incorporated herein by reference), or the synthesis of an oligonucleotide described in U.S. Pat. No. 5,645,897, incorporated herein by reference. A non-limiting example of a biologically produced nucleic acid includes a recombinant nucleic acid produced (i.e., replicated) in a living cell, such as a recombinant DNA vector replicated in bacteria (see for example, Sambrook et al. 2001, incorporated herein by reference).

B. Purification of Nucleic Acids

A nucleic acid may be purified on polyacrylamide gels, cesium chloride centrifugation gradients, chromatography columns or by any other means known to one of ordinary skill in the art (see for example, Sambrook et al., 2001, incorporated herein by reference). In some aspects, a nucleic acid is a pharmacologically acceptable nucleic acid. Pharmacologically acceptable compositions are known to those of skill in the art, and are described herein.

In certain aspects, the present invention concerns a nucleic acid that is an isolated nucleic acid. As used herein, the term "isolated nucleic acid" refers to a nucleic acid molecule (e.g., an RNA or DNA molecule) that has been isolated free of, or is otherwise free of, the bulk of the total genomic and transcribed nucleic acids of one or more cells. In certain embodiments, "isolated nucleic acid" refers to a nucleic acid that has been isolated free of, or is otherwise free of, bulk of cellular components or in vitro reaction components such as for example, macromolecules such as lipids or proteins, small biological molecules, and the like.

C. Nucleic Acid Complements

As discussed above, the present invention encompasses a nucleic acid that is complementary to a nucleic acid. A nucleic acid is "complements" or is "complementary" to another nucleic acid when it is capable of base-pairing with another nucleic acid according to the standard Watson-Crick, Hoogsteen or reverse Hoogsteen binding complementarity rules. As used herein "another nucleic acid" may refer to a separate molecule or a spatial separated sequence of the same molecule. In preferred embodiments, a complement is a hybridization probe or amplification primer for the detection of a nucleic acid polymorphism.

As used herein, the term "complementary" or "complement" also refers to a nucleic acid comprising a sequence of consecutive nucleobases or semiconsecutive nucleobases (e.g., one or more nucleobase moieties are not present in the molecule) capable of hybridizing to another nucleic acid strand or duplex even if less than all the nucleobases do not base pair with a counterpart nucleobase. However, in some diagnostic or detection embodiments, completely complementary nucleic acids are preferred.

D. Nucleic Acid Detection and Evaluation

Those in the art will readily recognize that nucleic acid molecules may be double-stranded molecules and that reference to a particular site on one strand refers, as well, to the corresponding site on a complementary strand. Thus, in defining a polymorphic site, reference to an adenine, a thymine (uridine), a cytosine, or a guanine at a particular site on the plus (sense or coding) strand of a nucleic acid molecule is also intended to include the thymine (uridine), adenine, guanine, or cytosine (respectively) at the corresponding site on a minus (antisense or noncoding) strand of a complementary strand of a nucleic acid molecule. Thus, reference may be made to either strand and still comprise the same polymorphic site and an oligonucleotide may be designed to hybridize to either strand. Throughout the text, in identifying a polymorphic site, reference is made to the sense strand, only for the purpose of convenience.

Typically, the nucleic acid mixture is isolated from a biological sample taken from the individual, such as a blood, fecal or tissue (e.g., intestinal mucosal) sample using standard techniques such as disclosed in Jones (1963) which is hereby incorporated by reference. Other suitable tissue samples include whole blood, saliva, tears, urine, sweat, buccal, skin and hair. The nucleic acid mixture may be comprised of genomic DNA, mRNA, or cDNA. Furthermore it will be understood by the skilled artisan that mRNA or cDNA preparations would not be used to detect polymorphisms located in introns or in 5' and 3' non-transcribed regions.

The identity of a nucleotide (or nucleotide pair) at a polymorphic site may be determined by amplifying a target region(s) containing the polymorphic site(s) directly from one or both copies of the gene present in the individual and the sequence of the amplified region(s) determined by conventional methods. It will be readily appreciated by the skilled artisan that only one nucleotide will be detected at a polymorphic site in individuals who are homozygous at that site, while two different nucleotides will be detected if the individual is heterozygous for that site. The polymorphism may be identified directly, known as positive-type identification, or by inference, referred to as negative-type identification. For example, where a SNP is known to be guanine and cytosine in a reference population, a site may be positively determined to be either guanine or cytosine for an individual homozygous at that site, or both guanine and cytosine, if the individual is heterozygous at that site. Alternatively, the site may be negatively determined to be not guanine (and thus cytosine/cytosine) or not cytosine (and thus guanine/guanine).

The target region(s) may be amplified using any oligonucleotide-directed amplification method, including but not limited to polymerase chain reaction (PCR) (U.S. Pat. No. 4,965,188), ligase chain reaction (LCR) (Barany et al., 1991; WO90/01069), and oligonucleotide ligation assay (OLA) (Landegren et al., 1988). Oligonucleotides useful as primers or probes in such methods should specifically hybridize to a region of the nucleic acid that contains or is adjacent to the polymorphic site. Typically, the oligonucleotides are between 10 and 35 nucleotides in length and preferably, between 15 and 30 nucleotides in length. Most preferably, the oligonucleotides are 20 to 25 nucleotides long. The exact length of the oligonucleotide will depend on many factors that are routinely considered and practiced by the skilled artisan.

Other known nucleic acid amplification procedures may be used to amplify the target region including transcription-based amplification systems (U.S. Pat. No. 5,130,238; EP 329,822; U.S. Pat. No. 5,169,766, WO89/06700) and isothermal methods (Walker et al., 1992).

A polymorphism in the target region may also be assayed before or after amplification using one of several hybridization-based methods known in the art. Typically, allele-specific oligonucleotides are utilized in performing such methods. The allele-specific oligonucleotides may be used as differently labeled probe pairs, with one member of the pair showing a perfect match to one variant of a target sequence and the other member showing a perfect match to a different variant. In some embodiments, more than one polymorphic site may be detected at once using a set of allele-specific oligonucleotides or oligonucleotide pairs.

Hybridization of an allele-specific oligonucleotide to a target polynucleotide may be performed with both entities in solution, or such hybridization may be performed when either the oligonucleotide or the target polynucleotide is covalently or noncovalently affixed to a solid support. Attachment may be mediated, for example, by antibody-antigen interactions, poly-L-Lys, streptavidin or avidin-biotin, salt bridges, hydrophobic interactions, chemical linkages, UV cross-linking baking, etc. Allele-specific oligonucleotides may be synthesized directly on the solid support or attached to the solid support subsequent to synthesis. Solid-supports suitable for use in detection methods of the invention include substrates made of silicon, glass, plastic, paper and the like, which may be formed, for example, into wells (as in 96-well plates), slides, sheets, membranes, fibers, chips, dishes, and beads. The solid support may be treated, coated or derivatized to facilitate the immobilization of the allele-specific oligonucleotide or target nucleic acid.

The genotype for one or more polymorphic sites in the gene of an individual may also be determined by hybridization of one or both copies of the gene, or a fragment thereof, to nucleic acid arrays and subarrays such as described in WO 95/11995. The arrays would contain a battery of allele-specific oligonucleotides representing each of the polymorphic sites to be included in the genotype or haplotype.

The identity of polymorphisms may also be determined using a mismatch detection technique, including but not limited to the RNase protection method using riboprobes (Winter et al., 1985; Meyers et al., 1985) and proteins which recognize nucleotide mismatches, such as the *E. coli* mutS protein (Modrich, 1991). Alternatively, variant alleles can be identified by single strand conformation polymorphism (SSCP) analysis (Orita et al., 1989; Humphries, et al., 1996) or denaturing gradient gel electrophoresis (DGGE) (Wartell et al., 1990; Sheffield et al., 1989).

A polymerase-mediated primer extension method may also be used to identify the polymorphism(s). Several such methods have been described in the patent and scientific literature. Extended primers containing a polymorphism may be detected by mass spectrometry as described in U.S. Pat. No. 5,605,798. Another primer extension method is allele-specific PCR (Ruano et al., 1989; Ruano et al., 1991; WO 93/22456; Turki et al., 1995).

1. Hybridization

The use of a probe or primer of between 7, 8, 9, 10, 11, 12, 13, 14, 15, 16, 17, 18, 19, 20, 21, 22, 23, 24, 25, 50, 60, 70, 80, 90, or 100 nucleotides, preferably between 17 and 100 nucleotides in length, or in some aspects of the invention up to 1-2 kilobases or more in length, allows the formation of a duplex molecule that is both stable and selective. Molecules having complementary sequences over contiguous stretches greater than 20 bases in length are generally preferred, to increase stability and/or selectivity of the hybrid molecules obtained. One will generally prefer to design nucleic acid molecules for hybridization having one or more complementary sequences of 20 to 30 nucleotides, or even longer where desired. Such fragments may be readily prepared, for example, by directly synthesizing the fragment by chemical means or by introducing selected sequences into recombinant vectors for recombinant production.

Accordingly, the nucleotide sequences of the invention may be used for their ability to selectively form duplex molecules with complementary stretches of DNAs and/or RNAs or to provide primers for amplification of DNA or RNA from samples. Depending on the application envisioned, one would desire to employ varying conditions of hybridization to achieve varying degrees of selectivity of the probe or primers for the target sequence.

For applications requiring high selectivity, one will typically desire to employ relatively high stringency conditions to form the hybrids. For example, relatively low salt and/or high temperature conditions, such as provided by about 0.02 M to about 0.10 M NaCl at temperatures of about 50° C. to about 70° C. Such high stringency conditions tolerate little, if any, mismatch between the probe or primers and the template or target strand and would be particularly suitable for isolating specific genes or for detecting a specific polymorphism. It is generally appreciated that conditions can be rendered more stringent by the addition of increasing amounts of formamide. For example, under highly stringent conditions, hybridization to filter-bound DNA may be carried out in 0.5 M NaHPO$_4$, 7% sodium dodecyl sulfate (SDS), 1 mM EDTA at 65° C., and washing in 0.1×SSC/0.1% SDS at 68° C. (Ausubel et al., 1989).

Conditions may be rendered less stringent by increasing salt concentration and/or decreasing temperature. For example, a medium stringency condition could be provided by about 0.1 to 0.25 M NaCl at temperatures of about 37° C. to about 55° C., while a low stringency condition could be provided by about 0.15 M to about 0.9 M salt, at temperatures ranging from about 20° C. to about 55° C. Under low stringent conditions, such as moderately stringent conditions the washing may be carried out for example in 0.2×SSC/0.1% SDS at 42° C. (Ausubel et al., 1989). Hybridization conditions can be readily manipulated depending on the desired results.

In other embodiments, hybridization may be achieved under conditions of, for example, 50 mM Tris-HCl (pH 8.3), 75 mM KCl, 3 mM MgCl$_2$, 1.0 mM dithiothreitol, at temperatures between approximately 20° C. to about 37° C. Other hybridization conditions utilized could include approximately 10 mM Tris-HCl (pH 8.3), 50 mM KCl, 1.5 mM MgCl$_2$, at temperatures ranging from approximately 40° C. to about 72° C.

In certain embodiments, it will be advantageous to employ nucleic acids of defined sequences of the present invention in combination with an appropriate means, such as a label, for determining hybridization. A wide variety of appropriate indicator means are known in the art, including fluorescent, radioactive, enzymatic or other ligands, such as avidin/biotin, which are capable of being detected. In preferred embodiments, one may desire to employ a fluorescent label or an enzyme tag such as urease, alkaline phosphatase or peroxidase, instead of radioactive or other environmentally undesirable reagents. In the case of enzyme tags, colorimetric indicator substrates are known that can be employed to provide a detection means that is visibly or spectrophotometrically detectable, to identify specific hybridization with complementary nucleic acid containing samples. In other aspects, a particular nuclease cleavage site may be present and detection of a particular nucleotide sequence can be determined by the presence or absence of nucleic acid cleavage.

In general, it is envisioned that the probes or primers described herein will be useful as reagents in solution hybridization, as in PCR, for detection of expression or genotype of corresponding genes, as well as in embodiments employing a solid phase. In embodiments involving a solid phase, the test DNA (or RNA) is adsorbed or otherwise affixed to a selected matrix or surface. This fixed, single-stranded nucleic acid is then subjected to hybridization with selected probes under desired conditions. The conditions selected will depend on the particular circumstances (depending, for example, on the G+C content, type of target nucleic acid, source of nucleic acid, size of hybridization probe, etc.). Optimization of hybridization conditions for the particular application of interest is well known to those of skill in the art. After washing of the hybridized molecules to remove non-specifically bound probe molecules, hybridization is detected, and/or quantified, by determining the amount of bound label. Representative solid phase hybridization methods are disclosed in U.S. Pat. Nos. 5,843,663, 5,900,481 and 5,919,626. Other methods of hybridization that may be used in the practice of the present invention are disclosed in U.S. Pat. Nos. 5,849,481, 5,849,486 and 5,851,772. The relevant portions of these and other references identified in this section of the Specification are incorporated herein by reference.

2. Amplification of Nucleic Acids

Nucleic acids used as a template for amplification may be isolated from cells, tissues or other samples according to standard methodologies (Sambrook et al., 2001). In certain embodiments, analysis is performed on whole cell or tissue homogenates or biological fluid samples with or without substantial purification of the template nucleic acid. The nucleic acid may be genomic DNA or fractionated or whole cell RNA. Where RNA is used, it may be desired to first convert the RNA to a complementary DNA.

The term "primer," as used herein, is meant to encompass any nucleic acid that is capable of priming the synthesis of a nascent nucleic acid in a template-dependent process. Typically, primers are oligonucleotides from ten to twenty and/or thirty base pairs in length, but longer sequences can be employed. Primers may be provided in double-stranded and/or single-stranded form, although the single-stranded form is preferred.

Pairs of primers designed to selectively hybridize to nucleic acids corresponding to the variable heavy chain gene locus, variants and fragments thereof are contacted with the template nucleic acid under conditions that permit selective hybridization. Depending upon the desired application, high stringency hybridization conditions may be selected that will only allow hybridization to sequences that are completely complementary to the primers. In other embodiments, hybridization may occur under reduced stringency to allow for amplification of nucleic acids that contain one or more mismatches with the primer sequences. Once hybridized, the template-primer complex is contacted with one or more enzymes that facilitate template-dependent nucleic acid synthesis. Multiple rounds of amplification, also referred to as "cycles," are conducted until a sufficient amount of amplification product is produced.

The amplification product may be detected, analyzed or quantified. In certain applications, the detection may be performed by visual means. In certain applications, the detection may involve indirect identification of the product via chemiluminescence, radioactive scintigraphy of incorporated radiolabel or fluorescent label or even via a system using electrical and/or thermal impulse signals (Affymax technology; Bellus, 1994).

A number of template dependent processes are available to amplify the oligonucleotide sequences present in a given template sample. One of the best known amplification methods is the polymerase chain reaction (referred to as PCR™) which is described in detail in U.S. Pat. Nos. 4,683,195, 4,683,202 and 4,800,159, and in Innis et al., 1988, each of which is incorporated herein by reference in their entirety.

Primer extension, which may be used as a stand alone technique or in combination with other methods (such as PCR), requires a labeled primer (usually 20-50 nucleotides in length) which is complementary to a region near the 5' end of the gene. The primer is allowed to anneal to the RNA and reverse transcriptase is used to synthesize complementary cDNA to the RNA until it reaches the 5' end of the RNA.

Another method for amplification is ligase chain reaction ("LCR"), disclosed in European Application No. 320 308, incorporated herein by reference in its entirety. U.S. Pat. No. 4,883,750 describes a method similar to LCR for binding probe pairs to a target sequence. A method based on PCR™ and oligonucleotide ligase assay (OLA) (described in further detail below), disclosed in U.S. Pat. No. 5,912,148, may also be used.

Alternative methods for amplification of target nucleic acid sequences that may be used in the practice of the present invention are disclosed in U.S. Pat. No. 5,843,650, 5,846,709, 5,846,783, 5,849,546, 5,849,497, 5,849,547, 5,858,652, 5,866,366, 5,916,776, 5,922,574, 5,928,905, 5,928,906, 5,932,451, 5,935,825, 5,939,291 and 5,942,391, Great Britain Application 2 202 328, and in PCT Application PCT/US89/01025, each of which is incorporated herein by reference in its entirety. Qbeta Replicase, described in PCT Application PCT/US87/00880, may also be used as an amplification method in the present invention.

An isothermal amplification method, in which restriction endonucleases and ligases are used to achieve the amplification of target molecules that contain nucleotide 5'-[alpha-thio]-triphosphates in one strand of a restriction site may also be useful in the amplification of nucleic acids in the present invention (Walker et al., 1992). Strand Displacement Amplification (SDA), disclosed in U.S. Pat. No. 5,916,779, is another method of carrying out isothermal amplification of nucleic acids which involves multiple rounds of strand displacement and synthesis, i.e., nick translation Other nucleic acid amplification procedures include transcription-based amplification systems (TAS), including nucleic acid sequence based amplification (NASBA) and 3SR (Kwoh et al., 1989; PCT Application WO 88/10315, incorporated herein by reference in their entirety). European Application 329 822 disclose a nucleic acid amplification process involving cyclically synthesizing single-stranded RNA ("ssRNA"), ssDNA, and double-stranded DNA (dsDNA), which may be used in accordance with the present invention.

PCT Application WO 89/06700 (incorporated herein by reference in its entirety) disclose a nucleic acid sequence amplification scheme based on the hybridization of a promoter region/primer sequence to a target single-stranded DNA ("ssDNA") followed by transcription of many RNA copies of the sequence. This scheme is not cyclic, i.e., new templates are not produced from the resultant RNA transcripts. Other amplification methods include "RACE" and "one-sided PCR" (Frohman, 1990; Ohara et al., 1989).

Real-time polymerase chain reaction, also called quantitative real time polymerase chain reaction (qPCR) or kinetic polymerase chain reaction, is a laboratory technique based on the polymerase chain reaction, which is used to amplify and simultaneously quantify a targeted DNA molecule. It enables both detection and quantification (as absolute number of copies or relative amount when normalized to DNA input or additional normalizing genes) of a specific sequence in a DNA sample.

The procedure follows the general principle of polymerase chain reaction; its key feature is that the amplified DNA is quantified as it accumulates in the reaction in real time after each amplification cycle. Two common methods of quantification are the use of fluorescent dyes that intercalate with double-stranded DNA, and modified DNA oligonucleotide probes that fluoresce when hybridized with a complementary DNA.

Frequently, real-time polymerase chain reaction is combined with reverse transcription polymerase chain reaction to quantify low abundance messenger RNA (mRNA), enabling a researcher to quantify relative gene expression at a particular time, or in a particular cell or tissue type. Although real-time quantitative polymerase chain reaction is often marketed as RT-PCR, it should not be confused with reverse transcription polymerase chain reaction, also known as RT-PCR.

A DNA-binding dye binds to all double-stranded (ds)DNA in a PCR reaction, causing fluorescence of the dye. An increase in DNA product during PCR therefore leads to an increase in fluorescence intensity and is measured at each cycle, thus allowing DNA concentrations to be quantified. However, dsDNA dyes such as SYBR Green will bind to all dsDNA PCR products, including non-specific PCR products (such as "primer dimers"). This can potentially interfere with or prevent accurate quantification of the intended target sequence. The reaction is prepared as usual, with the addition of fluorescent dsDNA dye.

The reaction is run in a thermocycler, and after each cycle, the levels of fluorescence are measured with a detector; the dye only fluoresces when bound to the dsDNA (i.e., the PCR product). With reference to a standard dilution, the dsDNA concentration in the PCR can be determined.

Like other real-time PCR methods, the values obtained do not have absolute units associated with it (i.e. mRNA copies/cell). As described above, a comparison of a measured DNA/RNA sample to a standard dilution will only give a fraction or ratio of the sample relative to the standard, allowing only relative comparisons between different tissues or experimental conditions. To ensure accuracy in the quantification, it is usually necessary to normalize expression of a target gene to a stably expressed gene. This can correct possible differences in RNA quantity or quality across experimental samples.

Using fluorescent reporter probes is the most accurate and most reliable of the methods, but also the most expensive. It uses a sequence-specific RNA or DNA-based probe to quantify only the DNA containing the probe sequence; therefore, use of the reporter probe significantly increases specificity, and allows quantification even in the presence of some non-specific DNA amplification. This potentially allows for multiplexing—assaying for several genes in the same reaction by using specific probes with different-coloured labels, provided that all genes are amplified with similar efficiency.

It is commonly carried out with an RNA-based probe with a fluorescent reporter at one end and a quencher of fluorescence at the opposite end of the probe. The close proximity of the reporter to the quencher prevents detection of its fluorescence; breakdown of the probe by the 5' to 3' exonuclease activity of the taq polymerase breaks the reporter-quencher proximity and thus allows unquenched emission of fluorescence, which can be detected. An increase in the product targeted by the reporter probe at each PCR cycle therefore causes a proportional increase in fluorescence due to the breakdown of the probe and release of the reporter.

The PCR reaction is prepared as usual (see PCR), and the reporter probe is added. As the reaction commences, during the annealing stage of the PCR both probe and primers anneal to the DNA target. Polymerization of a new DNA strand is initiated from the primers, and once the polymerase reaches the probe, its 5'-3-exonuclease degrades the probe, physically separating the fluorescent reporter from the quencher, resulting in an increase in fluorescence.

Fluorescence is detected and measured in the real-time PCR thermocycler, and its geometric increase corresponding to exponential increase of the product is used to determine the threshold cycle ($C_T$) in each reaction.

Quantitating gene expression by traditional methods presents several problems. Firstly, detection of mRNA on a Northern blot or PCR products on a gel or Southern blot is time-consuming and does not allow precise quantitation. Also, over the 20-40 cycles of a typical PCR reaction, the amount of product reaches a plateau determined more by the amount of primers in the reaction mix than by the input template/sample.

Relative concentrations of DNA present during the exponential phase of the reaction are determined by plotting fluorescence against cycle number on a logarithmic scale (so an exponentially increasing quantity will give a straight line). A threshold for detection of fluorescence above background is determined. The cycle at which the fluorescence from a sample crosses the threshold is called the cycle threshold, $C_t$. Since the quantity of DNA doubles every cycle during the exponential phase, relative amounts of DNA can be calculated, e.g., a sample whose $C_t$ is 3 cycles earlier than another's has $2^3=8$ times more template.

Amounts of RNA or DNA are then determined by comparing the results to a standard curve produced by RT-PCR of serial dilutions (e.g., undiluted, 1:4, 1:16, 1:64) of a known amount of RNA or DNA. As mentioned above, to accurately quantify gene expression, the measured amount of RNA from the gene of interest is divided by the amount of RNA from a housekeeping gene measured in the same sample to normalize for possible variation in the amount and quality of RNA between different samples. This normalization permits accurate comparison of expression of the gene of interest between different samples, provided that the expression of the reference (housekeeping) gene used in the normalization is very similar across all the samples. Choosing a reference gene fulfilling this criterion is therefore of high importance, and often challenging, because only very few genes show equal levels of expression across a range of different conditions or tissues.

3. Detection of Nucleic Acids

Following any amplification, it may be desirable to separate the amplification product from the template and/or the excess primer. In one embodiment, amplification products are separated by agarose, agarose-acrylamide or polyacrylamide gel electrophoresis using standard methods (Sambrook et al., 2001). Separated amplification products may be cut out and eluted from the gel for further manipulation. Using low melting point agarose gels, the separated band may be removed by heating the gel, followed by extraction of the nucleic acid.

Separation of nucleic acids may also be effected by spin columns and/or chromatographic techniques known in art. There are many kinds of chromatography which may be used in the practice of the present invention, including adsorption, partition, ion-exchange, hydroxylapatite, molecular sieve, reverse-phase, column, paper, thin-layer, and gas chromatography as well as HPLC.

In certain embodiments, the amplification products are visualized, with or without separation. A typical visualization method involves staining of a gel with ethidium bromide and visualization of bands under UV light. Alternatively, if the amplification products are integrally labeled with radio- or fluorometrically-labeled nucleotides, the separated amplification products can be exposed to x-ray film or visualized under the appropriate excitatory spectra.

In one embodiment, following separation of amplification products, a labeled nucleic acid probe is brought into contact with the amplified marker sequence. The probe preferably is conjugated to a chromophore but may be radiolabeled. In another embodiment, the probe is conjugated to a binding partner, such as an antibody or biotin, or another binding partner carrying a detectable moiety.

In particular embodiments, detection is by Southern blotting and hybridization with a labeled probe. The techniques involved in Southern blotting are well known to those of skill in the art (see Sambrook et al., 2001). One example of the foregoing is described in U.S. Pat. No. 5,279,721, incorporated by reference herein, which discloses an apparatus and method for the automated electrophoresis and transfer of nucleic acids. The apparatus permits electrophoresis and blotting without external manipulation of the gel and is ideally suited to carrying out methods according to the present invention.

Other methods of nucleic acid detection that may be used in the practice of the instant invention are disclosed in U.S. Pat. Nos. 5,840,873, 5,843,640, 5,843,651, 5,846,708, 5,846,717, 5,846,726, 5,846,729, 5,849,487, 5,853,990, 5,853,992, 5,853,993, 5,856,092, 5,861,244, 5,863,732, 5,863,753, 5,866,331, 5,905,024, 5,910,407, 5,912,124, 5,912,145, 5,919,630, 5,925,517, 5,928,862, 5,928,869, 5,929,227, 5,932,413 and 5,935,791, each of which is incorporated herein by reference.

4. Other Assays

Other methods for genetic screening may be used within the scope of the present invention, for example, to detect mutations in genomic DNA, cDNA and/or RNA samples. Methods used to detect point mutations include denaturing gradient gel electrophoresis (DGGE), restriction fragment length polymorphism analysis (RFLP), chemical or enzymatic cleavage methods, direct sequencing of target regions amplified by PCR™ (see above), single-strand conformation polymorphism analysis (SSCP) and other methods well known in the art.

One method of screening for point mutations is based on RNase cleavage of base pair mismatches in RNA/DNA or RNA/RNA heteroduplexes. As used herein, the term "mismatch" is defined as a region of one or more unpaired or mispaired nucleotides in a double-stranded RNA/RNA, RNA/DNA or DNA/DNA molecule. This definition thus includes mismatches due to insertion/deletion mutations, as well as single or multiple base point mutations.

U.S. Pat. No. 4,946,773 describes an RNase A mismatch cleavage assay that involves annealing single-stranded DNA or RNA test samples to an RNA probe, and subsequent treatment of the nucleic acid duplexes with RNase A. For the detection of mismatches, the single-stranded products of the RNase A treatment, electrophoretically separated according to size, are compared to similarly treated control duplexes. Samples containing smaller fragments (cleavage products) not seen in the control duplex are scored as positive.

Other investigators have described the use of RNase I in mismatch assays. The use of RNase I for mismatch detection is described in literature from Promega Biotech. Promega markets a kit containing RNase I that is reported to cleave three out of four known mismatches. Others have described using the MutS protein or other DNA-repair enzymes for detection of single-base mismatches.

Alternative methods for detection of deletion, insertion or substitution mutations that may be used in the practice of the present invention are disclosed in U.S. Pat. Nos. 5,849,483, 5,851,770, 5,866,337, 5,925,525 and 5,928,870, each of which is incorporated herein by reference in its entirety.

5. Polymorphic Nucleic Acid Screening Methods

Spontaneous mutations that arise during the course of evolution in the genomes of organisms are often not immediately transmitted throughout all of the members of the species, thereby creating polymorphic alleles that co-exist in the species populations. Often polymorphisms are the cause of genetic diseases. Several classes of polymorphisms have been identified. For example, variable nucleotide type polymorphisms (VNTRs), arise from spontaneous tandem duplications of di- or trinucleotide repeated motifs of nucleotides. If such variations alter the lengths of DNA fragments generated by restriction endonuclease cleavage, the variations are referred to as restriction fragment length polymorphisms (RFLPs). RFLPs are been widely used in human and animal genetic analyses.

Another class of polymorphisms is generated by the replacement of a single nucleotide. Such single nucleotide polymorphisms (SNPs) rarely result in changes in a restriction endonuclease site. Thus, SNPs are rarely detectable restriction fragment length analysis. SNPs are the most common genetic variations and occur once every 100 to 300 bases and several SNP mutations have been found that affect a single nucleotide in a protein-encoding gene in a manner sufficient to actually cause a genetic disease. SNP diseases are exemplified by hemophilia, sickle-cell anemia, hereditary hemochromatosis, late-onset Alzheimer's disease, etc.

Several methods have been developed to screen polymorphisms and some examples are listed below. The reference of Kwok and Chen (2003) and Kwok (2001) provide overviews of some of these methods; both of these references are specifically incorporated by reference. SNPs can be characterized by the use of any of these methods or suitable modification thereof. Such methods include the direct or indirect sequencing of the site, the use of restriction enzymes where the respective alleles of the site create or destroy a restriction site, the use of allele-specific hybridization probes, the use of antibodies that are specific for the proteins encoded by the different alleles of the polymorphism, or any other biochemical interpretation.

i. DNA Sequencing

The most commonly used method of characterizing a polymorphism is direct DNA sequencing of the genetic locus that flanks and includes the polymorphism. Such analysis can be accomplished using either the "dideoxy-mediated chain termination method," also known as the "Sanger Method" (Sanger et al., 1975) or the "chemical degradation method," also known as the "Maxam-Gilbert method" (Maxam et al., 1977). Sequencing in combination with genomic sequence-specific amplification technologies, such as the polymerase chain reaction may be utilized to facilitate the recovery of the desired genes (Mullis et al., 1986; European Patent Application 50,424; European Patent Application. 84,796, European Patent Application 258,017, European Patent Application. 237,362; European Patent Application. 201,184; U.S. Pat. Nos. 4,683,202; 4,582,788; and 4,683,194), all of the above incorporated herein by reference.

ii. Exonuclease Resistance

Other methods that can be employed to determine the identity of a nucleotide present at a polymorphic site utilize a specialized exonuclease-resistant nucleotide derivative (U.S. Pat. No. 4,656,127). A primer complementary to an allelic sequence immediately 3'-to the polymorphic site is hybridized to the DNA under investigation. If the polymorphic site on the DNA contains a nucleotide that is complementary to the particular exonucleotide-resistant nucleotide derivative present, then that derivative will be incorporated by a polymerase onto the end of the hybridized primer. Such incorporation makes the primer resistant to exonuclease cleavage and thereby permits its detection. As the identity of the exonucleotide-resistant derivative is known one can determine the specific nucleotide present in the polymorphic site of the DNA.

iii. Microsequencing Methods

Several other primer-guided nucleotide incorporation procedures for assaying polymorphic sites in DNA have been described (Komher et al., 1989; Sokolov, 1990; Syvanen 1990; Kuppuswamy et al., 1991; Prezant et al., 1992; Ugozzoll et al., 1992; Nyren et al., 1993). These methods rely on the incorporation of labeled deoxynucleotides to discriminate between bases at a polymorphic site. As the signal is proportional to the number of deoxynucleotides incorporated, polymorphisms that occur in runs of the same nucleotide result in a signal that is proportional to the length of the run (Syvanen et al., 1990).

iv. Extension in Solution

French Patent 2,650,840 and PCT Application WO91/02087 discuss a solution-based method for determining the identity of the nucleotide of a polymorphic site. According to these methods, a primer complementary to allelic sequences immediately 3'-to a polymorphic site is used. The identity of the nucleotide of that site is determined using labeled dideoxynucleotide derivatives which are incorporated at the end of the primer if complementary to the nucleotide of the polymorphic site.

v. Genetic Bit Analysis or Solid-Phase Extension

PCT Application WO92/15712 describes a method that uses mixtures of labeled terminators and a primer that is complementary to the sequence 3' to a polymorphic site. The labeled terminator that is incorporated is complementary to the nucleotide present in the polymorphic site of the target molecule being evaluated and is thus identified. Here the primer or the target molecule is immobilized to a solid phase.

vi. Oligonucleotide Ligation Assay (OLA)

This is another solid phase method that uses different methodology (Landegren et al., 1988). Two oligonucleotides, capable of hybridizing to abutting sequences of a single strand of a target DNA are used. One of these oligonucleotides is biotinylated while the other is detectably labeled. If the precise complementary sequence is found in a target molecule, the oligonucleotides will hybridize such that their termini abut, and create a ligation substrate. Ligation permits the recovery of the labeled oligonucleotide by using avidin. Other nucleic acid detection assays, based on this method, combined with PCR have also been described (Nickerson et al., 1990). Here, PCR is used to achieve the exponential amplification of target DNA, which is then detected using the OLA.

vii. Ligase/Polymerase-Mediated Genetic Bit Analysis

U.S. Pat. No. 5,952,174 describes a method that also involves two primers capable of hybridizing to abutting sequences of a target molecule. The hybridized product is formed on a solid support to which the target is immobilized. Here the hybridization occurs such that the primers are separated from one another by a space of a single nucleotide. Incubating this hybridized product in the presence of a polymerase, a ligase, and a nucleoside triphosphate mixture containing at least one deoxynucleoside triphosphate allows the ligation of any pair of abutting hybridized oligonucleotides. Addition of a ligase results in two events required to generate a signal, extension and ligation. This provides a higher specificity and lower "noise" than methods using either extension or ligation alone and unlike the polymerase-based assays, this method enhances the specificity of the polymerase step by combining it with a second hybridization and a ligation step for a signal to be attached to the solid phase.

viii. Invasive Cleavage Reactions

Invasive cleavage reactions can be used to evaluate cellular DNA for a particular polymorphism. A technology called INVADER® employs such reactions (e.g., de Arruda et al., 2002; Stevens et al., 2003, which are incorporated by reference). Generally, there are three nucleic acid molecules: 1) an oligonucleotide upstream of the target site ("upstream oligo"), 2) a probe oligonucleotide covering the target site ("probe"), and 3) a single-stranded DNA with the the target site ("target"). The upstream oligo and probe do not overlap but they contain contiguous sequences. The probe contains a donor fluorophore, such as fluoroscein, and an acceptor dye, such as Dabcyl. The nucleotide at the 3' terminal end of the upstream oligo overlaps ("invades") the first base pair of a probe-target duplex. Then the probe is cleaved by a structure-specific 5' nuclease causing separation of the fluorophore/ quencher pair, which increases the amount of fluorescence that can be detected. See Lu et al. (2004). In some cases, the assay is conducted on a solid-surface or in an array format.

III. Predicting and Diagnosing Multiple Sclerosis

A. Multiple Sclerosis

Multiple Sclerosis (MS) is one of the most common diseases of the central nervous system (brain and spinal cord). It is an inflammatory condition associated with demyelination, or loss of the myelin sheath. Myelin, a fatty material that insulates nerves, acts as insulator in allowing nerves to transmit impulses from one point to another. In MS, the loss of myelin is accompanied by a disruption in the ability of the nerves to conduct electrical impulses to and from the brain and this produces the various symptoms of MS, such as impairments in vision, muscle coordination, strength, sensation, speech and swallowing, bladder control, sexuality and cognitive function. The plaques or lesions where myelin is lost appear as hardened, scar-like areas. These scars appear at different times and in different areas of the brain and spinal cord, hence the term "multiple" sclerosis, literally meaning many scars.

Currently, there is no single laboratory test, symptom, or physical finding that provides a conclusive diagnosis of MS. To complicate matters, symptoms of MS can easily be confused with a wide variety of other diseases such as acute disseminated encephalomyelitis, Lyme disease, HIV-associated myelopathy, HTLV-I-associated myelopathy, neurosyphilis, progressive multifocal leukoencephalopathy, systemic lupus erythematosus, polyarteritis nodosa, Sjögren's syndrome, Behçet's disease, sarcoidosis, paraneoplastic syndromes, subacute combined degeneration of cord, subacute myelo-optic neuropathy, adrenomyeloneuropathy, spinocerebellar syndromes, hereditary spastic paraparesis/primary lateral sclerosis, strokes, tumors, arteriovenous malformations, arachnoid cysts, Arnold-Chiari malformations, and cervical spondylosis. Consequently, the diagnosis of MS must be made by a process that demonstrates findings that are consistent with MS, and also rules out other causes.

Generally, diagnosis of MS relies on two criteria. First, there must have been two attacks at least one month apart. An attack, also known as an exacerbation, flare, or relapse, is a sudden appearance of or worsening of an MS symptom or symptoms which lasts at least 24 hours. Second, there must be more than one area of damage to central nervous system myelin sheath. Damage to sheath must have occurred at more than one point in time and not have been caused by any other disease that can cause demyelination or similar neurologic symptoms. MRI (magnetic resonance imaging) currently is the preferred method of imaging the brain to detect the presence of plaques or scarring caused by MS.

The diagnosis of MS cannot be made, however, solely on the basis of MRI. Other diseases can cause comparable lesions in the brain that resemble those caused by MS. Furthermore, the appearance of brain lesions by MRI can be quite heterogeneous in different patients, even resembling brain or spinal cord tumors in some. In addition, a normal MRI scan does not rule out a diagnosis of MS, as a small number of patients with confirmed MS do not show any lesions in the brain on MRI. These individuals often have spinal cord lesions or lesions which cannot be detected by MRI. As a result, it is critical that a thorough clinical exam also include a patient history and functional testing. This should cover mental, emotional, and language functions, movement and coordination, vision, balance, and the functions of the five senses. Sex, birthplace, family history, and age of the person when symptoms first began are also important considerations. Other tests, including evoked potentials (electrical diagnostic studies that may reveal delays in central nervous system conduction times), cerebrospinal fluid (seeking the presence of clonally-expanded immunoglobulin genes, referred to as oligoclonal bands), and blood (to rule out other causes), may be required in certain cases.

B. Samples and Preparation

The present invention contemplates the identification of VH4 sequences from B cells obtained from any sample (fluid or tissue) that would contain such cells. In particular, the present invention will rely on peripheral blood as a source of B cells, given the ease of obtention and the plentiful nature of B cells. In addition, given the CNS implications of MS, cerebrospinal fluid provides another potential source of B cells for analysis. Methods for separating and analyzing nucleic acids are provided above.

C. Therapy and Prophylaxis

It may be that, on the basis of the diagnosis or prediction provided by the methods described herein, one will wish to begin, end or modify a therapeutic regimen. In particular, subjects diagnosed as having or at risk of developing MS may be started on a therapeutic regimen. The primary aims of therapy are returning function after an attack, preventing new attacks, and preventing disability. As with any medical treatment, medications used in the management of MS have several adverse effects, and many possible therapies are still under investigation.

During symptomatic attacks, administration of high doses of intravenous corticosteroids, such as methylprednisolone, is the routine therapy for acute relapses. The aim of this kind of treatment is to end the attack sooner and leave fewer lasting deficits in the patient. Although generally effective in the short term for relieving symptoms, corticosteroid treatments do not appear to have a significant impact on long-term recovery. Potential side effects include osteoporosis and impaired memory, the latter being reversible.

The earliest clinical presentation of relapsing-remitting MS (RRMS) is the clinically isolated syndrome (CIS). Several studies have shown that treatment with interferons during an initial attack can decrease the chance that a patient will develop MS. As of 2007, six disease-modifying treatments have been approved by regulatory agencies of different countries for relapsing-remitting MS. Three are interferons: two formulations of interferon beta-1a (trade names Avonex and Rebif) and one of interferon beta-1b (U.S. trade name Betaseron™, in Europe and Japan Betaferon). A fourth medication is glatiramer acetate (Copaxone™). The fifth medication, mitoxantrone, is an immunosuppressant also used in cancer chemotherapy, is approved only in the USA and largely for SPMS. Finally, the sixth is natalizumab (marketed as Tysabri™). All six medications are modestly effective at decreasing the number of attacks and slowing progression to disability, although they differ in their efficacy rate and studies of their long-term effects are still lacking. Comparisons between immunomodulators (all but mitoxantrone) show that the most effective is natalizumab, both in terms of relapse rate reduction and halting disability progression; it has also been shown to reduce the severity of MS. Mitoxantrone may be the most effective of them all; however, it is generally considered not as a long-term therapy as its use is limited by severe cardiotoxicity.

The interferons and glatiramer acetate are delivered by frequent injections, varying from once-per-day for glatiramer acetate to once-per-week (but intra-muscular) for Avonex. Natalizumab and mitoxantrone are given by IV infusion at monthly intervals. Treatment of progressive MS is more difficult than relapsing-remitting MS. Mitoxantrone has shown positive effects in patients with a secondary progressive and progressive relapsing courses. It is moderately effective in reducing the progression of the disease and the frequency of relapses in patients in short-term follow-up. On the other hand no treatment has been proven to modify the course of primary progressive MS.

Disease-modifying treatments only reduce the progression rate of the disease but do not stop it. As multiple sclerosis progresses, the symptomatology tends to increase. The disease is associated with a variety of symptoms and functional deficits that result in a range of progressive impairments and handicap. Management of these deficits is therefore very important. Both drug therapy and neurorehabilitation have shown to ease the burden of some symptoms, even though neither influence disease progression. As for any patient with neurologic deficits, a multidisciplinary approach is key to limiting and overcoming disability; however there are particular difficulties in specifying a 'core team' because people with MS may need help from almost any health profession or service at some point. Similarly for each symptom there are different treatment options. Treatments should therefore be individualized depending both on the patient and the physician.

The present invention also contemplates the use of novel therapeutic agents—antibodies or peptides/peptoids that bind to the altered VH4 genes described herein—to treat SLE. VH4-antibody therapeutics can be prepared and screened for reactivity using well known techniques. Peptides and peptiods that act as "mimotopes," or epitope-mimicking structures can be administered and used to sequester the VH4 products away from pathologic interactions. See Reimer & Jensen-Jarolim (2007).

IV. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Materials and Methods

Patient description and database generation. Cerebrospinal fluid and peripheral blood were collected from eleven relapsing remitting MS patients at UT Southwestern Medical Center, in accordance with the UT Southwestern Institutional Review Board. Brief patient descriptions are summarized in Table 7. This database includes patients whose sequences have been analyzed elsewhere (Monson et al., 2005; Harp et al., 2007). Sequences obtained from CSF-derived B cell repertoires from these patients were analyzed using Sequencher 4.5 (Gene Codes Corporation, Ann Arbor, Mich.). Differences from the IgBlast (NCBI; world wide web at ncbi.nlm.nih.gov/igblast) were evaluated, but no changes in gene usage were noted. Sequences with more than 4 mutations (less than 98% germline) were designated as the MS memory (mMSCSF) subdatabase (Brezinschek et al., 1998; Damle et al., 1999; Hamblin et al., 1999). Two RRMS patients were collected under the University of Colorado School of Medicine Institutional Review Board (Ritchie et al., 2004). Brief patient descriptions are included in Table 7. B cell repertoire summaries from these patients was published in Ritchie et al. (2004), and analyzed using DNASIS Max software located at the V Base Sequence directory (world wide web at mrc-cpe.cam.ac.uk). The HCPB antibody database has been used in multiple studies (Brezinschek et al., 1997; Brezinschek et al., 1998; Dorner et al., 1997; Dorner et al., 1998a; Dorner et al., 1998b; Dorner et al., 1998c; Farner et al., 1999; Hansen et al., 2000; Monson et al., 2000). The MSPB database was collected from the peripheral blood of three relapsing remitting MS patients (see Table 7 for brief patient summaries) at the time of CSF sampling. Peripheral blood lymphocytes were isolated by centrifugation in the presence of a Ficoll gradient. Similarly to HCPB, the inventor separated those sequences that contained more than 4 mutations (less than 98% germline sequence), which would represent peripheral memory B cells (Brezinschek et al., 1998; Damle et al., 1999; Hamblin et al., 1999) (memory MSPB or mMSPB).

The patients used to generate the class-switched $IgG_+$ $CD27_+$ database are described in Tian et al. (2007) and were collected under the Vanderbilt University Medical Center Institutional Review Board. The sequences were re-confirmed by the inventor's laboratory using IgBlast for gene usage, mutational number, and mutational codon location and type (replacement or silent). These sequences were combined with sequences from the HCPB database described above that contained more than 4 mutations (less than 98% germline sequence), which would represent peripheral memory B cells. The HCPB memory (mHCPB) sub-database and the class-switched IgG B cell database (Tian et al., 2007) did not differ in gene family usage, but did differ in MF.

One patient with Sjögren's syndrome was used; the data from this patient was published in (Hansen et al., 2003), and are listed in Table 6.

One patient with systemic lupus erythematosus (SLE) was used; the data from this patient was published in (Dorner et al., 1999), and were analyzed using GeneWorks (IntelliGenetics, Mountain View, Calif.) and Sequencher (Gene Codes, Ann Arbor, Mich.). A patient summary can be found in Table 8.

Two patients with other neurological diseases (OND) were collected from UT Southwestern Medical Center, in accordance with UT Southwestern Institutional Review Board. The obtained sequences were analyzed using Sequencher 4.5 (Gene Codes Corporation, Ann Arbor, Mich.). The patients are listed in Table 8.

Two patients were obtained that had experienced a clinically isolated event;

the diagnostic lumbar puncture was used as the CSF B cell sort and were collected from UT Southwestern Medical Center, in accordance with UT Southwestern Institutional Review Board.

The obtained sequences were analyzed using Sequencher 4.5 (Gene Codes, Ann Arbor, Mich.) for CIS132, and the sequences from CIS429 were analyzed using IgBlast. An additional CIS patient was collected under the University of Colorado School of Medicine Institutional Review Board; the data from this patient was published in Ritchie et al. (2004), and analyzed using DNASIS Max software using V Base Sequence directory (world wide web at mrccpe.cam.ac.uk). The patients included in these analyses are listed in Table 8.

B cell sorting, primer extension preamplification, and heavy chain rearrangement amplification. These methods were carried out as previously described (Farner et al., 1999;

Brezinschek et al., 1995; Foster et al., 1999). Clonally expanded B cells were defined as those VH rearrangements being represented two or more times in the repertoire. Clones were determined by similar VH and JH usage, followed by CDR3 length and composition; mutations were then compared to ensure clonality. In normalized analyses, the clones were only counted a single time, regardless of the number of rearrangements in the repertoire. Two additional MS CD19$_+$ rearrangement sequences used in VH family, VH4 gene, JH usage, overall MF, and CDR3 length numbers were obtained from (Ritchie et al., 2004).

Mutational analyses. VH read length was defined as codons 31 through 95 (CDR1 and 2, FR 2 and 3). The 3' end of the VH gene was defined as codon 95, or as long as the germline variable sequence was present. Mutational frequency was determined as the number of mutations as related by germline VH databases (Sequencher 4.5 and IgBlast) and divided by the total read length, not including FR1 in either of these figures. Mutational frequency in CDR or FR was done in the same manner, with the number of mutations in the regions (CDR1 and CDR2; FR2 and FR3) divided by the total number of nucleotides in that region.

Targeting to DGYW/WRCH motifs was evaluated by mutational frequency in a motif; this number was generated using the number of mutations in a motif divided by the total number of nucleotides in DGYW/WRCH motifs (done by the number of nucleotides in a motif of each gene multiplied by the number of times this gene was used in the repertoire). Only CDR1, FR2, CDR2, and FR3 were included in this analysis.

Mutational position frequency was calculated as the number of replacement mutations between codons 24 to 95 at each codon divided by the total number of replacement mutations. Codons 24 to 31 of FR1 were included in this analysis because most of the sequences did include these locations, and thus might be biased, but conservatively. Codon domains were defined by Kabat (1987), and codon numbers were defined by Tomlinson in V-base (vbase.mrc-cpe.cam.ac.uk).

Each mutation in CDR1, FR2, CDR2, and FR3 was counted once in mutational frequency and CDR targeting analyses, and each codon only counted once for replacement: silent ratios.

CDR3 length. CDR3 length was considered from the end of VH, including the D segment to the beginning of the JH segment, ending at codon 102, as defined by Kabat (1987).

VH4 structure. A human VH4-30.4 antibody structure was obtained from the Protein Data Bank, Chemistry Department, Brookhaven National Laboratory, Upton, N.Y. 11973 (world wide web at rcsb.org) under the identification moniker 1MCO, and adapted using the RasMol program (RasMac v2.6 available at mc2.cchem.berkeley.edu/Rasmol/Sayle and Milner-White, 1995)). The structure was described in (Guddat et al., 1993), and deposited in the data bank by the authors. The adaptations made were to show only the variable regions (including VDJ), and to highlight the codons included in the signature as described in the figure legends.

Statistical analysis. Family and VH4 gene usages were compared using chi square analysis. CDR3 lengths were analyzed by ANOVA analysis, using the Kruskal-Wallis test. Mutational position was compared between MS and HCPB using the Goodness of Fit test.

Example 2

Results

MS Patient CSF B cells have an unusually high frequency of VH4 family usage. In order to address our hypothesis that the VH4 family used in the MSCSF will be dysregulated, the inventor first analyzed whether the VH4 family was overrepresented in our CSF-derived B cell antibody database consisting of 405 sequences from 13 MS patients (patient descriptions in Table 7) and compared it to healthy control B cell repertoires (patient descriptions in Table 8) (Brezinschek et al., Brezinschek et al., 1998; Dorner et al., 1997; Dorner et al., 1998a; Dorner et al., 1998b; Dorner et al., 1998c; Farner et al., 1999; Hansen et al., 2000; Monson et al., 2000). As previously established, the majority of B cells from healthy control peripheral blood (HCPB) most often utilize VH3 family genes (61.1%) to generate their antibody repertoire, followed by VH4 family genes (18.5%) and VH1 family genes (13.7%) (FIG. 1A) (Brezinschek et al., 1995). VH2 and VH5 family genes are rarely rearranged in B cells from HCPB (2.2% and 4% respectively) (Brezinschek et al., 1995). However, HCPB is composed mostly of naïve B cells, which likely have a different family usage signature in comparison to CSF B cells, which are composed mostly of memory B cells (Harp et al., 2007; Cepok et al., 2005). Thus, we generated a sub-database of only those sequences from the HCPB database that would be categorized as memory B cells based on homology (<98%) as previously defined by us and others (Brezinschek et al., 1998; Damle et al., 1999; Hamblin et al., 1999). The inventor also combined our HCPB memory B cell sub-database with a B cell database generated from post-switch memory B cells (CD27$_+$IgG$_+$) (Tian et al., 2007). These 2 databases did not differ statistically from each other in VH1, VH2, VH3 or VH4 family usage. Comparison of this memory sub-database (mHCPB) to the full database (HCPB) revealed no significant changes in VH family usage, such that VH3 family genes constituted the majority of VH family usage in the repertoire (compare 61.1% in HCPB to 61.5% in mHCPB, p>0.14). VH1 and VH4 family usage was also comparable between the two databases. The frequency of VH4 family usage is also statistically similar to peripheral memory B cells from MS patients (mMSPB), even though it appears different (FIG. 1A) (compare 16.4% mHCPB to 22.3% mMSPB, p>0.26).

In contrast to the mHCPB database, the CSF B cell database from MS patients (MSCSF) had a significant decrease in VH3 family usage (compare 61.5% in mHCPB to 31.4% in MSCSF, p<0.001), and an increased usage of the VH4 family (compare 16.6% in mHCPB to 35.8% in MSCSF, p<0.001) and the VH1 family (compare 11.1% in mHCPB to 25.2% in MSCSF, p<0.001) (FIGS. 1A and 1B). Overrepresentation of VH4 usage was maintained even when each clone was counted once in the repertoire database (normalized; FIG. 1B). Plasma B cell repertoires (identified by CD138 expression) from MS patient CSF reported by others (Ritchie et al., 2004; Owens et al., 2007) also demonstrated a pronounced skewing to VH4 family usage (66.7%), but did not show the increased VH1 family usage seen in the CD19$_+$ B cell population (compare 2.3% in CD138$_+$ to 25.2% in CD19$_+$, p<0.001) (FIG. 1B).

Patients with Clinically Isolated Syndrome (CIS) are considered "at risk" to develop MS, but did not demonstrate VH4 prevalence observed in the MSCSF database since VH4 frequency in the CISCSF was statistically less than the MSCSF (compare 22.0% in CISCSF to 35.8% in MSCSF, p<0.01) (FIG. 1C), but similar to HCPB (compare 22.0% in CISCSF to 21.8% in HCPB, p=0.96) even when only the patients that progressed to CDMS were considered. The CISCSF$_{VH4}$ frequency is similar to that of the HCPB, mHCPB, MSPB, mMSPB, and ONDCSF. Interestingly, a previously reported CIS patient did have this increased frequency of VH4 family usage in the CSF-derived plasma cell repertoire (Ritchie et al., 2004), even though it is has yet to be demonstrated in the same patient's CSF-derived CD19+ population (compare 25.0% in CISCSF or mCISCSF to 42.1% in CIS CD138, p<0.005) (FIG. 1C).

To determine if overrepresentation of VH4 family usage was unique to the MS patients, or could be observed in other patients with autoimmune diseases mediated by humoral immunity, the inventor compared the signature of VH family usage from the peripheral blood of two other B cell autoimmune diseases, SLE (Hansen et al., 2000; Dorner et al., 1999) and Sjögren's Syndrome (Hansen et al., 2003), as well as two CSF-derived B cell repertoires from patients with other neurological diseases (OND) (Monson et al., 2005; Harp et al., 2007) to the MSCSF database. As indicated in FIG. 1D, B cell repertoires from Sjögren's or SLE patients did not utilize the VH4 family as extensively as CSF-derived B cells from MS patients (FIG. 1B). In addition, neither OND patient utilized the VH4 family more extensively than expected, regardless of the inflammatory nature of the patient's disease (FIG. 1D).

MS Patient CSF B cell database reveals no restriction in individual VH4 gene usage. The increase of VH4 family usage in the MSCSF database in comparison to mHCPB and patients with other B cell mediated autoimmune diseases could be attributed to an increased usage frequency of all nine individual heavy chain genes that comprise the VH4 family, or preferential use of one or more of the VH4 family genes. To differentiate between these two possibilities, we compared the frequency usage of the 9 individual genes that comprise the VH4 family in the MSCSF database to the mHCPB database (Table 1) and repertoires from patients with other B cell mediated autoimmune diseases (Table 2). All of the VH4 genes were used similarly in HCPB and mHCPB, with the exception of 4-04, which is observed more often in mHCPB than in the inclusive repertoire (compare 9% in the HCPB to 29% in mHCPB, p<0.03) (Table 1). MSPB and HCPB also had similar VH4 gene frequencies, as did mMSPB and mHCPB. MSCSF usage of the VH4 genes was also the same as in mMSPB, but resembled HCPB instead of mHCPB in VH4-04 usage (6% in MSCSF compared to 9% in HCPB, p=0.41, or 29% in mHCPB, p<0.001) (Table 1). These observations were maintained even when the repertoires were normalized so that each clone was represented once in the MSCSF database. Interestingly, VH4 individual gene usage frequency was similar in MSCSF, SLE and Sjögren's, with the exception of VH4-34, which was used more extensively in both SLE and Sjögren's compared to MSCSF (Table 2).

J segment usage not biased in MSCSF$_{VH4}$ populations, but is in MSPB$_{VH4}$. The extensive VH4 family usage by the MSCSF database prompted analysis of the J segment usage within the VH4-expressing B cell databases. Autoreactive B cells in peripheral germinal centers are known to utilize JH6 segments more frequently (Zheng et al., 2004), so the inventor reasoned that VH4-expressing B cells from the CSF of MS patients may also be enriched for JH6 usage. JH4 is the most common J segment used in the HCPB B cell repertoire database as described by the inventor (FIG. 6 and (Monson et al., 2005; Harp et al., 2007) and others (Brezinschek et al., 1995), even when only those B cells expressing VH4 family genes are considered (FIG. 2, HCPB$_{VH4}$=57.7%). The subdatabase consisting of only those memory B cells expressing VH4 family genes also utilized the JH4 segment most frequently (mHCPB$_{VH4}$=57.1%). In contrast, the mMSPB$_{VH4}$ database utilized JH6 segments more frequently than mHCPB (compare 58.8% mMSPB$_{VH4}$ to 11.4% mHCPB$_{VH4}$, p<0.001).

Curiously, this enrichment of JH6 utilization by VH4 expressing B cells observed in MSPB was not observed in MSCSF$_{VH4}$ (compare 40.0% MSPB$_{VH4}$ to 14.6% MSCSF$_{VH4}$, p<0.001).

Figure 3:
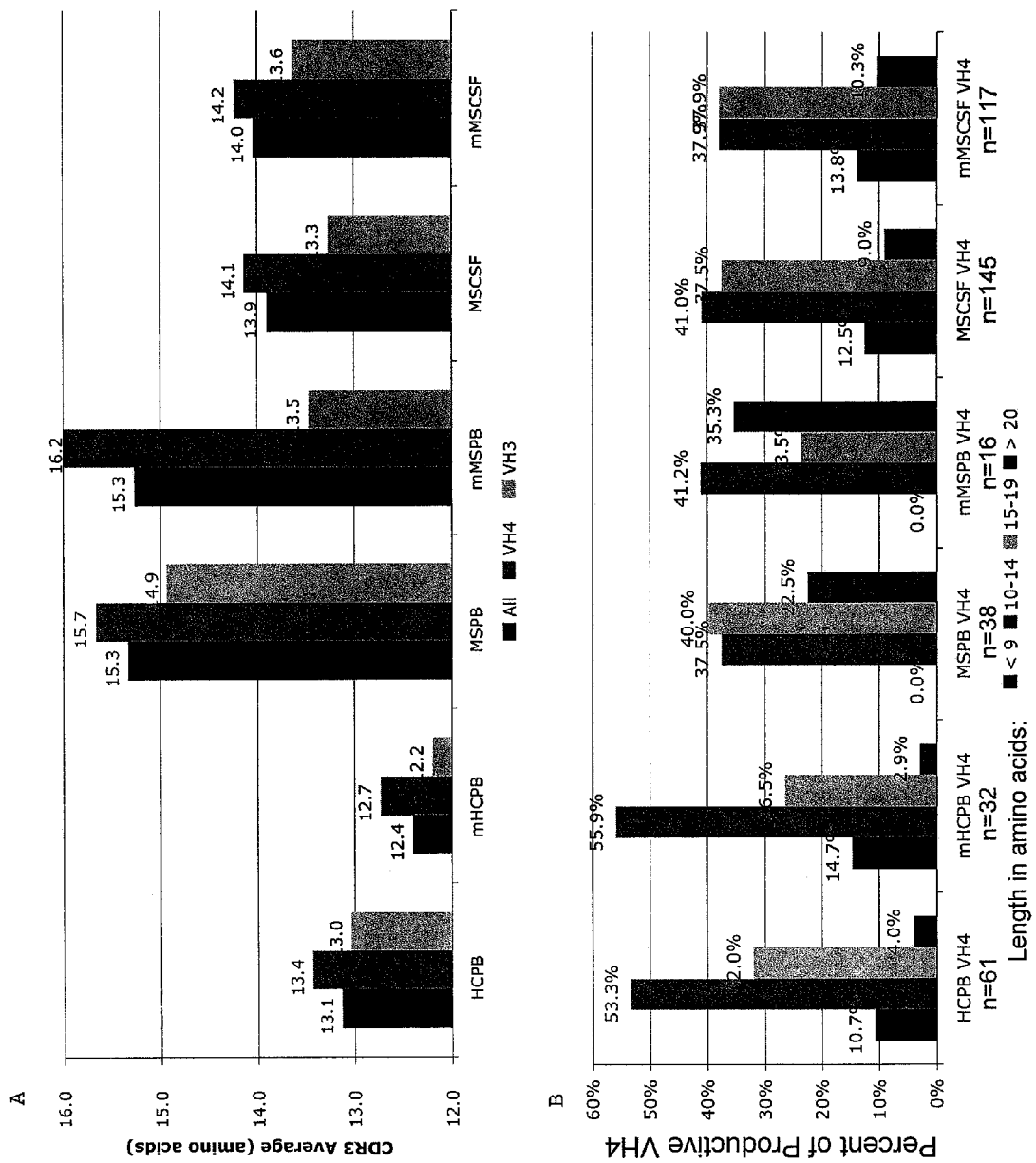
FIGS. 3A-B. CDR3 lengths of productive VH overall repertoire, VH4 subdatabase, and VH3 subdatabase.

MSCSF$_{VH4}$ cells have normal CDR3 length, but MSPB$_{VH4}$ do not. Longer CDR3 lengths have been associated with dysregulation and autoimmunity (Wardemann et al., 2003), so the inventor reasoned that VH4-expressing B cells from MSCSF may have longer CDR3 lengths than the VH4-expressing B cells from HCPB. CDR3 lengths are typically compared among groups by calculating the average length (FIG. 3A); however, different distributions can result in a similar average, so distribution ranges are also useful for comparison (FIG. 3B). HCPB as a whole has a CDR3 length average of 13.1 amino acids, and the VH4 subset has an average of 13.4 amino acids (p>0.05). The mHCPB$_{VH4}$ has a mean of 12.7 and the MSCSF$_{VH4}$, though longer (14.1 amino acids), did not differ statistically from either of these (p>0.05).

In contrast, the CDR3 distribution ranges did differ (FIG. 3B), especially when MSPB or mMSPB were compared to HCPB. For example, MSPB$_{VH4}$ had 22.5% of its sequences in the longest range of >20 amino acids, and HCPB$_{VH4}$ had 4.0% of its sequences in the longest range of >20 amino acids (p<0.003). However, CDR3 lengths>20 amino acids were at a similar frequency in MSCSF and mMSCSF compared to HCPB (9.0% and 10.3% compared to 4.0%, p=0.175 and p=0.111 respectively). This data indicated that MSPB and mMSPB tended towards longer CDR3 lengths more readily than the other groups (including MSCSF), although all groups typically had CDR3 lengths in the range of 10 to 14 amino acids.

Figure 4:
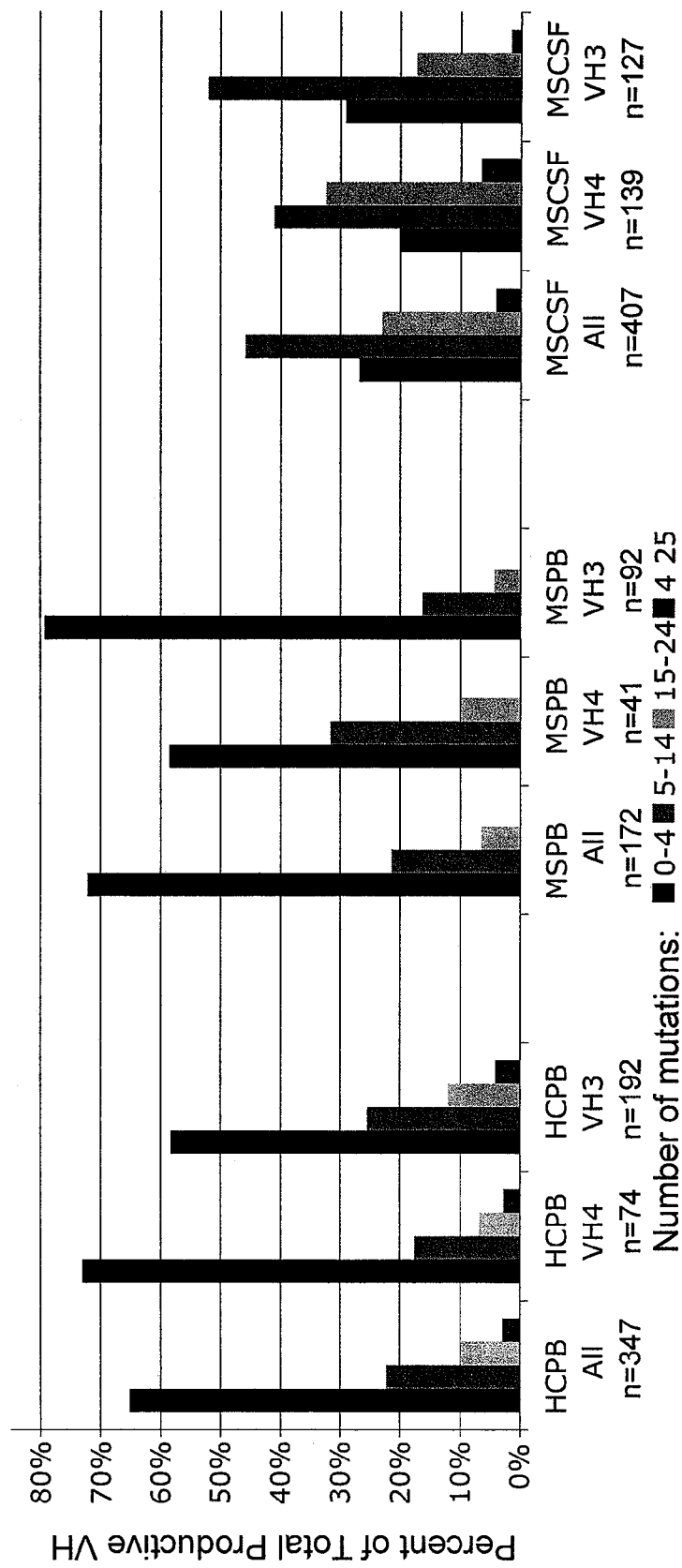
FIG. 4. Ranges of mutational frequency in overall repertoire, VH4 subdatabase, and VH3 subdatabase. Mutations in CDR1, FR2, CDR2, and FR3 were included in the analysis. Since the average read length of VH sequences is 206 nucleotides, the 0-2% range corresponds to 0-4 mutations, the 2-7% range corresponds to 5-14 mutations, the 7-12% range corresponds to 15-24 mutations, and the greater than 12% range corresponds to 25 or more mutations. The number of patients included in each group can be found in the FIGS. 1A-D legend; the number of productive sequences used for analysis in each group is shown in the figure. Data statistics can be found in Table 17.

MSCSF$_{VH4}$ have an increased mutational frequency in comparison to HCPB$_{VH4}$. Previously, the inventor established that the MSCSF B cell database had an enhanced mutational frequency (MF) in comparison to HCPB (Monson et al., 2005. The inventor hypothesized that VH4-expressing CSF-derived B cells would also have a higher mutation frequency than what is observed in the population as a whole, especially considering the increased frequency of VH4-expressing B cells, suggesting local expansion of this population. In order to test this hypothesis, the inventor compared the mutational frequencies of the B cell databases as a whole to the mutational frequencies of the sub-database of only those B cells expressing VH4 genes (Table 3 and FIG. 4). As expected, the inclusive HCPB repertoire has a mutational frequency of 2.3% because the majority of the B cells in this compartment are naïve and, as expected, the memory B cell subpopulation of this database (mHCPB) had a much higher MF (compare 2.3% in HCPB to 5.8% in mHCPB, p<0.001). Interestingly, the VH4-expressing B cell subpopulation of this database (HCPB$_{VH4}$) had a MF of 2.0%, which was significantly less than the MF of the overall repertoire without VH4 (compare 2.0% in HCPB$_{VH4}$ to 2.3% in HCPB$_{All-VH4}$, p<0.02). In contrast, the MSPB$_{VH4}$ and the MSCSF$_{VH4}$ sub-databases had MFs that were statistically greater than the MF of the overall MSPB and MSCSF databases (compare 2.9% in MSPB$_{VH4}$ to 1.7% in MSPB (p<0.001) and 6.0% in MSCSF$_{VH4}$ to 5.0% in MSCSF (p<0.001)). This same pattern was observed when only memory B cells were considered, and is due to the enrichment of CSF B cells with more than 5 mutations per rearrangement (FIG. 4). B cell repertoires from the CIS, Sjögren's, or SLE patient populations were not analyzed in this manner because of the low frequency of VH4 expressing B cells in those repertoires.

MSCSF$_{VH4}$ mutational characteristics retain targeting to CDR and DGYW/WRCH motifs. Mutational characteristics of the antibody variable region can confirm whether appropriate targeting of mutations that are associated with antigenic selection occur within the context of a classic germinal center (Harp et al., 2007). The MSCSF database maintains typical germinal center features including targeting to CDRs and particular motifs within the CDRs (Harp et al., 2007). CSF derived B cell clones from MS patients have more atypical features (Monson et al., 2005), suggesting that some clonally expanded B cells in the CSF are not selected in the context of a classical germinal center. If the B cells expressing VH4 genes are enriched for self-reactive B cells, and these cells are being driven by antigen in the CNS, the VH4 cells may have diminished mutational targeting characteristics rather than the punctuated targeting of mutations associated with classically selected germinal center B cells. To evaluate this, the inventor categorized 4,182 mutations in the MSCSF B cell database and 1,815 mutations in the MSCSF$_{VH4}$ sub-database according to their regional location, amino acid position, whether the mutation resulted in an amino acid change (replacement) or not (silent), and whether the mutation occurred within a motif known to be targeted by the mutational machinery (Rogozin and Diaz, 2004). The combination of these traits indicate whether or not a B cell or population of B cells have been selected in the context of a classical germinal center.

Mutational targeting measured by MF in MSCSF$_{VH4}$ CDR is preserved. Since the CDR is comprised of fewer nucleotides than the FR, mutational frequencies in these regions are a more objective method of evaluating targeting than the percentage of mutations in these regions. As one would expect in a typical germinal center reaction, the MSCSF CDRs have a much higher MF than FRs when the repertoire is considered as a whole (8.0 to 3.1, p<0.001), or when only VH4 expressing CSF-derived B cells are considered (8.8 to 3.9, p<0.001) (Table 3). When only memory MSCSF B cells are considered, the CDR MF is still much higher than the FR MF when the repertoire is considered as a whole (11.8 to 4.6, p<0.001), or when only the mMSCSF$_{VH4}$ sub-database is considered (11.7 to 5.7, p<0.004). This implies that targeting mutations to CDR is preserved in the VH4 expressing B cells from MSCSF.

Replacement:Silent ratios are normal in MSCSF$_{VH4}$. It is well established that replacement mutations within CDRs are favorable as they influence antigen affinity, whilst replacement mutations within FRs are unfavorable as they can affect antibody structure (Kirkham and Schroeder, 1994; Vargas-Madrazo et al., 1994; Both et al., 1990; Tanaka and Nei, 1989). An R:S ratio of 2.9 is considered random (Shlomchik et al., 1987), less than this number is conservation of sequence, and a ratio greater than 2.9 indicates diversification (Shlomchik et al., 1987). As in the HCPB$_{VH4}$, the MSCSF$_{VH4}$ B cells had significant sequence variation in the CDR, but preservation of sequence in the FR (HCPB$_{VH4}$ CDR 6.6, FR 1.3; MSCSF$_{VH4}$ CDR 4.4, FR 1.2) (Table 4).

Targeting to DGYW/WRCH motifs is preserved in MSCSF$_{VH4}$. Somatic hypermutation occurring in the context of a classical germinal center is predominantly targeted to DGYW/WRCH motifs within variable immunoglobulin genes (Rogozin and Diaz, 2004). If VH4 expressing B cells undergo antigen driven selection in the context of a classical germinal center, then targeting to these motifs should be preserved. In order to determine whether appropriate targeting to DGYW/WRCH (abbreviated "DW") motifs occurred in the MSCSF VH4 sub-database in comparison to the VH4 sub-database of the control groups, MFs in the motifs were determined. HCPB$_{VH4}$ B cells had a MF within DW motifs of 3.1%, while the mHCPB$_{VH4}$ B cells had a MF of 9.4% (p<0.001)(Table 4). MSCSF$_{VH4}$ B cells had a MF of 9.0% within DW motifs, which was statistically greater than what was observed in HCPB$_{VH4}$ B cells (p<0.001), equivalent to what was observed in mHCPB (p>0.05).

Mutation position analysis reveals an MS-specific signature in VH4 expressing CSF-derived B cells. Analysis of individual codons' mutation frequencies may possibly reveal a pattern of replacement mutations in the VH4 genes that is unique to the MSCSF database. In order to test this, the mutational frequency at each codon within the MSCSF$_{VH4}$ B cell database was determined and compared to the frequency of random mutation (1.5%) such that any codon with a MF statistically greater than 1.5% was identified as a "hot" spot (Dorner et al., 1997) (Table 5). Previous analysis had identified codon positions 30, 31, 50, 55, 56, 78, 89 and 94 as "hot spots" for replacement mutations in the overall HCPB heavy chain repertoire (Dorner et al., 1997). The VH4 subdatabase of the HCPB database (HCPB$_{VH4}$) includes two of these original hotspots (codons 30 and 56), and 3 additional hotspots for replacement mutations (codons 52, 68, and 81), which were marked as VH4 family biased mutational hot spots (Table 5). Interestingly, one of the three VH4 family biased mutational hotspots is not included within a DGYW/WRCH motif (codon 52), but it has a mutational frequency significantly greater than the random frequency (compare 4.9% to the random frequency of 1.5%, p<0.001).

Five additional positions (codons 31B, 40, 57, 60, and 69) were identified as replacement hot spots in the MSCSF$_{VH4}$ database that were not replacement hot spots in either the HCPB$_{VH4}$ database or overall HCPB databases (Table 18), and are thus specific for MSCSF-derived B cells expressing VH4 antibody genes. Of these MS specific hotspots, 31B is most impressive, demonstrating a 7-fold increase in mutation accumulation in comparison to HCPB. This codon is present in only four of the nine VH4 genes (4-30, 4-31, 4-39, 4-61), and is mutated in 69% of B cells utilizing VH4-61, 46% of B cells utilizing VH4-39, 35% of B cells utilizing VH4-30, and 14% of B cells utilizing VH4-31 (data not shown). Interestingly, VH4-34, the VH4 variable gene associated with autoreactivity in the periphery of healthy controls and SLE patients (Pugh-Bernard et al., 2001; Zheng et al., 2004; Mockridge et al., 2004; Voswinkel et al., 1997), does not contain this codon. Codons 30 and 68 are "cold" spots, in that the MSCSF$_{VH4}$ B cells had replacement mutations at these positions significantly less frequently than in HCPB$_{VH4}$ B cells (Table 5). Codon 52 in the MSCSF$_{VH4}$ database also had an MF that was less than the HCPB$_{VH4}$ database, but still significantly greater than the random frequency. These "hot" and "cold" spots together include 11 codons, and represent 27.8% of the mutations in the MSCSF$_{VH4}$ database (Table 6). These significant changes in codon mutation frequency in the MSCSF$_{VH4}$ database constitute a footprint of mutations that is unique to MS.

TABLE 1

VH4 individual gene usage in peripheral blood

| Genes | HCPB | HCPB Memory | MSPB | MSPB Memory | MSCSF | MSCSF Memory |
|---|---|---|---|---|---|---|
| 4-04 | 7 (9%)[4,5] | 9 (26%) | 4 (10%) | 2 (14%)[7] | 9 (6%)[5] | 3 (3%)[5,6] |
| 4-28 | 0 (0%) | 0 (0%) | 0 (0%) | 0 (0%) | 0 (0%) | 0 (0%) |
| 4-30[1] | 5 (7%)[7] | 2 (6%) | 5 (13%) | 2 (14%) | 26 (18%) | 23 (21%)[5] |
| 4-31 | 4 (5%) | 0 (0%) | 3 (8%) | 1 (7%) | 7 (5%) | 6 (6%) |
| 4-34 | 13 (17%) | 3 (9%) | 4 (10%) | 1 (7%) | 8 (6%) | 5 (5%) |
| 4-39 | 16 (21%) | 6 (17%) | 9 (23%) | 1 (7%) | 35 (24%) | 23 (22%) |
| 4-59 | 24 (32%) | 11 (31%) | 11 (28%) | 5 (36%) | 41 (28%) | 29 (27%) |
| 4-61 | 3 (4%) | 1 (3%) | 2 (5%) | 1 (7%) | 13 (9%) | 12 (11%) |
| 4-B | 4 (5%) | 3 (9%) | 2 (5%) | 1 (7%) | 6 (4%) | 3 (3%) |
| VH4 N[2] | 76 | 35 | 40 | 14 | 145 | 104 |
| Total N[3] | 349 | 205 | 226 | 62 | 405 | 273 |

[1]Includes all sub-genes (4-30.1, 4-30.2, and 4-30.4)
[2]Number of productive VH4 sequences analyzed in each group
[3]Number of productive VH sequences overall
[4]Absolute number (% of total VH4 sequences)
[5]Different from HCPB memory
[6]Different from MSPB memory
[7]Different from MSCSF memory

TABLE 2

VH4 individual gene usage in Sjögren's and SLE B cell autoimmune diseases

| Genes | Sjögren's | SLE | Compared to MSCSF Sjögren's | Compared to MSCSF SLE |
|---|---|---|---|---|
| 4-04 | 3 (14%)[4] | 0 (0%) | = | = |
| 4-28 | 0 (0%) | 0 (0%) | NA[5] | NA[5] |
| 4-30[1] | 2 (10%) | 1 (33%) | = | = |
| 4-31 | 0 (0%) | 0 (0%) | = | = |
| 4-34 | 5 (24%) | 2 (67%) | ↑ p <0.004 | ↑ p <0.002 |
| 4-39 | 0 (0%) | 0 (0%) | ↓ p <0.02 | = |
| 4-59 | 8 (38%) | 0 (0%) | = | = |
| 4-61 | 3 (14%) | 0 (0%) | = | = |
| 4-b | 0 (0%) | 0 (0%) | = | = |
| VH4 N[2] | 21 | 3 | | |
| Total N[3] | 107 | 41 | | |

[1]Includes all sub-genes (4-30.1, 4-30.2, and 4-30.4)
[2]Number of productive VH4 sequences analyzed in each group
[3]Number of productive VH sequences overall
[4]Absolute number (% of total VH4 sequences)
[5]None of the groups had any VH4-28 genes
NA = not applicable

TABLE 3

Mutational Frequency in B cell Repertoires

| All B cells | All Total | All CDR | All FR | CDR vs FR p-value | VH4 Total | VH4 CDR | VH4 FR | CDR vs FR p-value | Total MF All vs VH4 p-value |
|---|---|---|---|---|---|---|---|---|---|
| HCPB | 2.3[1,2,3] | 3.5[1,2,3] | 1.7[1,2,3] | p < 0.001 | 2.0[1,2,3] | 2.4[1,2,3] | 1.9[1,2,3] | p < 0.04 | <0.02[4] |
| MSPB | 1.7[1,2,3] | 3.3[1,2,3] | 1.0[1,2,3] | p < 0.001 | 2.9[1,2,3] | 5.2[1,2,3] | 1.9[1,2,3] | p < 0.001 | <0.001[4] |
| MSCSF | 5.0[1,2,3] | 8.0[1,2,3] | 3.1[1,3] | p < 0.001 | 6.0[3] | 8.8[2,3] | 3.9[1,3] | p < 0.001 | <0.001[4] |
| Memory B cells only | | | | | | | | | |
| mHCPB | 5.8[3] | 9.4[3] | 4.0[2,3] | p < 0.001 | 6.1[3] | 7.7[2,3] | 5.3[2] | p < 0.004 | NS |
| mMSPB | 5.6[3] | 10.5 | 3.3[1,3] | p < 0.001 | 6.3[3] | 11.5[1] | 3.9[1] | p < 0.001 | <0.02[4] |
| mMSCSF | 6.6[1,2] | 11.8[1,2] | 4.6[1,2] | p < 0.001 | 7.3[1,2] | 11.7[1] | 5.7[2] | p < 0.001 | <0.001[4] |

[1]Different from HCPB memory ($p \leq 0.05$)
[2]Different from MSPB memory ($p \leq 0.05$)
[3]Different from MSCSF memory ($p \leq 0.05$)
[4]Comparing All without VH4 to VH4
NS = not significant

TABLE 4

VH4 Mutational Characteristics

| | HCPB | mHCPB[5] | CSPB[5] | MSCSF |
|---|---|---|---|---|
| R:S Ratio CDR | 6.6[3] | 6.9[3] | 3.0[1,2] | 4.4 |
| R:S Ratio FR | 1.3 | 1.5 | 1.8 | 1.2[3] |
| DW Motifs MF Total | 3.1%[2,3,4] | 9.4%[1] | 15.1%[1,2,4] | 9.0%[1,3] |
| DW Motifs MF CDR | 2.5%[2,3,4] | 7.7%[1] | 15.7%[1,2] | 10.4%[1,2,3] |
| DW Motifs MF FR | 3.6%[2,3,4] | 10.8%[1] | 14.6%[1,2] | 7.8%[1,2,3] |

[1]Different from HCPB VH4 ($p \leq 0.05$)
[2]Different from mHCPB VH4 ($p \leq 0.05$)
[3]Different from CSPB VH4 ($p \leq 0.05$)
[4]Different from MSCSF VH4 ($p \leq 0.05$)
[5]mHCPB separated into those defined by MF >2% (mHCPB) and those defined by IgG⁺ CD27⁺ expression (CSPB)

TABLE 5

VH4 R Mutational Frequencies at Codon Hot Spots

| Codon | Location[2] | DGYW Motif | HCPB | MSCSF | MSCSF to HCPB |
|---|---|---|---|---|---|
| 30[1] | FR1 | Y | 3.8% | 1.9% | ↓ $p<0.005$ |
| 31B | CDR1 | Y | 0.5% | 3.5% | ↑ $p<0.001$ |
| 40 | FR2 | Y | 1.1% | 2.6% | ↑ $p<0.001$ |
| 52 | CDR2 | N | 4.9% | 2.7% | ↓ $p<0.005$ |
| 56[1] | CDR2 | Y | 2.8% | 5.4% | ↑ $p<0.001$ |
| 57 | CDR2 | Y/N[3] | 1.1% | 2.0% | ↑ $p<0.01$ |
| 60 | CDR2 | Y | 1.1% | 2.4% | ↑ $p<0.001$ |
| 68 | FR3 | N | 2.2% | 1.2% | ↓ $p<0.05$ |
| 69 | FR3 | N | 1.1% | 2.0% | ↑ $p<0.01$ |
| 81 | FR3 | Y | 2.7% | 4.6% | ↑ $p<0.001$ |
| 89[1] | FR3 | Y | 1.1% | 2.0% | ↑ $p<0.01$ |

[1]Previously published hotspot (Dorner et al., 1997) also in VH4 signature
[2]As defined by Kabat
[3]Nucleotide position 1 is within a DW motif, but not nucleotide positions 2 and 3.

TABLE 6

MSCSF VH4 R Mutation Frequencies at Codon Hot Spots

| | 4-04 | 4-30[a] | 4-31 | 4-34 | 4-39 | 4-59 | 4-61 | 4-b | Total[d] |
|---|---|---|---|---|---|---|---|---|---|
| % total VH4 mutations[b] | 2% | 21% | 5% | 5% | 18% | 31% | 16% | 2% | 1184 |
| % total VH4 use | 6% | 18% | 5% | 6% | 24% | 28% | 9% | 4% | 145 |
| 30 | 3.8%[e] | 0.8%[e] | 1.5%[e] | 4.6%[e] | 2.3%[e] | 1.9%[e] | 1.1%[e] | 0.0%[e] | ↓ 1.9%[d] |
| 31B | NA[c] | 3.7% | 1.6% | NA[c] | 7.5% | NA[c] | 4.9% | NA[c] | ↑ 3.5%[d] |

TABLE 6-continued

MSCSF VH4 R Mutation Frequencies at Codon Hot Spots

| | | | | | | | | | |
|---|---|---|---|---|---|---|---|---|---|
| 40 | 0.0% | 3.3% | 3.2% | 6.2% | 2.3% | 1.9% | 0.0% | 0.0% | |
| 52 | 3.8% | 2.1% | 4.8% | 3.1% | 2.8% | 2.2% | 3.8% | 3.8% | 2.6%[d] |
| 56 | 3.8% | 6.2% | 4.8% | 3.1% | 5.6% | 2.8% | 4.9% | 7.7% | 2.7%[d] |
| 57 | 3.8% | 1.2% | 0.0% | 6.2% | 2.3% | 1.1% | 2.2% | 3.8% | 5.4%[d] |
| 60 | 3.8% | 2.5% | 4.8% | 0.0% | 1.9% | 1.4% | 3.2% | 0.0% | 2.0%[d] |
| 68 | 0.0% | 2.5% | 1.6% | 1.5% | 0.0% | 0.8% | 0.5% | 0.0% | 2.4%[d] |
| 69 | 0.0% | 0.8% | 0.0% | 3.1% | 2.3% | 3.6% | 0.5% | 3.8% | 1.2%[d] |
| 81 | 11.5% | 4.9% | 6.3% | 4.6% | 5.6% | 2.2% | 4.3% | 7.7% | 2.0%[d] |
| 89 | 3.8% | 0.0% | 3.2% | 4.6% | 1.9% | 1.9% | 3.2% | 7.7% | 4.6%[d] |
| Total[f] | 34.6% | 28.0% | 31.7% | 36.9% | 34.6% | 19.9% | 28.6% | 34.6% | 2.0%[d] 27.8% |

[a]4-30 includes all sub-genes

[b]Percent of total R mutations in each gene

[c]Gene does not contain codon 31 B

[d]Overall VH4 mutational frequency (see Table 7)

[e]Percent of total mutations found in this gene are at this location

[f]Percent of total R mutations of the gene represented in footprint

TABLE 7

MS Patient Summary[1]

| | M125[2,3] | M199 | M217 | M354[2,3] | M368[2,3] | M376[3] | M484[2,3] | M522[3] | M584[3] | M875[2,3] | M887 | MS02-19[4,5] | MS02-24[4,5] |
|---|---|---|---|---|---|---|---|---|---|---|---|---|---|
| Type of MS | RR | RR | RR | RR | RR | RR | PP | RR | RR | RR | RR | PP | SP |
| Time since MS diagnosis | <1 year | 4 months | 18 years | <1 year | 15 years | 20 years | 3 months | 3 years | | 1 month | 13 years | 3 years | 20 years |
| Age/Sex | 32/F | 26/F | 45/F | 44/F | 41/F | 56/F | 46/F | 35/F | 44/F | 35/F | 50/F | 46/F | 39/F |
| Exacerbation History | ON | paresthesias | dystonia | TM | TM | ON | myelitis | TM | TM | ON | ON | NR | NR |
| MRI Findings | GD+ | GD+ | WML | WML | WML | WML | WML | GD+ WML | GD+ | GD+, WML | WML | WML | WML |
| Clonal Expansion | Yes | Yes | n.d. | Yes | Yes | Yes | Yes | Yes | Yes | Yes | No | Yes | Yes |
| Oligoclonal Bands | No | n.d. | n.d. | Yes | Yes | No | Yes | Yes | n.d. | n.d. | No | Yes | Yes |
| Ig Index | NL | n.d. | High | NL | High | n.d. | High | High | n.d. | n.d. | NL | High | High |
| Ig Synthesis | n.d. | n.d. | n.d. | NL | High | n.d. | High | n.d. | n.d. | n.d. | NL | High | High |

TABLE 7-continued

MS Patient Summary[1]

| | M125[2,3] | M199 | M217 | M354[2,3] | M368[2,3] | M376[3] | M484[2,3] | M522[3] | M584[3] | M875[2,3] | M887 | MS02-19[4,5] | MS02-24[4,5] |
|---|---|---|---|---|---|---|---|---|---|---|---|---|---|
| No. Productive VH Sequences | 100 CSF 76 PB | 19 | 1 | 6 CSF 19 PB | 49 | 8 | 10 CSF 77 PB | 71 | 85 | 21 | 3 | 25/21[6] | 10/66[6] |

RR, Relapsing Remitting;
SP, Secondary Progressive;
ON, Optic Neuritis;
TM, Transverse Myelitis;
GD+, gadolinium enhancing;
WML, White Matter Lesions;
NR, not reported;
n.d., not done;
NL, normal
[1]All patients had CSF white blood cell (WBC) counts in the range of $1 \times 10^3$ to $1 \times 10^4$ per mL, typical of MS patients at UTSWMC (Stuve et al., 2006)
[2]Patient clonal analysis previously published in Monson et al. (2005)
[3]Patient repertoire or mutational analysis previously published in Harp et al. (2007)
[4]Patient data not used in mutational signature analysis
[5]Patient repertoire and clonal analysis previously published in Ritchie et al. (2004)
[6]CD19+/CD138+ CSF-derived B cells

TABLE 8

OND Patient Summary[1]

| | CIS 132[4] | CIS 429[2] | CIS03-01[5] | OND 341[4] | OND 758[4] | Sjögren's[6] | SLE[7] | HC |
|---|---|---|---|---|---|---|---|---|
| OND subcategory | CIS | CIS | CIS | OIND | NIND | NA | NA | NA |
| Age/Sex | 24/F | 62/M | 25/F | 70/M | 45/F | 76/F | 54/M | 26/M; 45/M |
| Presentation or Diagnosis at time of sampling | Diplopia | Optic Neuritis | Not reported | Ataxia, PS | HA | NA | NA | NA |
| MRI Findings | GD+ | GD+ | WML | No Lesions | WML | ND | ND | ND |
| Clonal Expansion | No | Yes | Yes | No | Yes | Yes | Yes | No |
| No. Productive VH Sequences | 19 | 57 | 24/67 | 32 | 19 | 107 | 41 | 314 |

Abbreviations:
OND; Other Neurological Disease,
CIS; Clinically Isolated Syndrome,
NIND; non-inflammatory neurological disease,
OIND; Other Inflammatory Neurological Disease,
HA; Headache,
PS; Paraneoplastic Syndrome,
GD+; Gadolinium Enhancing,
WML; White Matter Lesions
[1]All patients had CSF white blood cell (WBC) counts typical of OND controls at UTSWMC (Stuve et al., 2006)
[2]This patient converted to CDMS according to the Poser Criteria 18 months after sampling.
[3]This patient's CSF analysis was negative for oligoclonal bands, and normal for Ig synthesis and rate.
[4]Patient repertoire or mutational analysis previously published in Harp et al. (2007)
[5]This patient converted to CDMS subsequent to this episode, and was published in Ritchie et al. (2004)
[6]This patient's repertoire analysis previously published in Hansen et al. (2003)
[7]This patient's repertoire analysis previously published in Hansen et al. (2000); Dorner et al. (1999)
[8]CD19+/CD138+ CSF-derived B cells

TABLE 9

VH Family Usage Statistics for FIG. 1A

| | | % | Different from HCPB | Different from mHCPB | Different from MSPB | Different from MSCSF |
|---|---|---|---|---|---|---|
| HCPB n = 349 | VH1 | 15.5% | X | N | N | Y |
| | VH2 | 2.0% | X | N | N | N |
| | VH3 | 55.0% | X | N | N | Y |
| | VH4 | 21.8% | X | N | N | Y |
| | VH567 | 5.7% | X | N | N | N |
| mHCPB n = 205 | VH1 | 10.7% | N | X | Y | Y |
| | VH2 | 2.0% | N | X | N | N |
| | VH3 | 61.5% | N | X | N | Y |
| | VH4 | 16.6% | N | X | N | Y |
| | VH567 | 9.3% | N | X | Y | Y |

TABLE 9-continued

VH Family Usage Statistics for FIG. 1A

| | % | Different from HCPB | Different from mHCPB | Different from MSPB | Different from MSCSF |
|---|---|---|---|---|---|
| MSPB n = 226 | VH1 19.9% | N | Y | X | N |
| | VH2 1.3% | N | N | X | N |
| | VH3 56.6% | N | N | X | Y |
| | VH4 17.7% | N | N | X | Y |
| | VH567 4.4% | N | Y | X | N |
| mMSPB n = 62 | VH1 24.2% | N | N | N | N |
| | VH2 1.6% | N | N | N | N |
| | VH3 45.2% | N | Y | N | Y |
| | VH4 22.6% | N | N | N | Y |
| | VH567 6.5% | N | N | N | N |

X = Not applicable; comaparing to self
N = p > 0.05
Y = p ≦ 0.05

TABLE 10

VH Family Usage Statistics for FIG. 1B

| | % | Different from HCPB | Different from mHCPB | Different from MSPB | Different from MSCSF |
|---|---|---|---|---|---|
| MSCSF n = 405 | VH1 25.2% | Y | Y | N | X |
| | VH2 3.2% | N | N | N | X |
| | VH3 31.4% | Y | Y | Y | X |
| | VH4 35.8% | Y | Y | Y | X |
| | VH567 4.4% | N | Y | N | X |
| mMSCSF n = 283 | VH1 24.9% | Y | Y | N | N |
| | VH2 1.8% | N | N | N | N |
| | VH3 31.9% | Y | Y | Y | N |
| | VH4 38.1% | Y | Y | Y | N |
| | VH567 3.3% | N | Y | N | N |
| MSCSF Normalized n = 286 | VH1 23.1% | Y | Y | N | N |
| | VH2 1.7% | N | N | N | N |
| | VH3 32.9% | Y | Y | Y | N |
| | VH4 36.7% | Y | Y | Y | N |
| | VH567 5.6% | N | N | N | N |
| MSCSF CD138 n = 87 | VH1 2.3% | Y | N | Y | Y |
| | VH2 6.9% | Y | Y | Y | N |
| | VH3 24.1% | Y | Y | Y | N |
| | VH4 66.7% | Y | Y | Y | Y |
| | VH567 0.0% | Y | Y | Y | Y |

X = Not applicable; comparing to self;
N = p > 0.05;
Y = p ≦ 0.05

TABLE 11

VH Family Usage Statistics for FIG. 1C

| | % | Different from HCPB | Different from mHCPB | Different from MSPB | Different from MSCSF |
|---|---|---|---|---|---|
| CISCSF n = 100 | VH1 2.0% | Y | Y | Y | Y |
| | VH2 2.0% | N | N | N | N |
| | VH3 72.0% | Y | N | Y | Y |
| | VH4 22.0% | N | N | N | Y |
| | VH567 2.0% | N | Y | N | N |
| mCISCSF n = 87 | VH1 0.0% | Y | N | Y | Y |
| | VH2 0.0% | N | N | N | N |
| | VH3 74.5% | Y | N | Y | Y |
| | VH4 23.6% | N | N | N | N |
| | VH567 1.8% | N | N | N | N |
| CISCSF CD138 n = 76 | VH1 0.0% | Y | Y | Y | Y |
| | VH2 5.3% | N | N | Y | N |
| | VH3 52.6% | N | N | N | Y |
| | VH4 42.1% | Y | Y | Y | N |
| | VH567 0.0% | Y | Y | N | N |

N = p > 0.05;
Y = p ≦ 0.05

TABLE 12

VH Family Usage Statistics for FIG. 1D

| | % | Different from HCPB | Different from mHCPB | Different from MSPB | Different from MSCSF |
|---|---|---|---|---|---|
| ONDCSF n = 51 | VH1 17.6% | N | N | N | N |
| | VH2 3.9% | N | N | N | N |
| | VH3 52.9% | N | N | N | Y |
| | VH4 17.6% | N | N | N | Y |
| | VH567 7.8% | N | N | N | N |
| Sjogren's Parotid n = 107 | VH1 24.3% | Y | Y | N | N |
| | VH2 4.7% | N | N | N | N |
| | VH3 41.1% | Y | Y | Y | N |
| | VH4 19.6% | N | N | N | Y |
| | VH567 10.3% | N | N | Y | Y |
| SLEPB n = 41 | VH1 2.4% | Y | N | Y | Y |
| | VH2 7.3% | Y | N | Y | N |
| | VH3 82.9% | Y | Y | Y | Y |
| | VH4 7.3% | Y | N | N | Y |
| | VH567 0.0% | N | Y | N | N |

N = p > 0.05;
Y = p ≦ 0.05

TABLE 13

J Segment Usage Statistics for FIG. 2

| | % | Different from HCPB | Different from mHCPB | Different from MSPB | Different from MSCSF |
|---|---|---|---|---|---|
| HCPB VH4 n = 78 | JH1 1.3% | X | N | N | N |
| | JH2 5.1% | X | N | N | N |
| | JH3 7.7% | X | N | N | N |
| | JH4 57.7% | X | N | Y | Y |
| | JH5 11.5% | X | N | N | Y |
| | JH6 16.7% | X | N | Y | N |
| mHCPB VH4 n = 35 | JH1 0.0% | N | X | NA | N |
| | JH2 0.0% | N | X | NA | N |
| | JH3 11.4% | N | X | N | N |
| | JH4 57.1% | N | X | N | N |
| | JH5 20.0% | N | X | N | N |
| | JH6 11.4% | N | X | Y | N |
| MSPB VH4 n = 40 | JH1 0.0% | N | NA | X | N |
| | JH2 0.0% | N | NA | X | N |
| | JH3 10.0% | N | N | X | N |
| | JH4 35.0% | Y | N | X | N |
| | JH5 15.0% | N | N | X | N |
| | JH6 40.0% | Y | Y | X | Y |
| mMSPB VH4 n = 17 | JH1 0.0% | N | NA | NA | N |
| | JH2 0.0% | N | NA | NA | N |
| | JH3 11.8% | N | N | N | N |
| | JH4 29.4% | Y | N | N | N |
| | JH5 0.0% | N | Y | N | Y |
| | JH6 58.8% | Y | Y | N | Y |
| MSCSF VH4 n = 144 | JH1 4.9% | N | N | N | X |
| | JH2 6.3% | N | N | N | X |
| | JH3 11.1% | N | N | N | X |
| | JH4 40.3% | Y | N | N | X |
| | JH5 22.9% | Y | N | N | X |
| | JH6 14.6% | N | N | Y | X |

TABLE 13-continued

J Segment Usage Statistics for FIG. 2

| | | % | Different from HCPB | Different from mHCPB | Different from MSPB | Different from MSCSF |
|---|---|---|---|---|---|---|
| mMSCF VH4 n = 116 | JH1 | 6.0% | N | N | N | N |
| | JH2 | 6.9% | N | N | N | N |
| | JH3 | 12.9% | N | N | N | N |
| | JH4 | 40.5% | Y | N | N | N |
| | JH5 | 19.8% | N | N | N | N |
| | JH6 | 13.8% | N | N | Y | N |

X = Not applicable; comparing to self;
NA = Not applicable; comparing 0% to 0%;
N = $p > 0.05$;
Y = $p \leq 0.05$

TABLE 14

Figure 6:
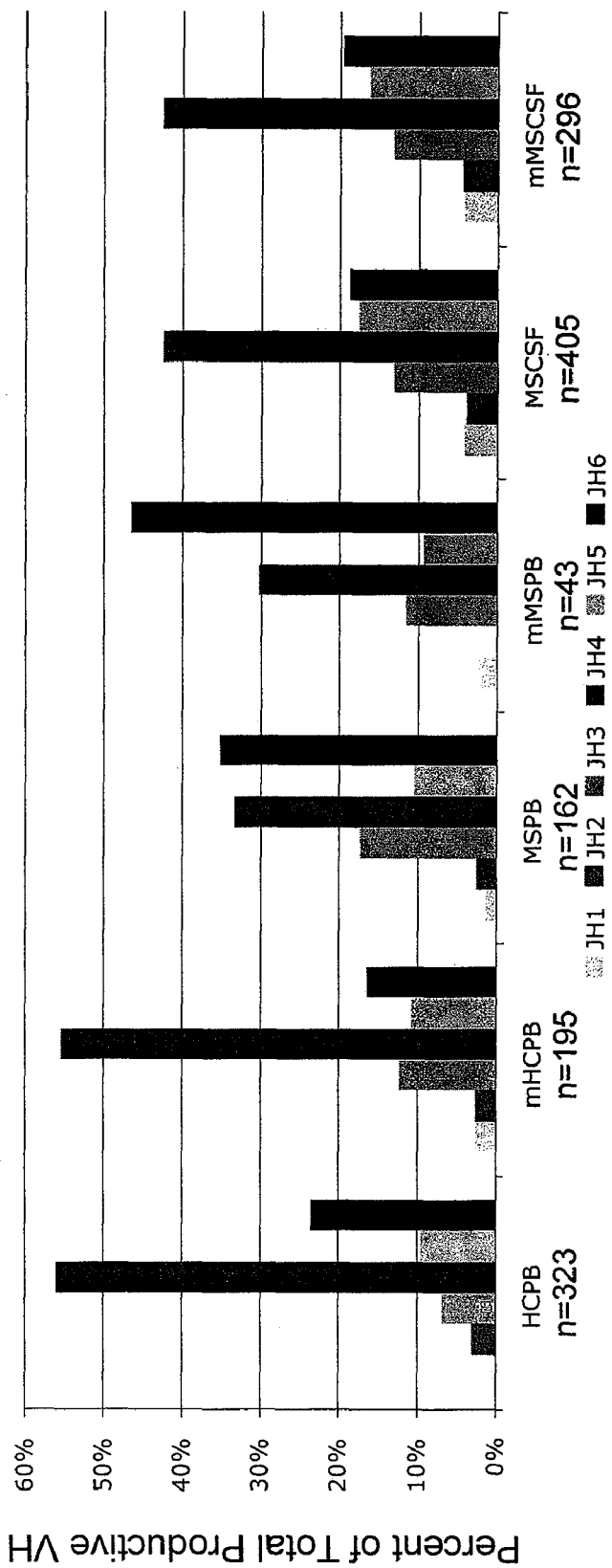
FIG. 6. Frequency of J segment usage in overall repertoire of productive B cell rearrangements. CD19+ B cells expressing a productive rearrangement were isolated from HCPB, MSPB, and MSCSF and analyzed for J segment usage. The number of patients included in each group can be found in the FIGS. 1A-D legend; the number of productive sequences in each group is shown in the figure. Data statistics can be found in Table 15.

J Segment Usage Statistics for FIG. 6

| | | % | Different from HCPB | Different from mHCPB | Different from MSPB | Different from MSCSF |
|---|---|---|---|---|---|---|
| HCPB n = 323 | JH1 | 0.9% | X | N | N | Y |
| | JH2 | 3.1% | X | N | N | N |
| | JH3 | 6.8% | X | Y | Y | Y |
| | JH4 | 56.0% | X | N | Y | Y |
| | JH5 | 9.6% | X | N | N | Y |
| | JH6 | 23.5% | X | N | Y | N |
| mHCPB n = 195 | JH1 | 2.6% | N | X | N | N |
| | JH2 | 2.6% | N | X | N | N |
| | JH3 | 12.3% | Y | X | N | N |
| | JH4 | 55.4% | N | X | Y | Y |
| | JH5 | 10.8% | N | X | N | Y |
| | JH6 | 16.4% | N | X | Y | N |
| MSPB n = 162 | JH1 | 1.2% | N | N | X | N |
| | JH2 | 2.5% | N | N | X | N |
| | JH3 | 17.3% | Y | N | X | N |
| | JH4 | 33.3% | Y | Y | X | Y |
| | JH5 | 10.5% | N | N | X | Y |
| | JH6 | 35.2% | Y | Y | X | Y |
| mMSPB n = 43 | JH1 | 2.3% | N | N | N | N |
| | JH2 | 0.0% | N | N | N | N |
| | JH3 | 11.6% | N | N | N | N |
| | JH4 | 30.2% | Y | Y | N | N |
| | JH5 | 9.3% | N | N | N | N |
| | JH6 | 46.5% | Y | Y | N | Y |
| MSCSF n = 405 | JH1 | 4.2% | Y | N | N | X |
| | JH2 | 4.0% | N | N | N | X |
| | JH3 | 13.1% | Y | N | N | X |
| | JH4 | 42.5% | Y | Y | Y | X |
| | JH5 | 17.5% | Y | Y | Y | X |
| | JH6 | 18.8% | N | N | Y | X |
| mMSCF n = 296 | JH1 | 4.1% | Y | N | N | N |
| | JH2 | 4.4% | N | N | N | N |
| | JH3 | 13.2% | Y | N | N | N |
| | JH4 | 42.6% | Y | Y | N | N |
| | JH5 | 16.2% | Y | N | N | N |
| | JH6 | 19.6% | N | N | Y | N |

X = Not applicable; comparing to self;
NA = Not applicable; comparing 0% to 0%;
N = $p > 0.05$;
Y = $p \leq 0.05$

TABLE 15

CDR3 Average Statistics for FIG. 3A

| | Average amino acid length | Different from HCPB | Different from mHCPB | Different from MSPB | Different from mMSPB | Different from MSCSF | Different from mMSCSF |
|---|---|---|---|---|---|---|---|
| HCPB All n = 348 | All 13.1 | X | Y | Y | Y | Y | Y |
| HCPB VH4 n = 76 | VH4 13.4 | X | N | N | N | N | N |
| HCPB VH3 n = 192 | VH3 13.0 | X | N | Y | N | N | N |
| mHCPB All n = 205 | All 12.4 | Y | X | Y | Y | Y | Y |
| mHCPB VH4 n = 34 | VH4 12.7 | N | X | Y | N | N | N |
| mHCPB VH3 n = 127 | VH3 12.2 | N | X | Y | N | N | N |
| MSPB All n = 168 | All 15.3 | Y | Y | X | Y | Y | Y |
| MSPB VH4 n = 40 | VH4 15.7 | N | Y | X | N | N | N |

TABLE 15-continued

| | CDR3 Average Statistics for FIG. 3A | | | | | | |
|---|---|---|---|---|---|---|---|
| | Average amino acid length | Different from HCPB | Different from mHCPB | Different from MSPB | Different from mMSPB | Different from MSCSF | Different from mMSCSF |
| MSPB VH3 n = 89 | VH3 14.9 | Y | Y | X | N | Y | N |
| mMSPB All n = 45 | All 15.3 | Y | Y | Y | X | Y | Y |
| mMSPB VH4 n = 17 | VH4 16.2 | N | N | N | X | N | N |
| mMSPB VH3 n = 16 | VH3 13.5 | N | N | N | X | N | N |
| MSCSF All n = 405 | All 13.9 | Y | Y | Y | Y | X | Y |
| MSCSF VH4 n = 144 | VH4 14.1 | N | N | N | N | X | N |
| MSCSF VH3 n = 129 | VH3 13.3 | N | N | Y | N | X | N |
| mMSCSF All n = 297 | All 14.0 | Y | Y | Y | Y | Y | X |
| mMSCSF VH4 n = 116 | VH4 14.2 | N | N | N | N | N | X |
| mMSCSF VH3 n = 91 | VH3 13.6 | N | N | N | N | N | X |

X = Not applicable; comparing to self;
N = p > 0.05;
Y = p ≦ 0.05

TABLE 16

| | | CDR3 Length Range Statistics for FIG. 3B | | | | | |
|---|---|---|---|---|---|---|---|
| | % | Different from HCPB | Different from mHCPB | Different from MSPB | Different from mMSPB | Different from MSCSF | Different from mMSCSF |
| HCPB VH4 | ≦9 11.5% | X | N | Y | N | N | N |
| | 10-14 54.1% | X | N | N | N | N | N |
| | 15-19 29.5% | X | N | N | N | N | N |
| | ≧20 4.9% | X | N | Y | Y | N | N |
| mHCPB VH4 | ≦9 12.5% | N | X | Y | N | N | N |
| | 10-14 56.3% | N | X | N | N | N | N |
| | 15-19 28.1% | N | X | N | N | N | N |
| | ≧20 3.1% | N | X | Y | Y | N | N |
| MSPB VH4 | ≦9 90.0% | Y | Y | X | NA | Y | Y |
| | 10-14 39.5% | N | N | X | N | N | N |
| | 15-19 36.8% | N | N | X | N | N | N |
| | ≧20 23.7% | Y | Y | X | N | Y | Y |
| mMSPB VH4 | ≦9 90.0% | N | N | NA | X | N | N |
| | 10-14 37.5% | N | N | N | X | N | N |
| | 15-19 25.0% | N | N | N | X | N | N |
| | ≧20 37.5% | Y | Y | N | X | Y | Y |
| MSCSF VH4 | ≦9 13.1% | N | N | Y | N | X | N |
| | 10-14 44.1% | N | N | N | N | X | N |
| | 15-19 35.2% | N | N | N | N | X | N |
| | ≧20 7.6% | N | N | Y | Y | X | N |

TABLE 16-continued

CDR3 Length Range Statistics for FIG. 3B

| | % | Different from HCPB | Different from mHCPB | Different from MSPB | Different from mMSPB | Different from MSCSF | Different from mMSCSF |
|---|---|---|---|---|---|---|---|
| mMSCSF VH4 | ≦9 14.5% | N | N | Y | N | N | X |
| | 10-14 40.2% | N | N | N | N | N | X |
| | 15-19 36.8% | N | N | N | N | N | X |
| | ≧20 8.5% | N | N | Y | Y | N | X |

X = Not applicable; comparing to self;
NA = Not applicable; comparing 0% to 0%;
N = p > 0.05;
Y = p ≦ 0.05

TABLE 17

MF Range Statistics for FIG. 4

| | % | Different from HCPB All | Different from HCPB VH4 | Different from MSPB All | Different from MSPB VH4 | Different from MSCSF All | Different from MSCSF VH4 |
|---|---|---|---|---|---|---|---|
| HCPB All n = 347 | 0-4 65.0% | X | N | N | N | Y | Y |
| | 5-14 22.3% | X | N | N | N | Y | Y |
| | 15-24 9.7% | X | N | N | N | Y | Y |
| | ≧25 2.9% | X | N | Y | N | N | N |
| HCPB VH4 n = 74 | 0-4 73.0% | N | X | N | N | Y | Y |
| | 5-14 17.6% | N | X | N | N | Y | Y |
| | 15-24 6.8% | N | X | N | N | Y | Y |
| | ≧25 2.7% | N | X | Y | N | N | N |
| HCPB VH3 n = 192 | 0-4 58.3% | N | Y | Y | N | Y | Y |
| | 5-14 25.5% | N | N | N | N | Y | Y |
| | 15-24 12.0% | N | N | N | N | Y | Y |
| | ≧25 4.2% | N | N | Y | N | N | N |
| MSPB All n = 172 | 0-4 72.1% | N | N | X | N | Y | Y |
| | 5-14 21.5% | N | N | X | N | Y | Y |
| | 15-24 6.4% | N | N | X | N | Y | Y |
| | ≧25 0.0% | Y | Y | X | NA | Y | Y |
| MSPB VH4 n = 41 | 0-4 58.5% | N | N | N | X | Y | Y |
| | 5-14 31.7% | N | N | N | X | N | N |
| | 15-24 9.8% | N | N | N | X | Y | Y |
| | ≧25 0.0% | N | N | NA | X | N | N |
| MSPB VH3 n = 92 | 0-4 79.3% | Y | N | N | Y | Y | Y |
| | 5-14 16.3% | N | N | N | Y | Y | Y |
| | 15-24 4.3% | N | N | N | N | Y | Y |
| | ≧25 0.0% | N | N | NA | NA | Y | Y |
| MSCSF All n = 407 | 0-4 26.8% | Y | Y | Y | Y | X | N |
| | 5-14 45.9% | Y | Y | Y | N | X | N |
| | 15-24 23.1% | Y | Y | Y | Y | X | Y |
| | ≧25 4.2% | N | N | Y | N | X | N |
| MSCSF VH4 n = 139 | 0-4 20.1% | Y | Y | Y | Y | N | X |
| | 5-14 41.0% | Y | Y | Y | N | N | X |
| | 15-24 32.4% | Y | Y | Y | Y | Y | X |
| | ≧25 6.5% | N | N | Y | N | N | X |
| MSCSF VH3 n = 127 | 0-4 29.1% | Y | Y | Y | Y | N | N |
| | 5-14 52.0% | Y | Y | Y | Y | N | N |
| | 15-24 17.3% | Y | Y | Y | N | N | Y |
| | ≧25 1.6% | N | N | N | N | N | Y |

X = Not applicable; comparing to self;
NA = Not applicable; comparing 0% to 0%;
N = p > 0.05;
Y = p ≦ 0.05

TABLE 18

VH4 Mutation Frequencies at Codon Hot Spots

| Codon | HCPB ALL | HCPB VH4 | MSCSF ALL | MSCSF VH4 | MSCSF to HCPB VH4 | MSPB VH4 | MSCSF to MSPB VH4 | MSPB to HCPB ALL |
|---|---|---|---|---|---|---|---|---|
| 30 | 2.3% | 3.8% | 2.9% | 1.9% | ↓ $p<0.005$ | 1.8% | = | = |
| 31B | 0.3% | 0.5% | 1.4% | 3.5% | ↑ $p<0.001$ | 3.6% | = | ↑ $p<0.001$ |
| 40 | 0.7% | 1.1% | 1.5% | 2.6% | ↑ $p<0.001$ | 0% | X | = |
| 52 | 2.5% | 4.9% | 2.7% | 2.7% | ↓ $p<0.005$ | 5.5% | ↓ $p<0.001$ | ↑ $p<0.001$ |
| 56 | 4.6% | 2.8% | 4.6% | 5.4% | ↑ $p<0.001$ | 2.7% | ↓ $p<0.001$ | = |
| 57 | 2.1% | 1.1% | 3.2% | 2.0% | ↑ $p<0.01$ | 0% | X | = |
| 60 | 1.3% | 1.1% | 1.6% | 2.4% | ↑ $p<0.001$ | 0% | X | = |
| 68 | 1.4% | 2.2% | 1.0% | 1.2% | ↓ $p<0.05$ | 0.9% | = | = |
| 69 | 1.2% | 1.1% | 1.3% | 2.0% | ↑ $p<0.01$ | 3.6% | ↓ $p<0.01$ | = |
| 81 | 0.8% | 2.7% | 2.5% | 4.6% | ↑ $p<0.001$ | 3.6% | = | = |
| 89 | 1.3% | 1.1% | 2.1% | 2.0% | ↑ $p<0.01$ | 1.8% | = | = |

[1] MF at this position greater in VH4 than ALL
[2] MF at this position less in VH4 than ALL
[3] MF at this position is greater in MSCSF than HCPB
[4] MF at this position is less in MSCSF than HCPB

Example 3

Materials and Methods

Patient description. CSF was collected from 10 RRMS patients, one PPMS patient (M484), three patients with other neurological diseases (OND341, ataxia; OND758, headache, and OND116, chronic inflammatory demyelinating polyneuropathy), and two patients with one demyelinating event suggestive of MS (i.e., Clinically Isolated Syndrome (CIS)) at UT Southwestern Medical Center (UTSWMC) (Harp et al., 2007; Monson et al., 2005) in accordance with the UTSWMC Institutional Review Board (IRB). CSF was collected from nine patients with CIS at University of Colorado Denver (UCD) as previously described (Bennett et al., 2008) in accordance with the UCD IRB. The CIS patients had a single episode of demyelination (optic neuritis, brainstem or spinal cord syndrome), and the majority had multiple lesions on MRI satisfying the dissemination in space criterion of the McDonald criteria. None of the patients had received immunomodulatory agents for at least 1 month prior to lumbar puncture. A second relapse confirming a multiple sclerosis diagnosis had not occurred at the time of sample acquisition, thus not fulfilling the dissemination in time criterion (McDonald et al., 2001; Polman et al., 2005). Subsequent diagnosis of definite MS was made using the revised McDonald criteria (Polman et al., 2005). Conversion to definite MS was not revealed to the antibody sequence analysis team until after signature score predictions had been calculated.

MS and CIS B cell antibody database generation. At UTSWMC, antibody repertoires were generated from CD19+ CSF B cells using single cell PCR as previously described (Harp et al., 2007; Monson et al., 2005). The MSCSF database consists of antibody rearrangements from 373 CD19+ CSF B cells from 10 RRMS and 1 PPMS patient recruited at UTSWMC. The CISCSF database consists of antibody rearrangements from 304 CD19+ CSF B cells from 10 CIS patients (ON4-8 did not have a CD19+ CSF B cell antibody repertoire) and 228 CD138+ CSF plasma cells from 7 CIS patients (CIS132, CIS429, ON4-10 and ON3-4 did not have CD138+ CSF plasma cell antibody repertoires). To clarify, antibody repertoires from CIS patients at UCD were generated from both single CD19+ CSF B cells and single CD138+ CSF plasma cells (Bennett et al., 2008), while antibody repertoires from CIS patients at UTSWMC were generated from single CD19+ CSF B cells only. Since the resultant databases (CIS CD19+ CSF from UTSWMC, CIS CD19+ and CIS CD138+ CSF from UCD) were similar in mutational frequency, variable heavy chain (VH) gene family usage, and heavy chain Joining segment (JH) usage, the two databases were combined for analysis (Table 19).

Control B cell antibody database generation. The healthy control peripheral blood (HCPB) antibody database has been used in multiple studies (Brezinschek et al., 1997; 1998; Dorner et al., 1997, 1998a,b,c; Farner et al., 1999; Hansen et al., 2000; Harp et al., 2007; Monson et al., 2000; 2005) and consists of 348 CD19+ or CD19+/IgM+ peripheral B cells from two healthy control donors. The memory HCPB antibody database (mHCPB) consists of 205 sequences from the HCPB antibody database that contain 4 or more mutations (less than 98% homology to the germline sequence, n=123) combined with sequences from a HCPB antibody database generated from class-switched IgD-CD27+ memory B cells (n=82) (Tian et al., 2007) (Genbank 535266-535274, 535324-535368, 535381-535408, and 535416-535418). As expected, the class-switched IgD-CD27+ memory B cell database had a higher percentage of mutated codons that resulted in a replacement than the mHCPB database (compare 64.7% vs 70.3%, p=0.002 by $\chi 2$ test). The OND CD19+ CSF antibody database consists of 65 sequences. UCD and UTSWMC cell isolation and IgH amplification was performed similarly. All sequences were reconfirmed by the inventors' laboratory using IgBlast (those obtained from UCD and from GenBank) (world-wide-web at ncbi.nlm.nih.gov/igblast/), and only codons 24-93 were considered in the analysis.

Mutation analyses. Frequency of replacement mutations (RF) was calculated as the number of replacement mutations at each codon position divided by the total number of replacement mutations in each VH4 sub-database and displayed as a percentage. The MSCSF database contains 373 sequences with 475 replacement mutations, and the CISCSF database contains 302 CD19+ and 226 CD138+ sequences with 4081 replacement mutations (2052 in CD19+ and 2029 in CD138+). The HCPB database contains 348 sequences with 1086 replacement mutations, and the mHCPB database contains 205 sequences with 1857 replacement mutations. The ONDCSF database contains 65 sequences with 482 replacement mutations, and the MSPB database contains 156 sequences with 392 replacement mutations. In total, 1675 sequences and 10,373 replacement mutations were analyzed in this manner. Table 20 contains VH4 sequence numbers and Table 21 legend contains number of VH4 replacement mutations. Codon domains and numbers were defined by Kabat (Kabat et al., 1983), and Tomlinson in V-base (vbase.mrc-cpe.cam.ac.uk/), respectively.

Statistical strategy for signature identification. Codons included in the signature were identified using three criteria. First, the inventors identified codons that had statistically different RF values in the MSCSFVH4 database compared to HCPBVH4 by Goodness of Fit test where the expected frequency is the RF calculated in HCPBVH4. Twenty-four codons passed this criterion. Next, codon positions that had an RF in both the MSCSFVH4 and HCPBVH4 databases that was less than the average +2 S.D. of the memory HCPBVH4 subdatabase were excluded. Thus, since the average±S.D. RF of the memory HCPBVH4 database was 0.68±0.59, any individual codon RF less than 1.86 in both databases was excluded. Fourteen codons passed this additional criterion. Eight of these 14 codons (31B, 32, 40, 56, 57, 60, 81, and 89) were defined as "hot" since the RF at that codon position within the MSCSFVH4 database was statistically higher compared to the HCPBVH4 database. Six of these 14 codons (30, 43, 52, 77, 82 and 82a) were defined as "cold" since the RF at that codon position within the MSCSFVH4 database was statistically less compared to the HCPBVH4 database. Two of the 6 "cold" codons (52 and 82a) were excluded because the RF value in the MSCSFVH4 database at that codon position was significantly higher than 1.86 (the average +2 S.D. of the memory HCPBVH4 subdatabase). The overall signature consequently consisted of codons 30, 31B, 32, 40, 43, 56, 57, 60, 77, 81, 82, and 89. This analysis was not biased by differences in the prevalence of particular codons (31B in particular), as individual VH4 gene frequencies in MSCSF were similar to HCPB by $\chi 194\ 2$ test using a Bonferroni corrected p-value of 0.004 (data not shown).

Statistical computation of the signature score. Signature scores were generated by calculating Z-scores for the RF values at the 6 codons within the signature (31B, 40, 56, 57, 81 and 89) that had the most significant difference in RF compared to HCPBVH4 at each codon position. The Z-score formula is: (RF at codon X minus the average RF in HCPBVH4)/(standard deviation of the average RF in HCPBVH4). For example, the average RF in HCPBVH4 within the 6 signature codons was 1.6±0.9 and so an RF of 4.4 at codon 31B would be assigned a score of 3.1 (Z-score=(4.4−1.6)/0.9). Individual Z-scores at each of the 6 codon positions were then added to generate the composite signature Z-score. The average composite signature score in the MSCSFVH4 database was 10.9±2.0 and so any signature score of an individual CIS patient above 6.8 (average−2 S.D.) was predicted to convert to CDMS. Of note, both the ONDCSFVH4 signature score (at 4.5), and the MSPBVH4 score (at 2.0) were below the threshold for MS conversion. CD19+ CSF B cell and CD138+ CSF plasma cell mutation positions both contributed to each CIS patient's signature score, while the MSCSFVH4 signature scores were only composed of CD19 214+ CSF B cells.

VH4 structure. A human VH4-30.4 antibody structure described in (Guddat et al., 1993) was obtained from the Protein Data Bank (world-wide-web rcsb.org) under the identification moniker 1MCO, and adapted using the RasMol program (mc2.cchem.berkely.edu/Rasmol/) to highlight codons within the designated signature of the heavy chain variable region.

Example 4

Results

The 51 antibody heavy chain variable genes are subdivided into 7 different families (Cook and Tomlinson, 1995; world-wide-web at ncbi.nlm.nih.gov/igblast/), and it has been well-established that peripheral blood B cells from healthy donors utilize VH antibody genes most often from the VH3 family ("HCPB" in Table 20 and (Brezinschek et al., 1995; Brezinschek et al., 1997; Huang et al., 1992; Kraj et al., 1997; Wardemann et al., 2003; Yurasov et al., 2005)). In contrast, it has been reported by us and others that B cells in the CSF of MS patients often utilize VH4 antibody genes more frequently than those in the VH3 family ("MSCSF" in Table 20 and (Baranzini et al., 1999; Colombo et al., 2000; Harp et al., 2007; Monson et al., 2005; Owens et al., 1998; 2003; 2007; Qin et al., 1998; Ritchie et al., 2004)). The CISCSF antibody database consisting of CD19+ B cells only had a similar frequency of B cells that utilize VH4 family genes in comparison to HCPB (26.2% vs. 21.8%, p=0.20 by χ2 test) (Table 20); in contrast, when CD138+ plasma cells were included, the CISCSF had a higher frequency of B cells that utilize VH4 family genes in comparison to HCPB (35.0% vs. 21.8%, p=0.00001 by χ2 test) (Table 20). Some individual CIS patient CSF B cell antibody repertoires were enriched for B cells utilizing VH4 family genes in comparison to the random expected frequency, as reported previously (Bennett et al., 2008). CSF-derived B cell antibody repertoires from patients with Other Neurological Diseases (OND) were not enriched for VH4-expressing CSF B cells in comparison to HCPB (23.1% vs. 21.8%, p=0.83 by χ2 test) or mHCPB (23.1% vs. 16.6%, p=0.24 by χ2 test), indicating that VH4 over-expression in the CSF of MS patients was not due to bias in the ability of VH4 expressing B cells to enter the CNS.

Identification of codons within MSCSF that are enriched for replacement mutations. Since VH4 expressing B cells are enriched in the CSF of MS patients, we hypothesized that mutational analysis would reveal a pattern (i.e., "signature") of antibody gene replacement mutations that is unique to VH4 expressing B cells from the CNS of MS patients in comparison to HCPB. In order to test this hypothesis, the percentage of replacement mutations (RF) at each codon within the VH4 subdatabase extracted from the parent database (MSCSFVH4) was determined and compared to the RF at each codon position within the VH4 subdatabase extracted from the parent HCPB database (HCPBVH4). Replacement frequencies were used so that only those mutations resulting in an amino acid change would be considered. In addition, codon amino acid replacement can result from 1, 2, or 3 nucleotide changes within the codon, and so replacement frequencies limit bias based on the number of nucleotides in a codon that are mutated to generate a replacement. Hot spots were defined as those codon positions within MSCSFVH4 with a statistically higher RF at a particular codon position in comparison to HCPBVH4 (Table 21). Using this approach, 8 codon positions (31B, 32, 40, 56, 57, 60, 81, and 89) were identified that have a total RF value in MSCSFVH4 (25.0%) that was statistically higher than in HCPBVH4 (12.6%) (p=0.001 by χ2 test). Cold spots were defined as those codon positions within MSCSFVH4 with a statistically lower RF at a particular codon position in comparison to HCPBVH4 (Table 21). Four codons (30, 43, 77 and 82) were identified as cold spots that have a total RF value in MSCSFVH4 (5.1%) that was statistically less than in HCPBVH4 (8.5%) (p=0.001 by χ2 test).

Individual MS patient RFs within the 8 hot spot codons of the signature ranged from 22.5 to 34.1% (data not shown), indicating that some individual patient MSCSF repertoires had a greater enrichment of replacements at these 8 codon positions than others. Also, the variability of RF values within the 8 hot spot codons of the signature in individual VH4 genes in MSCSFVH4 ranged from 14.5 to 36% data not shown), indicating that some individual VH4 genes had a greater enrichment of replacements at these 8 hot spot codon positions than others. Previous analysis had identified codon 56 as a replacement mutation hotspot in HCPB (Dorner et al., 1997; Dorner et al., 1998a), which intensified as a hot spot in MSCSF$_{VH4}$ since a significantly greater percentage of replacement mutations were found in MSCSF$_{VH4}$ at codon 56 compared to HCPB$_{VH4}$. Of note, there was a 7.0-fold increase in replacement accumulation at codon 31B in the MSCSF$_{VH4}$ database in comparison to HCPB$_{VH4}$ that is likely due to the use of this codon by only a subset of VH4 genes (4-30, 4-31, 4-39 and 4-61).

When the analysis was restricted to those B cells expressing VH4 genes that contain codon 31B, there was a 3.1-fold increase in RF of the MSCSF$_{VH4}$ database compared to HCPB$_{VH4}$ (pb 0.001). An example of a signature-enriched VH4 antibody gene rearrangement from a CSF-derived B cell of an MS patient is provided in FIG. 8. Of note, 5 of the 8 hot spot codons of the signature retained higher RF values in MSCSF compared to the memory HCPB database (31B, 40, 56, 57, and 60), emphasizing that the signature does not simply reflect enrichment of memory B cells in the CSF.

Potency of signature score to predict development of clinically definite MS. The inventors reasoned that prevalence of the signature would allow them to identify patients at risk to develop MS who subsequently convert to CDMS. Current criteria for diagnosis of MS requires dissemination of lesions both in time and space (Barkhof et al., 1997; Polman et al., 2005; Tintore et al., 2000). When MRI lesions alone are not sufficient to confirm diagnosis, CSF abnormalities can be used to meet the criteria of dissemination in space (Polman et al., 2005; Siritho and Freedman, 2009). Risk of conversion to clinically definite MS in patients who have had a single demyelinating event is 50-90% if the patient has an abnormal MRI (Beck et al., 2003; Brex et al., 2002; Cole et al., 1998; O'Riordan et al., 1998; Soderstrom et al., 1998), but of those patients with a normal MRI, up to 29% had oligoclonal bands and converted to CDMS (Cole et al., 1998).

Figure 9:
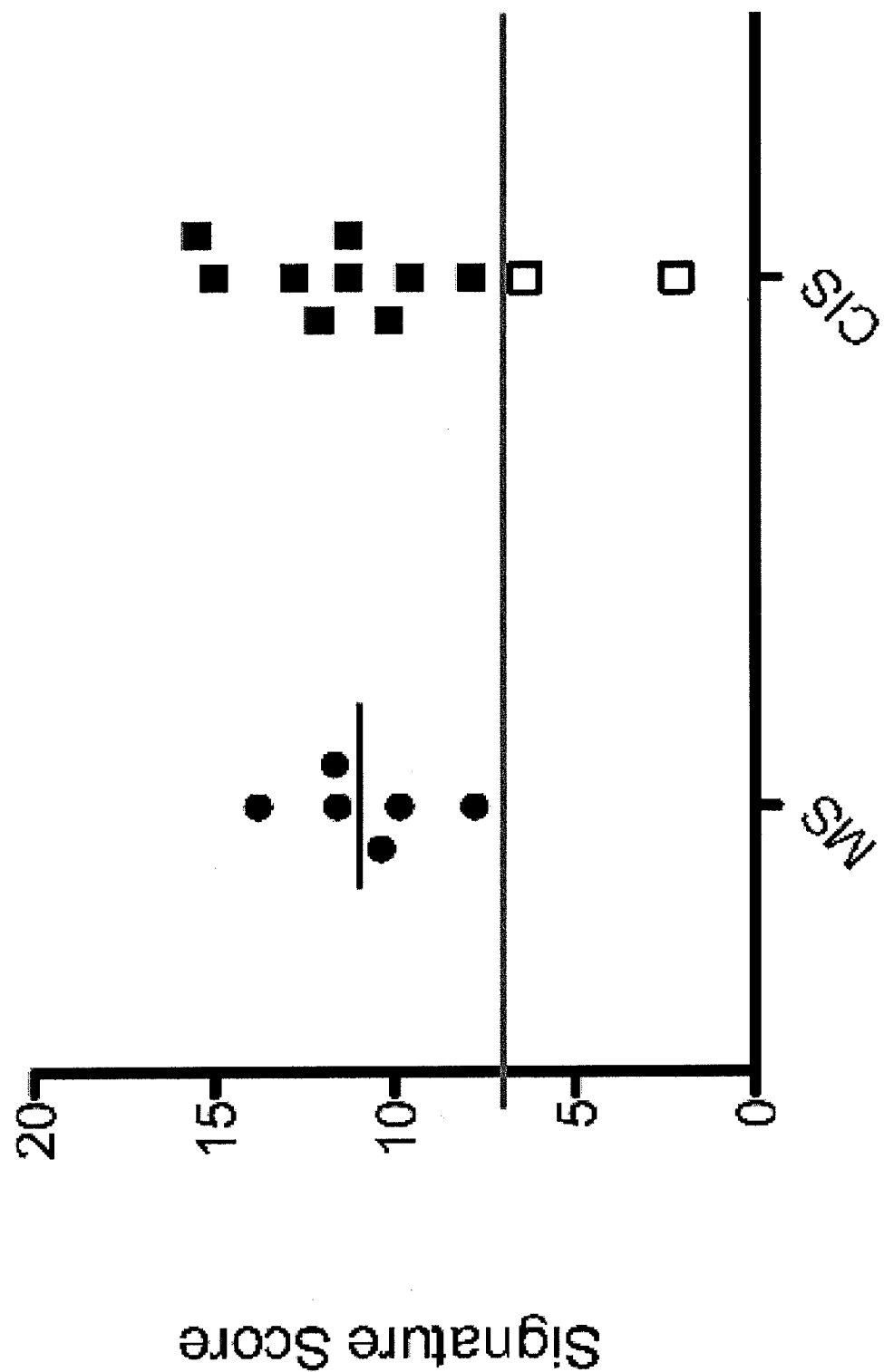
FIG. 9. Signature score in individual MS and CIS patients. Signature scores were generated by calculating Z-scores for the RF values at the 6 codons within the signature (31B, 40, 56, 57, 81 and 89). Individual Z-scores at each of the codon positions were compiled to generate the composite signature Z-score. MS patient signature scores are shown as black circles (●), CIS patient signature scores that resulted in prediction of CDMS are black squares (■), and CIS patient signature scores that resulted in prediction of unlikely to convert to definite MS are in open squares (□). The average composite signature score in the MSCSFVH4 database was 10.9±2.0 (black line) and so any signature score of an individual CIS patient above 6.8 (average S.D.; threshold shown as red line) was predicted to convert to CDMS. For reference, ONDCSFVH4 group signature score was 4.5, and MSPBVH4 signature score was 2.0.

In order to test whether signature prevalence could predict conversion to MS, the inventors generated CSF B cell repertoires from patients who had one demyelinating event that placed them "at risk" to develop MS. Such patients are typically diagnosed with CIS. CD19+ B-cell and CD138 plasma cell repertoires from the CSF of two CIS patients at UTSWMC and nine patients at UCHSC were generated and analyzed for RF values within the 6 codons of the signature defined in the MSCSF$_{VH4}$ database that had the most significant difference in RF compared to HCPB$_{VH4}$ at each codon position (codons 31B, 40, 56, 57, 81 and 89). RF values were combined using a signature score that accounts for RF variance as described in Materials and methods. The average signature score in the MSCSF$_{VH4}$ database was 10.9±2.0 (range 7.6-11.9), and so any individual CIS patient score that was 6.8 (average signature score−2 S.D.) or higher was predicted to develop MS (FIG. 9 and Table 22). Notably, the signature score from a pool of VH4 expressing CSF B cells of 3 OND patients was 4.5, and the signature score from a pool of VH4 expressing peripheral blood B cells of 3 CDMS patients was 2.0, and thus did not reach the 6.8 signature score threshold. Also, signature scores based on CD19+ B cell sequences only (in the patients where this was possible) did not change predictions based on signature score. This was expected since there is significant overlap in the antibody gene repertoires of CD19+ B cells and CD138+ plasma cells from the CSF of the same patients (Martin Mdel and Monson, 2007; Ritchie et al., 2004), suggesting that the memory B cell pool present in the CSF is the reservoir for differentiation of plasma cells in the CSF.

As indicated in Table 22, prediction of conversion to CDMS using the antibody gene signature score was accurate in 8 of 8 CIS patients that converted to CDMS. Lack of signature prevalence also accurately predicted that 2 of 2 patients who had recently experienced a first demyelinating event (ON3-1 and ON4-10) would not develop CDMS, and indeed, have not developed CDMS up to 2 years after initial sampling. One additional patient who had recently experienced a first demyelinating event (ON3-4) had a high signature score (11.3), but had not converted to CDMS at the 2-year follow-up. The antibody gene signature yielded a sensitivity of 100%, specificity of 67%, positive predictive value of 89%, negative predictive value of 100%, and accuracy of 91%, as defined by others applying the McDonald Criteria to identify CIS patients that would convert to MS (Dalton et al., 2002). Most patients in this cohort converted to CDMS within 3-6 months of repertoire sampling, although in the case of CIS132, conversion to CDMS was not confirmed until 17 months after antibody repertoire sampling (Table 22). MRI, OCB and VH4/VH2 bias are also useful in assessing probability of MS conversion (Bennett et al., 2008; Freedman et al., 2005; Frohman et al., 2003; Korteweg et al., 2006; Paolino et al., 1996; Soderstrom et al., 1998), but were not considered in calculating the signature score.

Example 5

Discussion

The intense somatic hypermutation accumulation in MSCSF$_{VH4}$ enabled us to identify a unique antibody gene signature-enriched for replacement accumulation at codons 31B, 32, 40, 56, 57, 60, 81 and 89 that was not observed in HCPB$_{VH4}$ or ONDCSF$_{VH4}$. Of note, any residual effect of naïve B cells on the RF calculation was minimized by tabulating only those sequences with mutations resulting in amino acid replacements. This approach minimized bias in the signature that may have reflected enrichment of mutation accumulation in CNS derived B cells (which are mostly memory and thus have high mutation rates) compared to peripheral B cells (which are mostly naïve and thus have low mutation rates). In addition, 5 of the 8 hot codons of the signature retain higher RF values in the MSCSF database compared to the memory HCPB database. Finally, if signature score reflected enrichment of mutation accumulation due to the repertoire's high memory representation, then all signature scores from the CISCSF antibody repertoires should have been high since they were all heavily enriched for memory B cells. This was not the case, since CISCSF repertoires ON3-1 and ON4-10, despite being heavily enriched for memory B cells (with mutation frequencies of 5.2% and 6.7%, respectively), had signature scores below the threshold of 6.8 (ON3-1 score=6.4, ON4-10 score=2.2).

It was compelling to investigate whether the antibody gene signature may be of value to identify CIS patients who would subsequently develop MS, since early and accurate diagnosis of MS is of tantamount importance in clinical care (Stuve et al., 2008). Signature prevalence could be used to identify patients who would be diagnosed with CDMS within 3-18 months of experiencing their first demyelinating event. Of note, patient ON3-4 had a signature score that indicated this patient would convert to CDMS (score=11.3), but did not demonstrate a lesion load by MRI, banding by OCB, or VH4/VH2 bias, and had not developed CDMS up to 2 years after sampling was performed (Table 22). It will be interesting to determine whether this patient is diagnosed with CDMS over time. It is also important to note that the majority of patients in this cohort already had evidence of MS risk as indicated by positive MRI and OCB. Patient ON4-7, however, did not present with brain lesions by MRI, but had a signature score that indicated this patient would be diagnosed with CDMS (score=10.2). Indeed, this patient did convert to CDMS within 5 months of CSF B cell antibody repertoire sampling, and provides a reasonable example of how signature prevalence may predict CDMS diagnosis in patients that either do not present with brain lesions by MRI, or who are not evaluated by MRI at this stage of their disease. It will be interesting to determine whether the combination of MRI and signature prevalence would be useful in predicting MS conversion. Signature prevalence may also provide an evaluation mechanism to identify the most appropriate patient candidates to receive B cell depletion therapies, for example. Certainly this is a priority since a recent investigation demonstrated significant efficacy of Rituxan in RRMS patients (Hauser et al., 2008).

Given the urgency for the early identification of MS and the rapid initiation of disease modifying therapy, presentation of a molecular signature in the CSF B cells of CIS patients who develop MS may provide a unique tool for identifying at risk individuals. However, wide implementation of the current form of this approach would be problematic since the AGS scores presented here were generated using a specialized technique that is labor intensive (single cell PCR) and requires fresh CSF for sampling. Developing other approaches to generate AGS data that maintains accuracy, but does not require a specialized laboratory to perform, is attainable and of paramount importance.

In addition, many early MS patients have atypical clinical presentations or unremarkable MRI scans, and patients with alternative inflammatory conditions may mimic idiopathic demyelinating disease. In these circumstances, the advent of a molecular diagnostic signature would increase diagnostic sensitivity and specificity. Investigating the utility of the antibody gene signature in such patients is ongoing in the inventors' laboratory.

Figure 10A:
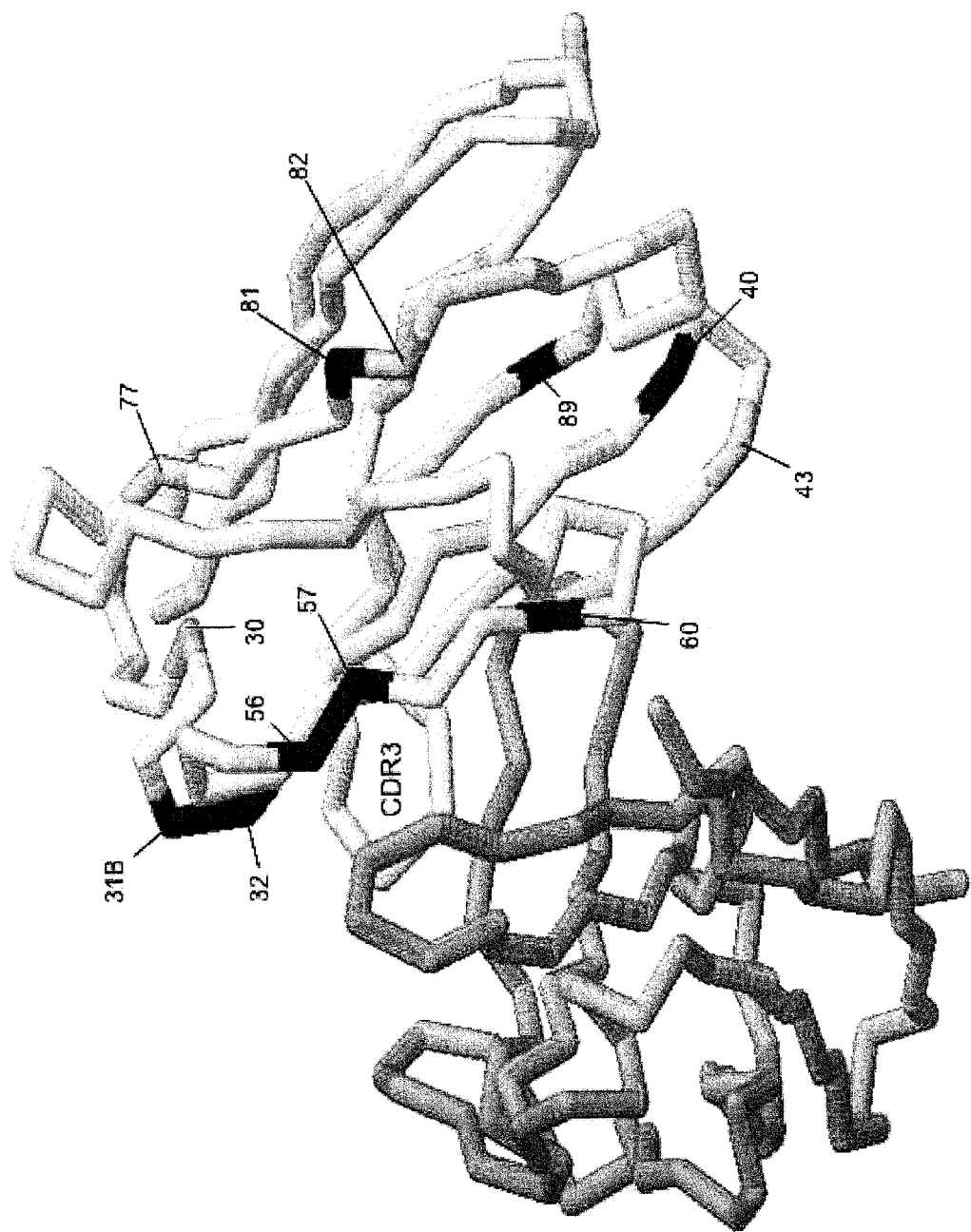
FIGS. 10A-B. Model of VH4 structure. A VH4-30.4 antibody structure was adapted as described in the Materials & Methods. Two orientations of the structure are provided in FIGS. 10A and 10B. The light chain variable domain is included for reference and is encoded in gray, while the heavy chain backbone is in yellow. The VH4 signature has been demarcated, with "hot" spots in blue (residues 31B, 32, 40, 56, 57, 60, 81, and 89), and "cold" spots in green (residues 30, 43, 77, and 82). Residues contained within CDR1 and 2 are boxed. The CDR3 is that of the original structure, and not from any VH4 rearrangement discussed here.
Figure 10B:
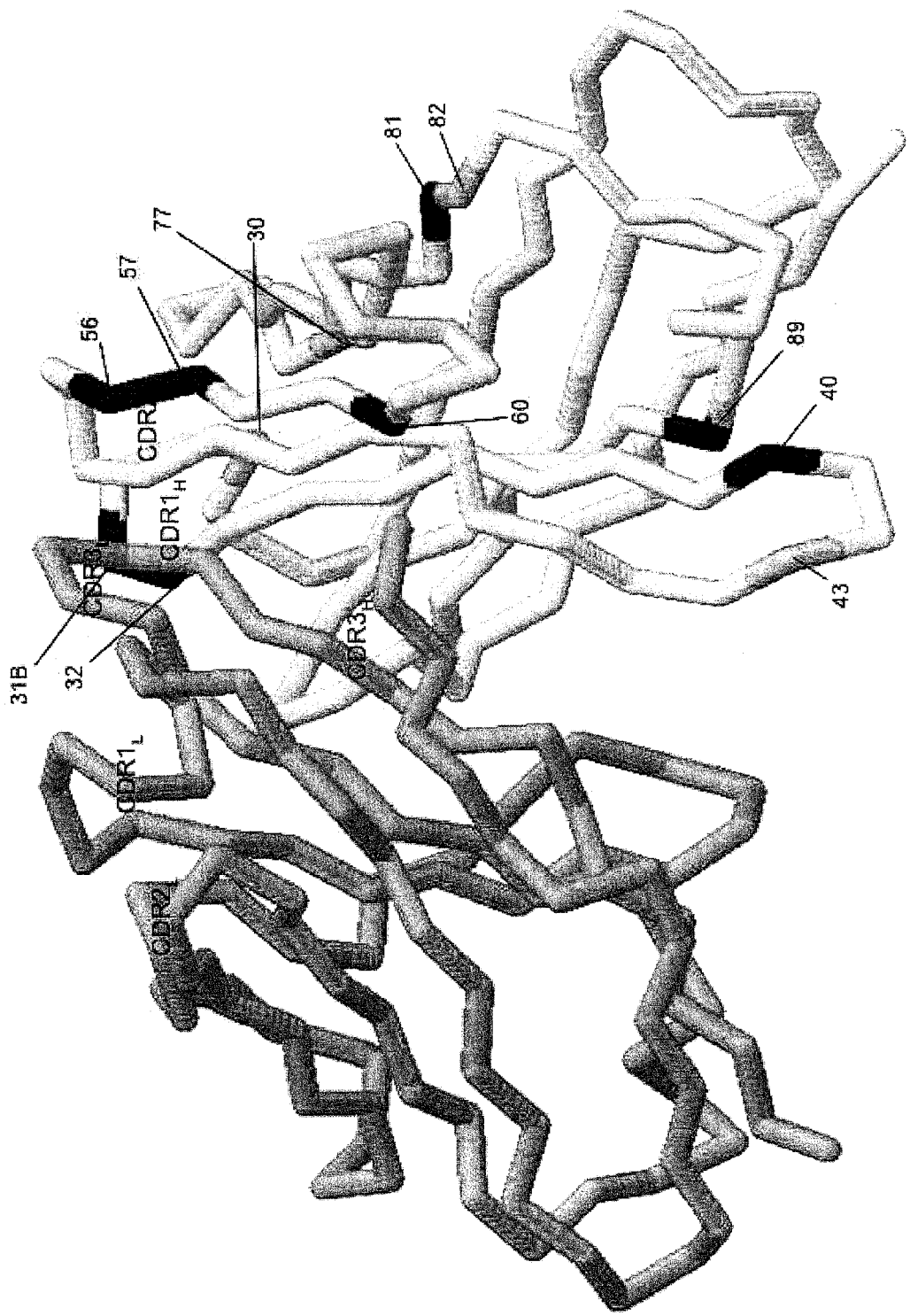

The presence of a mutational signature among clonally expanded VH4 germline antibodies in MSCSF may be helpful in understanding disease pathogenesis. For example, the VH4 germline mutational signature may be the direct result of antigen targeting in the humoral immune response. Therefore, determining the antigen specificity of signature-enriched antibodies from CSF B cells of patients with definite MS and CIS is one of the first steps towards dissecting whether signature-enriched B cells have the potential to participate in MS pathogenesis. Of note, 5 of the 8 signature codons (31B, 32, 56, 57 and 60) the inventors identified as having a unique accumulation of amino acid replacements in MSCSF$_{VH4}$ are predicted to have direct antigen contact since they reside in CDRs (FIGS. 10A-B). Dissecting the relative contribution of replacement mutations at each of these signature codons as well as those outside of the antigen binding region will address the impact of both codon classifications (direct and indirect antigen binding capacity) on antigen binding affinity.

In summary, a unique signature of antibody gene replacement mutations was identified in the MSCSF$_{VH4}$ database that is not observed in healthy control peripheral blood or CSF-derived VH4-expressing B cells from patients with other neurological diseases. Prevalence of the signature was accurate in identifying CIS patients that would convert to CDMS, but needs to be tested on a larger cohort of patients at both high and low risk to develop MS. Identifying the antigen specificity of signature-enriched CSF B cells from these patients may also reveal a unique group of antigens that are central to initiation of humoral autoimmunity in the CNS. It is likely that the MS-specific VH4 antibody gene signature provides both a new focus of investigation to further elucidate the role of B cells and their antibody products in MS and a new candidate molecular diagnostic tool for MS.

TABLE 19

CISCSF B Cell Repertoire Source Comparison

| Cell Source | CISCSF CD19+ | CISCSF CD19+ + CD138 | p value |
|---|---|---|---|
| VH1 | 9.9 | 8.9 | NS |
| VH2 | 5.3 | 7.0 | NS |
| VH3 | 56.0 | 47.5 | 0.02 |
| VH4 | 26.5 | 35.0 | 0.01 |
| JH1 | 2.7 | 2.5 | NS |
| JH2 | 3.7 | 2.6 | NS |
| JH3 | 11.6 | 11.2 | NS |
| JH4 | 44.9 | 42.9 | NS |
| JH5 | 15.0 | 14.0 | NS |
| JH6 | 22.3 | 26.8 | NS |
| % of mutated codons resulting in a replacement[a] | 68.4 | 68.4 | NS |
| MF[b] | 5.3 | 5.7 | <0.001 |

Abbreviations used in this table:
CIS = clinically isolated syndrome;
CSF = cerebrospinal fluid;
RF = replacement frequence;
MF = mutational frequence;
NS = not significant
[a]Number of mutated codons causing replacement divided by the number total mutated codons (replacement and silent)
[b]Number of mutations divided by read length (codons 31 through 93 for both calculations)

TABLE 20

Frequences of VH Family Usage[a]

| B Cell Source | Expected Frequence By Gene Frequency[j] | HCPB[b] CD19+ | mHCPB[c] CD 19+ IgD−CD27+ | MSCSF[d] CD19+ | CISCSF[e] CD19+ | CISCSF[f] CD19+ CD138+ | ONDCSF[g] CD19+ |
|---|---|---|---|---|---|---|---|
| VH1 | 21.6 | 15.5 | 10.7 | 27.1[h,i] | 9.9 | 8.9 | 20.0 |
| VH2 | 5.9 | 2.0 | 2.0 | 1.6 | 5.3[h] | 7.0 | 3.1 |
| VH3 | 43.1 | 55.2 | 62.0 | 32.4[h,i] | 56.3 | 47.5 | 46.2[i] |
| VH4 | 21.6 | 21.8 | 16.6 | 34.3[h,i] | 26.2[i] | 35.0 | 23.1 |
| Total Sequences | 51 | 348 | 205 | 373 | 302 | 528 | 65 |
| Number of Donors | 0 | 2 | 6 | 11 | 10 | 11 | 3 |

Abbreviations:
VH, variable heavy;
HCPB, healthy control peripheral blood;
mHCPB, memory healthy control peripheral blood;
MSCSF, multiple sclerosis cerebrospinal fluid;
CISCSF, clinically isolated syndrome cerebrospinal fluid;
ONDCSF, other neurological disease cerebrospinal fluid.
[a]Values provided in percent.
[b]The HCPB group includes CD19+ B cell antibody sequences from healthy controls BF1 (n = 67) and BF2 (n = 281).
[c]The mHCPB group includes CD19+ B cell antibody sequences from healthy controls BF1 (n = 18) and BF2 (n = 105) with 4 or more mutations (less than 98% homology to germline) and IgD−CD27+ B cell antibody sequences from healthy controls HA (n = 9), HB (n = 44), HC (n = 26), and HE (n = 3) (Tian et al., 2007)
[d]The MSCSF group includes CD19+ sequences from MS patients M125 (n = 101), M199 (n = 19), M354 (n = 6), M368 (n = 49), M376 (n = 8), M484 (n = 9), M522 (n = 71), M584 (n = 85), M875 (n = 21), M217 (n = 1), and M887 (n = 3).
[e]The CISCSF group includes CD19+ sequences from CIS patients CIS132 (n = 19), CIS429 (n = 57), CIS3-1 (n = 24), ON3-1 (n = 23), ON3-3 (n = 39), ON3-4 (n = 28), ON3-5 (n = 35), ON4-7 (n = 17), ON4-10 (n = 31), and ON5-2 (n = 29).
[f]In addition to those CD19+ sequences, this group includes CD138+ sequences from CIS patients CIS3-1 (n = 76), ON3-1 (n = 45), ON3-3 (n = 12), ON3-5 (n = 44), ON4-7 (n = 20), ON4-8 (n = 17), ON5-2 (n = 12).
[g]The ONDCSF group includes CD19+ B cell antibody sequences from OND patients OND341 (n = 32), OND758 (n = 19), and OND116 (n = 14).
[h]Significantly different from HCPB frequency
[i]Significantly different from mHCPB frequency
[j]Expected frequency from (Cook and Tomlinson, 1995)

TABLE 21

Percentage of Replacement Mutations in Each Signature Codon

| Codon | Location[b] | MSCSF$_{VH4}$ RF | HCPB$_{VH4}$ RF | HCPB$_{VH4}$ Fold Increase | HCPB$_{VH4}$ p-value[d] | mHCPB$_{VH4}$ RF | mHCPB$_{VH4}$ Fold Increase | mHCPB$_{VH4}$ p-value[d] |
|---|---|---|---|---|---|---|---|---|
| 31B[c] | CDR1 | 3.5[5] | 0.5[5] | 7.0 | 0.001 | 0.8 | 4.4 | 0.001 |
| 32 | CDR1 | 2.3 | 1.5 | 1.5 | 0.05 | 2.1 | 1.1 | NS |
| 40[c] | FR2 | 2.7 | 1.0 | 2.7 | 0.001 | 1.1 | 2.5 | 0.001 |
| 56[a,c] | CDR2 | 5.5 | 3.0 | 1.8 | 0.001 | 3.2 | 1.7 | 0.001 |
| 57[c] | CDR2 | 2.0 | 1.0 | 2.0 | 0.005 | 0.5 | 3.7 | 0.001 |
| 60 | CDR2 | 2.4 | 1.5 | 1.6 | 0.05 | 1.1 | 2.2 | 0.001 |
| 81[c] | FR3 | 4.7 | 3.0 | 1.5 | 0.005 | 3.7 | 1.3 | NS |
| 89[c] | FR3 | 2.0 | 1.0 | 2.0 | 0.005 | 1.3 | 1.5 | NS |
| Hotspot Total[e] | | 25.0 | 12.6 | 2.0 | 0.001 | 13.8 | 1.8 | 0.001 |
| 30 | FR1 | 2.0 | 4.0 | 0.5 | 0.005 | 2.9 | 0.7 | NS |
| 43 | FR2 | 0.9 | 2.0 | 0.5 | 0.025 | 1.3 | 0.7 | NS |
| 77 | FR3 | 1.5 | 2.5 | 0.6 | 0.05 | 1.6 | 0.9 | NS |
| 82 | FR3 | 0.7 | 2.5 | 0.3 | 0.001 | 1.6 | 0.5 | 0.05 |
| Coldspot Total[e] | | 5.1 | 8.5 | 0.5 | 0.001 | 7.4 | 0.7 | 0.01 |

Abbreviations in table:
CDR, complementary determining region;
FR, framework;
RF, replacement frequency;
MSCSF, multiple sclerosis cerebrospinal fluid;
HCPB, healthy control peripheral blood;
mHCPB, memory HCPB;
NS, not significant
[a]Previously published replacement hotspot (Dorner et al., 1997; Dorner et al., 1998a)
[b]As defined by Kabat (Kabat et al., 1983)
[c]"Hotspot Total" is the total RF within codons 31B, 32, 40, 56, 57, 60, 81 and 89. "Coldspot Total" is the total RF within codons 30, 43, 77, and 82. 199, 337 and 965 replacements respectively were included in this analysis for HCPB$_{VH4}$, mHCPBVH4, and MSCSF$_{VH4}$.
[d]Comparing HCPB$_{VH4}$ or mHCPB$_{VH4}$ to MSCSF$_{VH4}$ RFs at each codon position using $\chi^2$ goodness-of-fit where expected frequence is the RF calculated in HCPB$_{VH4}$ respectively.
[e]Codon used in the calculation of signature score

TABLE 22

CIS Patient Summary and Signature Score Predictions

| Subject No.[a] | Time to LP[b] | MRI Brain Lesions | OCB | CD19/CD138[c] | CD19 VH4 bias[d] | CD138 VH4 bias[d] | Signature Score[e] | Prediction Based On Signature Score | Definite MS | Time to MS Diagnosis[f] |
|---|---|---|---|---|---|---|---|---|---|---|
| CIS132 | 1 | GD+ | Yes | 19/NA | No | NA | 12.1 | CDMS | Clinical | 18 |
| CIS429 | 1 | GD+ | Yes | 56/NA | No | NA | 15.0 | CDMS | Clinical | 3 |
| CIS3-1 | 2 | WML | Yes | 24/76 | Yes | Yes | 15.5 | CDMS | MRI | 3 |
| ON3-3 | 4 | GD+ | Yes | 39/13 | No | No | 11.3 | CDMS | Clinical | 3 |
| ON3-5 | 1.75 | GD+ | Yes | 35/44 | Yes | Yes | 12.8 | CDMS | Clinical | 2 |
| ON4-7 | 3 | None[g] | Yes | 17/20 | No | Yes | 10.2 | CDMS | Clinical | 5 |
| ON4-8 | 1.5 | WML | Yes | NA/18 | NA | Yes | 9.6 | CDMS | Clinical | 5 |
| ON5-2 | 1 | GD+ | Yes | 29/12 | Yes | Yes | 7.9 | CDMS | Clinical | 3 |
| ON3-1 | 10 | WML | Yes | 23/45 | No | No | 6.4 | No | — | NA |
| ON4-10 | 1.25 | WML | No | 31/NA | No | NA | 2.2 | No | — | NA |
| ON3-4 | 1.5 | None[g] | No | 28/NA | No | NA | 11.3 | CDMS | — | NA |

Abbreviations in table:
CIS, Clinically Isolated Syndrome;
ON, Optic Neuritis;
LP, lumbar puncture,
GD, gadolinium enhancing lesion positive;
WML, white matter lesions by T2,
OCB, oligoclonal bands;
CDMS, clinically definite
MS; NA, not applicable
[a]CIS132 and CIS429 were generated at UTSWMC; the remaining patient CSF B cell repertoires were generated at UCD.
[b]monhts from first demyelinating event to LP
[c]Values given are number of unique sequeces in CD19 repertoire/CD138 repertoire; family usage can be found in (Bennett et al., 2008; Harp et al., 2007); CIS429 was a 62 y.o. male first presenting with optic neuritis and the repertoire had 2% VH1 usage, 0% VH2, 77% VH3 and 19% VH4.
[d]Bias was considered significantly different from random frequence (Cook and Tomlinson, 1995) or expected frequence in HCPB (Brezinschek et al., 1997; Brezinschek et al., 1998; Dorner et al., 1997; Dorner etr al., 1998a; Dorner et al., 1998b; Dorner et al., 1998c; Farner et al., 1999; Hansen et al., 2000; Monson et al., 2000). VH2 bias was also observed in CD19 repertoires from ON4-7, and CD138 repertoires from ON3-3, ON3-5 and ON4-7.
[e]Signature score was calculated as outlined in materials and methods, and uses both CD19 and CD138 sequences. The average score among MS patients is 10.9 ± 2.0.
[f]Months from first demyelinating event to MS diagnosis.
[g]One spinal cord lesion was observed by T2 weighted MRI.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

V. References

The following references, to the extent that they provide exemplary procedural or other details supplementary to those set forth herein, are specifically incorporated herein by reference:

U.S. Pat. No. 4,582,788
U.S. Pat. No. 4,656,127
U.S. Pat. No. 4,659,774
U.S. Pat. No. 4,682,195
U.S. Pat. No. 4,683,194
U.S. Pat. No. 4,683,195
U.S. Pat. No. 4,683,202
U.S. Pat. No. 4,800,159
U.S. Pat. No. 4,816,571
U.S. Pat. No. 4,883,750
U.S. Pat. No. 4,946,773
U.S. Pat. No. 4,959,463
U.S. Pat. No. 4,965,188
U.S. Pat. No. 5,130,238
U.S. Pat. No. 5,141,813
U.S. Pat. No. 5,169,766
U.S. Pat. No. 5,264,566
U.S. Pat. No. 5,279,721
U.S. Pat. No. 5,428,148
U.S. Pat. No. 5,554,744
U.S. Pat. No. 5,574,146
U.S. Pat. No. 5,602,244
U.S. Pat. No. 5,605,798
U.S. Pat. No. 5,645,897
U.S. Pat. No. 5,705,629
U.S. Pat. No. 5,840,873
U.S. Pat. No. 5,843,640
U.S. Pat. No. 5,843,650
U.S. Pat. No. 5,843,651
U.S. Pat. No. 5,843,663
U.S. Pat. No. 5,846,708
U.S. Pat. No. 5,846,709
U.S. Pat. No. 5,846,717
U.S. Pat. No. 5,846,726
U.S. Pat. No. 5,846,729
U.S. Pat. No. 5,846,783
U.S. Pat. No. 5,849,481
U.S. Pat. No. 5,849,483
U.S. Pat. No. 5,849,486
U.S. Pat. No. 5,849,487
U.S. Pat. No. 5,849,497
U.S. Pat. No. 5,849,546
U.S. Pat. No. 5,849,547
U.S. Pat. No. 5,851,770
U.S. Pat. No. 5,851,772
U.S. Pat. No. 5,853,990
U.S. Pat. No. 5,853,992
U.S. Pat. No. 5,853,993
U.S. Pat. No. 5,856,092
U.S. Pat. No. 5,858,652
U.S. Pat. No. 5,861,244
U.S. Pat. No. 5,863,732
U.S. Pat. No. 5,863,753
U.S. Pat. No. 5,866,331
U.S. Pat. No. 5,866,337
U.S. Pat. No. 5,866,366
U.S. Pat. No. 5,900,481
U.S. Pat. No. 5,905,024
U.S. Pat. No. 5,910,407
U.S. Pat. No. 5,912,124
U.S. Pat. No. 5,912,145
U.S. Pat. No. 5,912,148
U.S. Pat. No. 5,916,776
U.S. Pat. No. 5,916,779
U.S. Pat. No. 5,919,626
U.S. Pat. No. 5,919,630
U.S. Pat. No. 5,922,574
U.S. Pat. No. 5,925,517
U.S. Pat. No. 5,925,525
U.S. Pat. No. 5,928,862
U.S. Pat. No. 5,928,869
U.S. Pat. No. 5,928,870
U.S. Pat. No. 5,928,905
U.S. Pat. No. 5,928,906
U.S. Pat. No. 5,929,227
U.S. Pat. No. 5,932,413
U.S. Pat. No. 5,932,451
U.S. Pat. No. 5,935,791
U.S. Pat. No. 5,935,825
U.S. Pat. No. 5,939,291
U.S. Pat. No. 5,942,391
U.S. Pat. No. 5,952,174

Ausubel et al., *Current Protocols in Molecular Biology*, John Wiley & Sons, NY, 1989.
Barkhof et al., *Brain*, 120(Pt11):2059-2069, 1997.
Barany, et al., *Proc. Natl. Acad. Sci. USA*, 88:189-193, 1991.
Baranzini et al., *J. Immunol.*, 163:5133-5144, 1999.
Beck et al., *Arch. Ophthalmol.*, 121:944-949, 2003.
Bellus, *J. Macromol. Sci. Pure Appl. Chem.*, A31(1): 1355-1376, 1994.
Bennett et al., *J. Neuroimmunol.*, 199:126-132, 2008.
Both et al., *Mol. Cell Biol.*, 10:5187-5196, 1990.
Berx et al., *N. Engl. J. Med.*, 346:158-164, 2002.
Brezinschek et al., *J. Clin. Invest.*, 99:2488-2501, 1997.
Brezinschek et al., *J. Immunol.*, 155:190-202, 1995.
Brezinschek et al., *J. Immunol.*, 160:4762-4767, 1998.
Buluwela and Rabbitts, *Eur. J. Immunol.*, 18:1843-1845, 1988.
Cepok et al., *Brain*, 124:2169-2176, 2001.
Cepok et al., *Brain*, 128:1667-1676, 2005.
Chothia and Lesk, *J. Mol. Biol.*, 196:901-917, 1987.
Chothia et al., *J. Mol. Biol.*, 227:799-817, 1992.
Cole et al., *Neurology*, 51:885-887, 1998.
Colombo et al., *J. Immunol.*, 164:2782-2789, 2000.
Cook and Tomlinson, *Immunol. Today*, 16:237-242, 1995.
Corcione et al., *Proc. Natl. Acad. Sci. USA*, 101:11064-11069, 2004.
Dalton et al., *Ann. Neurol.*, 52:47-53, 2002.
Damle et al., *Blood*, 94:1840-1847, 1999.
de Arruda et al., *Expert. Rev. Mol. Diagn.*, 2:487-496, 2002.

Domiati-Saad and Lipsky, *J. Immunol.*, 161:1257-1266, 1998.
Dorner et al., *J. Immunol.*, 158:2779-2789, 1997.
Dorner et al., *Eur. J. Immunol.*, 28:657-668, 1998a.
Dorner et al., *J. Immunol.*, 160:2831-2841, 1998b.
Dorner et al., *Eur. J. Immunol.*, 28:3384-3396, 1998c.
Dorner et al., *J. Immunol.*, 163:1027-1036, 1999.
EP 201,184
EP 237,362
EP 258,017
EP 266,032
EP 320 308
EP 329,822
EP 50,424
EP 84,796
Esiri, *Lancet.*, 2:478, 1977.
Farner et al., *J. Immunol.*, 162:2137-2145, 1999.
Foster et al., *Eur. J. Immunol.*, 29:3122-3132, 1999.
Freedman et al., *Arch. Neurol.*, 62:865-870, 2005.
French Pat. No. 2,650,840
Froehler et al., *Nucleic Acids Res.*, 14(13):5399-5407, 1986.
Frohman, In: *PCR Protocols. A Guide To Methods And Applications*, Academic Press, N.Y., 1990.
Frohman et al., *Neurology*, 61:602-611, 2003.
Genain et al., *Nat. Med.*, 5:170-175, 1999.
Great Britain Appln. 2 202 328
Guddat et al., *Proc. Natl. Acad. Sci. USA*, 90:4271-4275, 1993.
Hamblin et al., *Blood*, 94:1848-1854, 1999.
Hansen et al., *Int. Arch. Allergy Immunol.*, 123:36-45, 2000.
Hansen et al., *Scand. J. Immunol.*, 57:470-479, 2003.
Harp et al., *J. Neuroimmunol.*, 183:189-199, 2007.
Hauser et al.i, *N. Engl. J. Med.*, 358:676-688, 2008.
Hayashi et al., *Int. J. Mol. Med.*, 20:247-253, 2007.
Huang et al., *J. Clin. Invest.*, 89:1331-1343, 1992.
Huang et al., *Clin. Exp. Immunol.*, 112:516-527, 1998.
Humphries et al., In: *Molecular Diagnosis of Genetic Diseases*, Elles (Ed.), 321-340, 1996.
Humphries et al., *Nature*, 331:446-449, 1988.
Innis et al., *Proc. Natl. Acad. Sci. USA*, 85(24):9436-9440, 1988.
Jones, *Nature*, 199:280-282, 1963.
Kabat et al., *Am. J. Med. Sci.*, 219:55-64, 1950.
Kabat et al., *Am. J. Med.*, 4:653-662, 1948.
Kabat et al., In: *Sequences of Proteins of Immunological Interest*, United States Department of Health and Human Services, Washington, D.C., 1983.
Kabat et al., In: *Sequences of Proteins of Immunological Interest*, 4$^{th}$ Ed., United States Department of Health and Human Services, Washington, D.C., 1987.
Kirkham and Schroeder, *Semin. Immunol.*, 6:347-360, 1994.
Kodaira et al., *J. Mol. Biol.*, 190:529-541, 1986.
Koelsch et al., *J. Clin. Invest.*, 117(6):1558-65, 2007.
Komher, et al., *Nucl. Acids. Res.* 17:7779-7784, 1989.
Korteweg et al., *Lancet. Neurol.*, 5:221-227, 2006.
Kraj et al., *J. Immunol.*, 158:5842-5832, 1997.
Kuppuswamy et al., *Proc. Natl. Acad. Sci. USA*, 88:1143-1147, 1991.
Kwoh et al., *Proc. Natl. Acad. Sci. USA*, 86:1173, 1989.
Kwok and Chen, *Curr Issues Mol. Biol.*, 5(2):43-60, 2003.
Kwok, *Annu. Rev. Genomics Hum. Genet.*, 2:235-258, 2001.
Lambracht-Washington et al., *J. Neuroimmunol.*, 186(1-2):164-76, 2007.
Landegren et al., *Science* 241:1077-1080, 1988.
Lee et al., *J. Mol. Biol.*, 195:761-768, 1987.
Lu et al., *Biopolymers*, 73:606-613, 2004.
Magliozzi et al., *J. Neuroimmunol.*, 148:11-23, 2004.
Martin-Mdel and Monson, *Front Biosci.*, 12:2735-2749, 2007.
Maxam et al., *Proc. Natl. Acad. Sci. USA*, 74:560, 1977.
McDonald et al., *Ann. Neurol.*, 50:121-127, 2001.
Meffre et al., *Nat. Immunol.*, 1:207-213, 2000.
Meyers et al., *Science*, 230:1242, 1985.
Mockridge et al., *Autoimmunity*, 37:9-15, 2004.
Modrich, *Ann. Rev. Genet.*, 25:229-253, 1991.
Monson et al., *Eur. J. Immunol.*, 30:1597-1605, 2000.
Monson et al., *J. Neuroimmunol.*, 158:170-181, 2005.
Mullis et al., *Cold Spring Harbor Symp. Quant. Biol.* 51:263-273, 1986.
Nickerson et al., *Proc. Natl. Acad. Sci. USA*, 87:8923-8927, 1990.
Nyren et al., *Anal. Biochem.* 208:171-175, 1993.
Ohara et al., *Proc. Natl. Acad. Sci. USA*, 86:5673-5677, 1989.
Oppezzo et al., *Eur. J. Immunol.*, 34:1423-1432, 2004.
Orita et al., *Genomics*, 5:874-879, 1989.
O'Riordan et al., *Brain*, 121(Pt3):495-503, 1998
Owens et al., *Ann. Neurol.*, 43:236-243, 1998.
Owens et al., *J. Immunol.*, 171:2725-2733, 2003.
Owens et al., *J. Immunol.*, 179:6343-6351, 2007.
Ozawa et al., *Brain*, 117(Pt 6):1311-1322, 1994.
Paolino et al., *J. Neurol. Neurosurg. Psychiatry*, 60:572-575, 1996.
Pascual and Capra, *Arthritis Rheum.*, 35:11-18, 1992.
PCT Appln. PCT/US87/00880
PCT Appln. PCT/US89/01025
PCT Appln. WO 88/10315
PCT Appln. WO 89/06700
PCT Appln. WO 89/06700
PCT Appln. WO 90/01069
PCT Appln. WO 93/22456
PCT Appln. WO 95/11995
PCT Appln. WO 91/02087
PCT Appln. WO 92/15712
Polman et al., *Ann. Neurol.*, 58:840-846, 2005.
Prezant et al., *Hum. Mutat.*, 1:159-164, 1992.
Pugh-Bernard et al., *J. Clin. Invest.*, 108:1061-1070, 2001.
Qin et al., *J Clin Invest* 1998. 102: 1045-1050, 1998.
Raine et al., *Ann. Neurol.*, 46:144-160, 1999.
Reimer & Jensen-Jarolim, *Immunol Lett.* 112(1):1-5 (2007).
Ritchie et al., *J. Immunol.*, 173:649-656, 2004.
Rogozin and Diaz, *J. Immunol.*, 172: 3382-3384, 2004.
Ruano et al., *Nucl. Acids Res.*, 19:6877-6882, 1991.
Ruano et al., *Nucl. Acids Res.*, 17:8392, 1989.
Sambrook et al., In: *Molecular cloning*, Cold Spring Harbor Laboratory Press, Cold Spring Harbor, N.Y., 2001.
Sanger et al., *J. Molec. Biol.*, 94:441, 1975.
Sayle and Milner-White, *Trends Biochem. Sci.*, 20:374, 1995.
Serafini et al., *Brain Pathol.*, 14:164-174, 2004.
Sheffield et al., *Proc. Natl. Acad. Sci. USA*, 86:232-236, 1989.
Shen et al., *Proc. Natl. Acad. Sci. USA*, 84:8563-8567, 1987.
Shlomchik et al., *Nature*, 328:805-811, 1987.
Siritho and Freedman, *J. Neurol. Sci.*, 2009 (In Print)
Soderstrom et al., *Neurology*, 50:708-714, 1998.
Sokolov, *Nucl. Acids Res.* 18:3671, 1990.
Souza et al., *J. Immunol.*, 179:3153-3160, 2007.
Stevens et al., *Biotechniques*, 34:198-203, 2003.
Storch and Lassmann, *Curr. Opin. Neurol.*, 10:186-192, 1997.
Stuve et al., *Drugs*, 68:73-83, 2008.
Stuve et al., *Ann. Neurol.*, 59:743-747, 2006
Syvanen et al., *Genomics* 8:684-692, 1990.
Tanaka and Nei, *Mol. Biol. Evol.*, 6:447-459, 1989.
Tian et al., *Mol. Immunol.*, 44:2173-2183, 2007.
Tintore et al., *Am. J. Neuroradiol.*, 21:702-706, 2000.

Turki et al., *J. Clin. Invest.*, 95:1635-1641, 1995.
Uccelli et al., *Trends Immunol.*, 26:254-259, 2005.
Ugozzoll et al., *GATA* 9:107-112, 1992.
Vargas-Madrazo et al., *J. Mol. Evol.*, 1994.38:100-104, 1994.
Voswinkel et al., *Ann. NY Acad. Sci.*, 815:312-315, 1997.
Walker et al., *Proc. Natl. Acad. Sci. USA*, 89:392-396, 1992.
Wardemann et al., *Science*, 301:1374-1377, 2003.
Wartell et al., *Nucl. Acids Res.*, 18:2699-2706, 1990.
Winges et al., *J. Neuroimmunol.*, 192(1-2):226-234. 2007.
Winter et al., *Proc. Natl. Acad. Sci. USA*, 82:7575, 1985.
Yurasov et al., *J. Exp. Med.*, 201:703-711, 2005.
Zheng et al., *J. Clin. Invest.*, 113:1188-1201, 2004.

---

What is claimed is:

1. A method for selecting a human subject having or at risk of developing multiple sclerosis (MS) comprising:
providing a cerebrospinal fluid (CSF) sample or peripheral blood sample, or providing DNA or RNA isolated therefrom, from a subject presenting with clinical symptoms consistent with MS;
determining nucleotide sequences in said sample for a plurality of variable heavy (VH)4 genes at codons 31B to 89, thereby identifying mutations with respect to germ-line VH4 sequences;
determining mutational frequency at one or more of codons 31B to 89;
identifying the presence or absence of a codon signature associated with MS or risk of developing MS, wherein the codon signature comprises an elevated mutational frequency at one or more of codons 31B, 32, 40, 56, 57, 60, 81 and 89; and
selecting patients exhibiting the presence of the codon signature as having or at risk of developing MS.

2. The method of claim 1, wherein said codon signature comprises an elevated mutational frequency at codon 31B, 56 and/or 81.

3. The method of claim 2, wherein said codon signature comprises an elevated mutational frequency at codons 31B, 56 and 81.

4. The method of claim 2 or 3, wherein said codon signature further comprises an elevated mutational frequency at one or more of codons 32, 40, 57, 60 and 89.

5. The method of claim 4, wherein said codon signature comprises an elevated mutational frequency at each of codons 31B, 32, 40, 56, 57, 60, 81 and 89.

6. The method of claim 1, wherein said codon signature comprises an elevated mutational frequency at codons 31B, 40, 56, 57, 81 and/or 89.

7. The method of claim 6, wherein said codon signature comprises an elevated mutational frequency at each of codons 31B, 40, 56, 57, 81 and 89.

8. The method claim 1, wherein determining nucleic acid sequences comprises a sequencing reaction.

9. The method of claim 1, wherein determining nucleic acid sequences comprises PCR.

10. The method of claim 1, wherein said sample is cerebrospinal fluid (CSF), or DNA or RNA isolated therefrom.

11. The method of claim 1, wherein said sample is peripheral blood, or DNA or RNA isolated therefrom.

12. The method of claim 1, further comprising treating said subject when said codon signature is identified.

13. A method for diagnosing multiple sclerosis (MS) disease in a subject presenting with Clinically Isolated Syndrome (CIS), the method comprising:
providing a cerebrospinal fluid (CSF) sample or peripheral blood sample, or providing DNA or RNA isolated therefrom, from said subject;
determining nucleotide sequences for a plurality of variable heavy (VH)4 genes at codons 31B to 89, thereby identifying mutations with respect to germ-line VH4 sequences;
determining a mutational frequency within codons 31B to 89 to thereby prepare a mutational profile, the mutational profile being predictive of conversion to MS disease.

14. The method of claim 13, wherein the sample is cerebrospinal fluid, or DNA or RNA isolated therefrom.

15. The method of claim 13, wherein the sample is a peripheral blood sample, or DNA or RNA isolated therefrom.

16. The method of claim 13, wherein the VH4 nucleotide sequences determined comprise codons 24 to 95.

17. The method of claim 13, wherein an elevated mutational frequency at one or more of codons 31B, 32, 40, 56, 57, 60, 81 and 89 is predictive of MS.

18. The method of claim 17, wherein mutational frequency at codon 31B, 56 and/or 81 is predictive of MS.

19. The method of claim 18, wherein mutational frequency at each of codons 31B, 56 and 81 is predictive of MS.

20. The method of claim 18, wherein mutational frequency at one or more of codons 32, 40, 57, 60 and 89 is predictive of MS.

21. The method of claim 20, wherein said mutational frequency at codons 31B, 40, 56, 57, 81 and 89 is predictive of MS.

22. The method of claim 18, wherein mutational frequency at each of codons 31B, 32, 40, 56, 57, 60, 81 and 89 is predictive of MS.

23. A method for diagnosing multiple sclerosis (MS) disease in a subject presenting with symptoms of Relapsing Remitting MS (RRMS), the method comprising:
providing a cerebrospinal fluid (CSF) sample or peripheral blood sample, or providing DNA or RNA isolated therefrom, from said subject;
determining nucleotide sequences for a plurality of variable heavy (VH)4 genes at codons 31B to 89, thereby identifying mutations with respect to germ-line VH4 sequences;
determining mutational frequency at codons 31B to 89 to thereby prepare a mutational profile, wherein an increased mutational frequency at one or more of codons 31B, 32, 40, 56, 57, 60, 81, and 89 is diagnostic of RRMS.

24. The method of claim 23, wherein the sample is cerebrospinal fluid (CSF), or DNA or RNA isolated therefrom.

25. The method of claim 23, wherein sample is peripheral blood.

26. A method for selecting a human subject having or at risk of developing multiple sclerosis (MS) comprising:
providing a cerebrospinal fluid (CSF) sample or peripheral blood sample, or providing DNA or RNA isolated therefrom, the subject having one or more symptoms of MS;
determining nucleotide sequences for a plurality of variable heavy (VH)4 genes at codons 31B to 89, thereby identifying mutations with respect to germ-line VH4 sequences;
determining mutational frequency at codons 31B to 89 to thereby prepare a mutational profile, wherein an increased mutational frequency at one or more of codons 31B, 32, 40, 56, 57, 60, 81 and 89 identifies a subject having or at risk of developing multiple sclerosis.

27. The method of claim 26, wherein increased mutational frequency at codons 31B, 40, 56, 57, 60, 81 and 89 is diagnostic of MS.

28. The method of claim 26, wherein sample is cerebrospinal fluid (CSF), or DNA or RNA isolated therefrom.

29. The method, of claim 26, wherein sample is peripheral blood, or DNA or RNA isolated therefrom.

* * * * *

UNITED STATES PATENT AND TRADEMARK OFFICE
CERTIFICATE OF CORRECTION

| | |
|---|---|
| PATENT NO. | : 8,394,583 B2 |
| APPLICATION NO. | : 12/509093 |
| DATED | : March 12, 2013 |
| INVENTOR(S) | : Nancy Monson |

It is certified that error appears in the above-identified patent and that said Letters Patent is hereby corrected as shown below:

In the Claims

In claim 21, column 82, line 17, delete "said".

Signed and Sealed this
Second Day of July, 2013

Teresa Stanek Rea
*Acting Director of the United States Patent and Trademark Office*

SEQUENCE LISTING

```
<160> NUMBER OF SEQ ID NOS: 20

<210> SEQ ID NO 1
<211> LENGTH: 299
<212> TYPE: DNA
<213> ORGANISM: Artificial
<220> FEATURE:
<223> OTHER INFORMATION: Synthetic primer
<220> FEATURE:
<221> NAME/KEY: CDS
<222> LOCATION: (1)..(297)

<400> SEQUENCE: 1 cag gtg cag ctg cag gag tcg ggc cca gga ctg gtg aag cct tcg gag      48
Gln Val Gln Leu Gln Glu Ser Gly Pro Gly Leu Val Lys Pro Ser Glu
1               5                  10                 15 acc ctg tcc ctc acc tgc act gtc tct ggt ggc tcc atc agc agt ggt      96
Thr Leu Ser Leu Thr Cys Thr Val Ser Gly Gly Ser Ile Ser Ser Gly
            20                  25                  30 ggt tac tac tgg agc tgg atc cgc cag ccc cca ggg aag ggg ctg gag     144
Gly Tyr Tyr Trp Ser Trp Ile Arg Gln Pro Pro Gly Lys Gly Leu Glu
        35                  40                  45 tgg att ggg tay atc tat tac agt ggg agc acc wac tac aac ccg tcc     192
Trp Ile Gly Tyr Ile Tyr Tyr Ser Gly Ser Thr Xaa Tyr Asn Pro Ser
    50                  55                  60 ctc aag agt cga gtc acc ata tca gta gac acg tcc aag aac cag ttc     240
Leu Lys Ser Arg Val Thr Ile Ser Val Asp Thr Ser Lys Asn Gln Phe
65                  70                  75                  80 tcc ctg aag ctg agc tct gtg acc gcc gcg gac acg gcc gtg tat tac     288
Ser Leu Lys Leu Ser Ser Val Thr Ala Ala Asp Thr Ala Val Tyr Tyr
                85                  90                  95 tgt gcg aga ga                                                       299
Cys Ala Arg <210> SEQ ID NO 2
<211> LENGTH: 99
<212> TYPE: PRT
<213> ORGANISM: Artificial
<220> FEATURE:
<221> NAME/KEY: misc_feature
<222> LOCATION: (60)..(60)
<223> OTHER INFORMATION: The 'Xaa' at location 60 stands for Asn, or
      Tyr.
<220> FEATURE:
<223> OTHER INFORMATION: Synthetic Construct

<400> SEQUENCE: 2

Gln Val Gln Leu Gln Glu Ser Gly Pro Gly Leu Val Lys Pro Ser Glu
1               5                  10                 15

Thr Leu Ser Leu Thr Cys Thr Val Ser Gly Gly Ser Ile Ser Ser Gly
            20                  25                  30

Gly Tyr Tyr Trp Ser Trp Ile Arg Gln Pro Pro Gly Lys Gly Leu Glu
        35                  40                  45

Trp Ile Gly Tyr Ile Tyr Tyr Ser Gly Ser Thr Xaa Tyr Asn Pro Ser
    50                  55                  60
```

```
Leu Lys Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                 85                  90                  95

Cys Ala Arg

<210> SEQ ID NO 3
<211> LENGTH: 299
<212> TYPE: DNA
<213> ORGANISM: Artificial
<220> FEATURE:
<223> OTHER INFORMATION: Synthetic primer
<220> FEATURE:
<221> NAME/KEY: CDS
<222> LOCATION: (1)..(297)

<400> SEQUENCE: 3 cag ctg cag ctg cag gag tcc ggc tca gga ctg gtg aag cct tca cag      48
Gln Leu Gln Leu Gln Glu Ser Gly Ser Gly Leu Val Lys Pro Ser Gln
 1               5                  10                  15 acc ctg tcc ctc acc tgc gct gtc tct ggt ggc tcc atc agc agt ggt      96
Thr Leu Ser Leu Thr Cys Ala Val Ser Gly Gly Ser Ile Ser Ser Gly
                 20                  25                  30 ggt tac tcc tgg agc tgg atc cgg cag cca cca ggg aag ggc ctg gag     144
Gly Tyr Ser Trp Ser Trp Ile Arg Gln Pro Pro Gly Lys Gly Leu Glu
             35                  40                  45 tgg att ggg tac atc tat cat agt ggg agc acc tac tac aac ccg tcc     192
Trp Ile Gly Tyr Ile Tyr His Ser Gly Ser Thr Tyr Tyr Asn Pro Ser
 50                  55                  60 ctc aag agt cga gtc acc ata tca gta gac agg tcc aag aac cag ttc     240
Leu Lys Ser Arg Val Thr Ile Ser Val Asp Arg Ser Lys Asn Gln Phe
 65                  70                  75                  80 tcc ctg aag ctg agc tct gtg acc gcc gcg gac acg gcc gtg tat tac     288
Ser Leu Lys Leu Ser Ser Val Thr Ala Ala Asp Thr Ala Val Tyr Tyr
                 85                  90                  95 tgt gcc aga ga                                                      299
Cys Ala Arg <210> SEQ ID NO 4
<211> LENGTH: 99
<212> TYPE: PRT
<213> ORGANISM: Artificial
<220> FEATURE:
<223> OTHER INFORMATION: Synthetic Construct

<400> SEQUENCE: 4

Gln Leu Gln Leu Gln Glu Ser Gly Ser Gly Leu Val Lys Pro Ser Gln
 1               5                  10                  15

Thr Leu Ser Leu Thr Cys Ala Val Ser Gly Gly Ser Ile Ser Ser Gly
                 20                  25                  30

Gly Tyr Ser Trp Ser Trp Ile Arg Gln Pro Pro Gly Lys Gly Leu Glu
             35                  40                  45

Trp Ile Gly Tyr Ile Tyr His Ser Gly Ser Thr Tyr Tyr Asn Pro Ser
 50                  55                  60

Leu Lys Ser Arg Val Thr Ile Ser Val Asp Arg Ser Lys Asn Gln Phe
 65                  70                  75                  80

Ser Leu Lys Leu Ser Ser Val Thr Ala Ala Asp Thr Ala Val Tyr Tyr
                 85                  90                  95

Cys Ala Arg

<210> SEQ ID NO 5
```

```
<211> LENGTH: 299
<212> TYPE: DNA
<213> ORGANISM: Artificial
<220> FEATURE:
<223> OTHER INFORMATION: Synthetic primer
<220> FEATURE:
<221> NAME/KEY: CDS
<222> LOCATION: (1)..(297)

<400> SEQUENCE: 5 cag gtg cag ctg cag gag tcg ggc cca gga ctg gtg aag cct tca cag      48
Gln Val Gln Leu Gln Glu Ser Gly Pro Gly Leu Val Lys Pro Ser Gln
1               5                   10                  15 acc ctg tcc ctc acc tgc act gtc tct ggt ggc tcc atc agc agt ggt      96
Thr Leu Ser Leu Thr Cys Thr Val Ser Gly Gly Ser Ile Ser Ser Gly
            20                  25                  30 gat tac tac tgg agt tgg atc cgc cag ccc cca ggg aag ggc ctg gag     144
Asp Tyr Tyr Trp Ser Trp Ile Arg Gln Pro Pro Gly Lys Gly Leu Glu
        35                  40                  45 tgg att ggg tac atc tat tac agt ggg agc acc tac tac aac ccg tcc     192
Trp Ile Gly Tyr Ile Tyr Tyr Ser Gly Ser Thr Tyr Tyr Asn Pro Ser
    50                  55                  60 ctc aag agt cga gtt acc ata tca gta gac acg tcc aag aac cag ttc     240
Leu Lys Ser Arg Val Thr Ile Ser Val Asp Thr Ser Lys Asn Gln Phe
65                  70                  75                  80 tcc ctg aag ctg agc tct gtg act gcc gca gac acg gcc gtg tat tac     288
Ser Leu Lys Leu Ser Ser Val Thr Ala Ala Asp Thr Ala Val Tyr Tyr
                85                  90                  95 tgt gcc aga ga                                                      299
Cys Ala Arg <210> SEQ ID NO 6
<211> LENGTH: 99
<212> TYPE: PRT
<213> ORGANISM: Artificial
<220> FEATURE:
<223> OTHER INFORMATION: Synthetic Construct

<400> SEQUENCE: 6

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Asp Tyr Tyr Trp Ser Trp Ile Arg Gln Pro Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg

<210> SEQ ID NO 7
<211> LENGTH: 299
<212> TYPE: DNA
<213> ORGANISM: Artificial
<220> FEATURE:
<223> OTHER INFORMATION: Synthetic primer
<220> FEATURE:
<221> NAME/KEY: CDS
<222> LOCATION: (1)..(297)

<400> SEQUENCE: 7
```

```
cag gtg cag ctg cag gag tcg ggc cca gga ctg gtg aag cct tca cag      48
Gln Val Gln Leu Gln Glu Ser Gly Pro Gly Leu Val Lys Pro Ser Gln
1               5                   10                  15 acc ctg tcc ctc acc tgc act gtc tct ggt ggc tcc atc agc agt ggt      96
Thr Leu Ser Leu Thr Cys Thr Val Ser Gly Gly Ser Ile Ser Ser Gly
            20                  25                  30 ggt tac tac tgg agc tgg atc cgc cag cac cca ggg aag ggc ctg gag     144
Gly Tyr Tyr Trp Ser Trp Ile Arg Gln His Pro Gly Lys Gly Leu Glu
        35                  40                  45 tgg att ggg tac atc tat tac agt ggg agc acc tac tac aac ccg tcc     192
Trp Ile Gly Tyr Ile Tyr Tyr Ser Gly Ser Thr Tyr Tyr Asn Pro Ser
    50                  55                  60 ctc aag agt cta gtt acc ata tca gta gac acg tct aag aac cag ttc     240
Leu Lys Ser Leu Val Thr Ile Ser Val Asp Thr Ser Lys Asn Gln Phe
65                  70                  75                  80 tcc ctg aag ctg agc tct gtg act gcc gcg gac acg gcc gtg tat tac     288
Ser Leu Lys Leu Ser Ser Val Thr Ala Ala Asp Thr Ala Val Tyr Tyr
                85                  90                  95 tgt gcg aga ga                                                       299
Cys Ala Arg <210> SEQ ID NO 8
<211> LENGTH: 99
<212> TYPE: PRT
<213> ORGANISM: Artificial
<220> FEATURE:
<223> OTHER INFORMATION: Synthetic Construct

<400> SEQUENCE: 8

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

Leu Lys Ser Leu Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg

<210> SEQ ID NO 9
<211> LENGTH: 293
<212> TYPE: DNA
<213> ORGANISM: Artificial
<220> FEATURE:
<223> OTHER INFORMATION: Synthetic primer
<220> FEATURE:
<221> NAME/KEY: CDS
<222> LOCATION: (1)..(291)

<400> SEQUENCE: 9 cag gtg cag cta cag cag tgg ggc gca gga ctg ttg aag cct tcg gag      48
Gln Val Gln Leu Gln Gln Trp Gly Ala Gly Leu Leu Lys Pro Ser Glu
1               5                   10                  15 acc ctg tcc ctc acc tgc gct gtc tat ggt ggg tcc ttc agt ggt tac      96
Thr Leu Ser Leu Thr Cys Ala Val Tyr Gly Gly Ser Phe Ser Gly Tyr
            20                  25                  30 tac tgg agc tgg atc cgc cag ccc cca ggg aag ggg ctg gag tgg att     144
```

```
Tyr Trp Ser Trp Ile Arg Gln Pro Pro Gly Lys Gly Leu Glu Trp Ile
             35                  40                  45 ggg gaa atc aat cat agt gga agc acc aac tac aac ccg tcc ctc aag    192
Gly Glu Ile Asn His Ser Gly Ser Thr Asn Tyr Asn Pro Ser Leu Lys
 50                  55                  60 agt cga gtc acc ata tca gta gac acg tcc aag aac cag ttc tcc ctg    240
Ser Arg Val Thr Ile Ser Val Asp Thr Ser Lys Asn Gln Phe Ser Leu
 65                  70                  75                  80 aag ctg agc tct gtg acc gcc gcg gac acg gct gtg tat tac tgt gcg    288
Lys Leu Ser Ser Val Thr Ala Ala Asp Thr Ala Val Tyr Tyr Cys Ala
                 85                  90                  95 aga gg                                                              293
Arg

<210> SEQ ID NO 10
<211> LENGTH: 97
<212> TYPE: PRT
<213> ORGANISM: Artificial
<220> FEATURE:
<223> OTHER INFORMATION: Synthetic Construct

<400> SEQUENCE: 10

Gln Val Gln Leu Gln Gln Trp Gly Ala Gly Leu Leu Lys Pro Ser Glu
 1               5                  10                  15

Thr Leu Ser Leu Thr Cys Ala Val Tyr Gly Gly Ser Phe Ser Gly Tyr
                 20                  25                  30

Tyr Trp Ser Trp Ile Arg Gln Pro Pro Gly Lys Gly Leu Glu Trp Ile
             35                  40                  45

Gly Glu Ile Asn His Ser Gly Ser Thr Asn Tyr Asn Pro Ser Leu Lys
 50                  55                  60

Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Arg

<210> SEQ ID NO 11
<211> LENGTH: 299
<212> TYPE: DNA
<213> ORGANISM: Artificial
<220> FEATURE:
<223> OTHER INFORMATION: Synthetic primer
<220> FEATURE:
<221> NAME/KEY: CDS
<222> LOCATION: (1)..(297)

<400> SEQUENCE: 11 cag ctg cag ctg cag gag tcg ggc cca gga ctg gtg aag cct tcg gag     48
Gln Leu Gln Leu Gln Glu Ser Gly Pro Gly Leu Val Lys Pro Ser Glu
 1               5                  10                  15 acc ctg tcc ctc acc tgc act gtc tct ggt ggc tcc atc agc agt agt     96
Thr Leu Ser Leu Thr Cys Thr Val Ser Gly Gly Ser Ile Ser Ser Ser
                 20                  25                  30 agt tac tac tgg ggc tgg atc cgc cag ccc cca ggg aag ggg ctg gag    144
Ser Tyr Tyr Trp Gly Trp Ile Arg Gln Pro Pro Gly Lys Gly Leu Glu
             35                  40                  45 tgg att ggg agt atc tat tat agt ggg agc acc tac tac aac ccg tcc    192
Trp Ile Gly Ser Ile Tyr Tyr Ser Gly Ser Thr Tyr Tyr Asn Pro Ser
 50                  55                  60 ctc aag agt cga gtc acc ata tcc gta gac acg tcc aag aac cag ttc    240
Leu Lys Ser Arg Val Thr Ile Ser Val Asp Thr Ser Lys Asn Gln Phe
 65                  70                  75                  80
```

```
tcc ctg aag ctg agc tct gtg acc gcc gca gac acg gct gtg tat tac    288
Ser Leu Lys Leu Ser Ser Val Thr Ala Ala Asp Thr Ala Val Tyr Tyr
                85                  90                  95 tgt gcg aga ca                                                      299
Cys Ala Arg
```

<210> SEQ ID NO 12
<211> LENGTH: 99
<212> TYPE: PRT
<213> ORGANISM: Artificial
<220> FEATURE:
<223> OTHER INFORMATION: Synthetic Construct

<400> SEQUENCE: 12

```
Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
                20                  25                  30

Ser Tyr Tyr Trp Gly Trp Ile Arg Gln Pro Pro Gly Lys Gly Leu Glu
            35                  40                  45

Trp Ile Gly Ser Ile Tyr Tyr Ser Gly Ser Thr Tyr Tyr Asn Pro Ser
50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg
```

<210> SEQ ID NO 13
<211> LENGTH: 296
<212> TYPE: DNA
<213> ORGANISM: Artificial
<220> FEATURE:
<223> OTHER INFORMATION: Synthetic primer
<220> FEATURE:
<221> NAME/KEY: CDS
<222> LOCATION: (1)..(294)

<400> SEQUENCE: 13

```
cag gtg cag ctg cag gag tcg ggc cca gga ctg gtg aag cct ccg ggg    48
Gln Val Gln Leu Gln Glu Ser Gly Pro Gly Leu Val Lys Pro Pro Gly
1               5                   10                  15 acc ctg tcc ctc acc tgc gct gtc tct ggt ggc tcc atc agc agt agt    96
Thr Leu Ser Leu Thr Cys Ala Val Ser Gly Gly Ser Ile Ser Ser Ser
                20                  25                  30 aac tgg tgg agt tgg gtc cgc cag ccc cca ggg aag ggg ctg gag tgg   144
Asn Trp Trp Ser Trp Val Arg Gln Pro Pro Gly Lys Gly Leu Glu Trp
            35                  40                  45 att ggg gaa atc tat cat agt ggg agc acc aac tac aac ccg tcc ctc   192
Ile Gly Glu Ile Tyr His Ser Gly Ser Thr Asn Tyr Asn Pro Ser Leu
50                  55                  60 aag agt cga gtc acc ata tca gta gac aag tcc aag aac cag ttc tcc   240
Lys Ser Arg Val Thr Ile Ser Val Asp Lys Ser Lys Asn Gln Phe Ser
65                  70                  75                  80 ctg aag ctg agc tct gtg acc gcc gcg gac acg gcc gtg tat tgc tgt   288
Leu Lys Leu Ser Ser Val Thr Ala Ala Asp Thr Ala Val Tyr Cys Cys
                85                  90                  95 gcg aga ga                                                         296
Ala Arg
```

<210> SEQ ID NO 14

```
<211> LENGTH: 98
<212> TYPE: PRT
<213> ORGANISM: Artificial
<220> FEATURE:
<223> OTHER INFORMATION: Synthetic Construct

<400> SEQUENCE: 14

Gln Val Gln Leu Gln Glu Ser Gly Pro Gly Leu Val Lys Pro Pro Gly
1               5                   10                  15

Thr Leu Ser Leu Thr Cys Ala Val Ser Gly Gly Ser Ile Ser Ser Ser
            20                  25                  30

Asn Trp Trp Ser Trp Val Arg Gln Pro Pro Gly Lys Gly Leu Glu Trp
        35                  40                  45

Ile Gly Glu Ile Tyr His Ser Gly Ser Thr Asn Tyr Asn Pro Ser Leu
50                  55                  60

Lys Ser Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Cys Cys
                85                  90                  95

Ala Arg

<210> SEQ ID NO 15
<211> LENGTH: 293
<212> TYPE: DNA
<213> ORGANISM: Artificial
<220> FEATURE:
<223> OTHER INFORMATION: Synthetic primer
<220> FEATURE:
<221> NAME/KEY: CDS
<222> LOCATION: (1)..(291)

<400> SEQUENCE: 15 cag gtg cag ctg cag gag tcg ggc cca gga ctg gtg aag cct tcg gag      48
Gln Val Gln Leu Gln Glu Ser Gly Pro Gly Leu Val Lys Pro Ser Glu
1               5                   10                  15 acc ctg tcc ctc acc tgc act gtc tct ggt ggc tcc atc agt agt tac      96
Thr Leu Ser Leu Thr Cys Thr Val Ser Gly Gly Ser Ile Ser Ser Tyr
            20                  25                  30 tac tgg agc tgg atc cgg cag ccc cca ggg aag gga ctg gag tgg att     144
Tyr Trp Ser Trp Ile Arg Gln Pro Pro Gly Lys Gly Leu Glu Trp Ile
        35                  40                  45 ggg tat atc tat tac agt ggg agc acc aac tac aac ccc tcc ctc aag     192
Gly Tyr Ile Tyr Tyr Ser Gly Ser Thr Asn Tyr Asn Pro Ser Leu Lys
50                  55                  60 agt cga gtc acc ata tca gta gac acg tcc aag aac cag ttc tcc ctg     240
Ser Arg Val Thr Ile Ser Val Asp Thr Ser Lys Asn Gln Phe Ser Leu
65                  70                  75                  80 aag ctg agc tct gtg acc gct gcg gac acg gcc gtg tat tac tgt gcg     288
Lys Leu Ser Ser Val Thr Ala Ala Asp Thr Ala Val Tyr Tyr Cys Ala
                85                  90                  95 aga ga                                                               293
Arg

<210> SEQ ID NO 16
<211> LENGTH: 97
<212> TYPE: PRT
<213> ORGANISM: Artificial
<220> FEATURE:
<223> OTHER INFORMATION: Synthetic Construct

<400> SEQUENCE: 16

Gln Val Gln Leu Gln Glu Ser Gly Pro Gly Leu Val Lys Pro Ser Glu
1               5                   10                  15
```

```
Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg

<210> SEQ ID NO 17
<211> LENGTH: 299
<212> TYPE: DNA
<213> ORGANISM: Artificial
<220> FEATURE:
<223> OTHER INFORMATION: Synthetic primer
<220> FEATURE:
<221> NAME/KEY: CDS
<222> LOCATION: (1)..(297)

<400> SEQUENCE: 17 cag gtg cag ctg cag gag tcg ggc cca gga ctg gtg aag cct tcg gag      48
Gln Val Gln Leu Gln Glu Ser Gly Pro Gly Leu Val Lys Pro Ser Glu
1               5                   10                  15 acc ctg tcc ctc acc tgc act gtc tct ggt ggc tcc gtc agc agt ggt      96
Thr Leu Ser Leu Thr Cys Thr Val Ser Gly Gly Ser Val Ser Ser Gly
            20                  25                  30 agt tac tac tgg agc tgg atc cgg cag ccc cca ggg aag gga ctg gag     144
Ser Tyr Tyr Trp Ser Trp Ile Arg Gln Pro Pro Gly Lys Gly Leu Glu
        35                  40                  45 tgg att ggg tat atc tat tac agt ggg agc acc aac tac aac ccc tcc     192
Trp Ile Gly Tyr Ile Tyr Tyr Ser Gly Ser Thr Asn Tyr Asn Pro Ser
    50                  55                  60 ctc aag agt cga gtc acc ata tca gta gac acg tcc aag aac cag ttc     240
Leu Lys Ser Arg Val Thr Ile Ser Val Asp Thr Ser Lys Asn Gln Phe
65                  70                  75                  80 tcc ctg aag ctg agc tct gtg acc gct gcg gac acg gcc gtg tat tac     288
Ser Leu Lys Leu Ser Ser Val Thr Ala Ala Asp Thr Ala Val Tyr Tyr
                85                  90                  95 tgt gcg aga ga                                                       299
Cys Ala Arg <210> SEQ ID NO 18
<211> LENGTH: 99
<212> TYPE: PRT
<213> ORGANISM: Artificial
<220> FEATURE:
<223> OTHER INFORMATION: Synthetic Construct

<400> SEQUENCE: 18

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Val Ser Ser Gly
            20                  25                  30

Ser Tyr Tyr Trp Ser Trp Ile Arg Gln Pro Pro Gly Lys Gly Leu Glu
        35                  40                  45

Trp Ile Gly Tyr Ile Tyr Tyr Ser Gly Ser Thr Asn Tyr Asn Pro Ser
    50                  55                  60
```

```
Leu Lys Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                 85                  90                  95

Cys Ala Arg

<210> SEQ ID NO 19
<211> LENGTH: 294
<212> TYPE: DNA
<213> ORGANISM: Artificial
<220> FEATURE:
<223> OTHER INFORMATION: Synthetic primer
<220> FEATURE:
<221> NAME/KEY: CDS
<222> LOCATION: (1)..(291)

<400> SEQUENCE: 19 cag gtg cag ctg cag gag tcg ggc cca gga ctg gtg aag cct tcg gag    48
Gln Val Gln Leu Gln Glu Ser Gly Pro Gly Leu Val Lys Pro Ser Glu
 1               5                  10                  15 acc ctg tcc ctc acc tgc gct gtc tct ggt tac tcc atc agc agt ggt    96
Thr Leu Ser Leu Thr Cys Ala Val Ser Gly Tyr Ser Ile Ser Ser Gly
             20                  25                  30 tac tac tgg ggc tgg atc cgg cag ccc cca ggg aag ggg ctg gag tgg   144
Tyr Tyr Trp Gly Trp Ile Arg Gln Pro Pro Gly Lys Gly Leu Glu Trp
         35                  40                  45 att ggg agt atc tat cat agt ggg agc acc tac tac aac ccg tcc ctc   192
Ile Gly Ser Ile Tyr His Ser Gly Ser Thr Tyr Tyr Asn Pro Ser Leu
     50                  55                  60 aag agt cga gtc acc ata tca gta gac acg tcc aag aac cag ttc tcc   240
Lys Ser Arg Val Thr Ile Ser Val Asp Thr Ser Lys Asn Gln Phe Ser
 65                  70                  75                  80 ctg aag ctg agc tct gtg acc gcc gca gac acg gcc gtg tat tac tgt   288
Leu Lys Leu Ser Ser Val Thr Ala Ala Asp Thr Ala Val Tyr Tyr Cys
                 85                  90                  95 gcg aga                                                            294
Ala

<210> SEQ ID NO 20
<211> LENGTH: 97
<212> TYPE: PRT
<213> ORGANISM: Artificial
<220> FEATURE:
<223> OTHER INFORMATION: Synthetic Construct

<400> SEQUENCE: 20

Gln Val Gln Leu Gln Glu Ser Gly Pro Gly Leu Val Lys Pro Ser Glu
 1               5                  10                  15

Thr Leu Ser Leu Thr Cys Ala Val Ser Gly Tyr Ser Ile Ser Ser Gly
             20                  25                  30

Tyr Tyr Trp Gly Trp Ile Arg Gln Pro Pro Gly Lys Gly Leu Glu Trp
         35                  40                  45

Ile Gly Ser Ile Tyr His Ser Gly Ser Thr Tyr Tyr Asn Pro Ser Leu
     50                  55                  60

Lys Ser Arg Val Thr Ile Ser Val Asp Thr Ser Lys Asn Gln Phe Ser
 65                  70                  75                  80

Leu Lys Leu Ser Ser Val Thr Ala Ala Asp Thr Ala Val Tyr Tyr Cys
                 85                  90                  95

Ala
```